(12) United States Patent
Siadak et al.

(10) Patent No.: US 8,017,122 B2
(45) Date of Patent: Sep. 13, 2011

(54) METHODS OF USING IL-31 MONOCLONAL ANTIBODIES TO REDUCE INFLAMMATION

(75) Inventors: Anthony W. Siadak, Seattle, WA (US); Janine Bilsborough, Seattle, WA (US); Shirley Rene, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/420,747

(22) Filed: Apr. 8, 2009

(65) Prior Publication Data

US 2009/0220417 A1 Sep. 3, 2009

Related U.S. Application Data

(62) Division of application No. 11/430,066, filed on May 8, 2006, now Pat. No. 7,531,637.

(60) Provisional application No. 60/678,918, filed on May 6, 2005, provisional application No. 60/696,251, filed on Jul. 1, 2005, provisional application No. 60/711,600, filed on Aug. 26, 2005.

(51) Int. Cl.
*A61K 39/395* (2006.01)

(52) U.S. Cl. .......... 424/145.1; 424/141.1; 424/1.49; 514/885; 514/886

(58) Field of Classification Search .......... None
See application file for complete search history.

(56) References Cited

U.S. PATENT DOCUMENTS

| | | | |
|---|---|---|---|
| 4,054,646 A | 10/1977 | Giaever | |
| 5,116,964 A | 5/1992 | Capon et al. | |
| 5,492,841 A | 2/1996 | Craig | |
| 5,530,101 A | 6/1996 | Queen et al. | |
| 5,891,997 A | 4/1999 | Mosley et al. | |
| 5,925,735 A | 7/1999 | Baumgartner et al. | |
| 6,043,344 A | 3/2000 | Jacobs et al. | |
| 6,086,874 A | 7/2000 | Yoshida et al. | |
| 7,064,186 B2 | 6/2006 | Sprecher et al. | |
| 7,303,896 B2 | 12/2007 | Ghilardi et al. | |
| 7,425,325 B2 | 9/2008 | Sprecher et al. | |
| 7,427,494 B2 | 9/2008 | Sprecher et al. | |
| 7,459,293 B2 | 12/2008 | Sprecher et al. | |
| 7,494,804 B2 | 2/2009 | Sprecher et al. | |
| 7,495,080 B2 | 2/2009 | Sprecher et al. | |
| 7,507,795 B2 | 3/2009 | Sprecher et al. | |
| 7,514,077 B2 | 4/2009 | Yao et al. | |
| 7,521,537 B2 | 4/2009 | Sprecher et al. | |
| 7,531,636 B2 | 5/2009 | Sprecher et al. | |
| 7,531,637 B2 | 5/2009 | Siadak et al. | |
| 7,638,126 B2 | 12/2009 | Yao et al. | |
| 7,723,048 B2 | 5/2010 | Bilsborough et al. | |
| 7,740,834 B2 | 6/2010 | Sprecher et al. | |
| 7,799,323 B2 | 9/2010 | Bilsborough et al. | |
| 2003/0096339 A1 | 5/2003 | Sprecher et al. | |
| 2004/0142422 A1 | 7/2004 | Sprecher et al. | |
| 2004/0152161 A1 | 8/2004 | Cosman et al. | |
| 2005/0214801 A1 | 9/2005 | Sprecher et al. | |
| 2006/0182743 A1 | 8/2006 | Bilsborough | |
| 2006/0188499 A1 | 8/2006 | Leung et al. | |
| 2006/0188500 A1 | 8/2006 | Leung et al. | |
| 2006/0228329 A1 | 10/2006 | Brady et al. | |
| 2007/0048222 A1 | 3/2007 | Sprecher et al. | |
| 2007/0048223 A1 | 3/2007 | Sprecher et al. | |
| 2007/0048303 A1 | 3/2007 | Sprecher et al. | |
| 2007/0048307 A1 | 3/2007 | Sprecher et al. | |
| 2007/0048308 A1 | 3/2007 | Sprecher et al. | |
| 2007/0048831 A1 | 3/2007 | Sprecher et al. | |
| 2007/0048832 A1 | 3/2007 | Sprecher et al. | |
| 2007/0048833 A1 | 3/2007 | Sprecher et al. | |
| 2007/0048834 A1 | 3/2007 | Sprecher et al. | |
| 2007/0048835 A1 | 3/2007 | Sprecher et al. | |
| 2007/0049530 A1 | 3/2007 | Sprecher et al. | |
| 2007/0105777 A1 | 5/2007 | Sprecher et al. | |
| 2007/0140963 A1 | 6/2007 | Sprecher et al. | |
| 2007/0140964 A1 | 6/2007 | Sprecher et al. | |
| 2007/0141051 A1 | 6/2007 | Sprecher et al. | |
| 2008/0026402 A1 | 1/2008 | Cosman et al. | |
| 2009/0149635 A1 | 6/2009 | Sprecher et al. | |
| 2009/0208494 A1 | 8/2009 | Bondensgaard et al. | |
| 2009/0220417 A1 | 9/2009 | Siadak et al. | |
| 2009/0252730 A1 | 10/2009 | Bilsborough | |
| 2009/0252732 A1 | 10/2009 | Siadak et al. | |
| 2009/0274694 A1 | 11/2009 | Sprecher et al. | |
| 2009/0274700 A1 | 11/2009 | Presnell et al. | |
| 2009/0280121 A1 | 11/2009 | Bilsborough et al. | |
| 2010/0008909 A1 | 1/2010 | Siadak et al. | |
| 2010/0055101 A1 | 3/2010 | Sprecher et al. | |

(Continued)

FOREIGN PATENT DOCUMENTS

EP 1188830 3/2002

(Continued)

OTHER PUBLICATIONS

Wills-Karp, M., "The gene encoding inerleukin-13: a susceptibility locus for asthma and related traits," Respiratory Research, 1(1): 19-23, Jul. 17, 2000.
Connors et al., "Hematology", pp. 263-268, Am Soc Hamatol Educ Program, 2002.
Oostingh et al., "Autoreactive T cell response in pemphigus and pemphigoid," Autoimmun Rev. 1(5): 267-272, 2002.
Heng et al., "Alpha-1 antitrypsin deficiency in a patient with widespread prurigo nodularis," Australas J Dermatol 32(3): 151-157, 1991, Abstract Only.
Stander et al., "Treatment of prurigo nodularis with topical capsaicin," J Am Acad Dermatol. 44(3): 471-478, Mar. 2001, Abstract Only.

(Continued)

*Primary Examiner* — Prema Mertz
(74) *Attorney, Agent, or Firm* — Brian J. Walsh

(57) ABSTRACT

The present invention relates to methods of treating pruritic diseases, including but not limited to Contact dermatitis, Atopic Dermatitis, Drug induced delayed type cutaneous allergic reactions, Toxic epidermal necrolysis, Cutaneous T cell Lymphoma, Bullous pemphigoid, Alopecia wereata, Vitiligo, Acne Rosacea, Prurigo nodularis, Scleroderma, Herpes simplex virus, or combination thereof by administering IL-31 monoclonal antibodies. The invention further provides the hybridomas that generate the monoclonal antibodies.

18 Claims, No Drawings

U.S. PATENT DOCUMENTS

| | | |
|---|---|---|
| 2010/0221244 A1 | 9/2010 | Yao et al. |
| 2010/0266499 A1 | 10/2010 | Sprecher et al. |
| 2010/0266597 A1 | 10/2010 | Sprecher et al. |
| 2010/0266600 A1 | 10/2010 | Bilsborough et al. |
| 2010/0297065 A1 | 11/2010 | Brady et al. |
| 2010/0297125 A1 | 11/2010 | Yao et al. |
| 2011/0008820 A1 | 1/2011 | Bilsborough et al. |

FOREIGN PATENT DOCUMENTS

| | | |
|---|---|---|
| JP | 10-501131 | 2/1998 |
| WO | 00/75314 | 12/2000 |
| WO | 01/93983 | 12/2001 |
| WO | 02/00690 | 1/2002 |
| WO | 02/00721 | 1/2002 |
| WO | 02/08288 | 1/2002 |
| WO | 02/29060 | 4/2002 |
| WO | 02/077230 | 10/2002 |
| WO | 03/060090 | 7/2003 |
| WO | 03/072740 | 9/2003 |
| WO | 2004/003140 | 1/2004 |
| WO | 2006/081573 | 8/2006 |
| WO | 2006/088955 | 8/2006 |
| WO | 2006/088956 | 8/2006 |
| WO | 2006/122079 | 11/2006 |
| WO | 2007/143231 | 12/2007 |
| WO | 2008/028192 | 3/2008 |
| WO | 2008/086505 | 7/2008 |
| WO | 2009/071696 | 6/2009 |

OTHER PUBLICATIONS

Fritsch et al., "Drug-induced Stevens-Johnson symdrom/toxic epidermal necrolysis," Am J Clin Dermatol. 1(6): 349-360, Nov.-Dec. 2000, Abstract Only.
Rufli et al., "T-cell subsets in acne rosacea lesions and the possible role of Demodex folliculorum," Dermatologica. 169(1): 1-5, 1984, Abstract Only.
Aurelian et al., "Herpes simplex virus (HSV)-associated erythema multiforme (HAEM): a viral disease with an autoimmune component," Dermatol Online J. 9(1): 1, Abstract Only.
Dillon et al., "Transgenic mice overexpressing a novel cytokine (IL-31) develop a severe pruritic skin phenotype resembling atopic dermatitis," European Cytokine Network 14(3): 81, 2003.
Bando et al., "Complete overlap of interleukin-31 receptor A and oncostatin M receptor beta in the adult dorsal root ganglia with distinct developmental expression patterns," Neuroscience 142(4): 1263-1271, 2006.
Perrigoue et al., "IL-31-IL-31R interactions negatively regulate type 2 inflammation in the lung," Journal of Experimental Medicine 204(3): 481-487, Mar. 19, 2007.
Jawa et al., "Expression, regulation and signaling by interleukin 31 receptor alpha (IL-31RA) in bronchnopulmonary epithelial cells and pulmonary macrophages," Assocation for Academic Surgery and Society of University Surgeons, abstract.
Nobbe et al., "IL-31 expression by inflammatory cell is unique to atopic dermatitis," Abstract. Submitted to 39th Annual European Society for Dermatological Research (ESDR) Meeting (Budapest, Hungary), Sep. 9, 2009.
Nobbe et al., "IL-31 expression by inflammatory cell is unique to atopic dermatitis," Abstract. Submitted to 91st Annual Meeting of the Swiss Society of Dermatology & Venereology (Basel, Switzerland), Aug. 4, 2009.
Grimstad et al., "Anti-interleukin-31-antibodies ameliorate scratching behaviour in NC/Nga mice: a model of atopic dermatitis," Exp Dermatol. 18(1): 35-43, Jan. 2009. (Epub Oct. 24, 2008).
Aioi, A. et al., Br J. Dermatol 144(1):12-18, 2001.
Akdis, C.A., et al., J. Invest. Dermatol. 113(4) 628-34, 1999.
Aleksza, M., et al., Br. J. Dermatol. 147(6):1135-41, 2002.
Antunez, C., et al., Clin. Exp. Allergy 34(4) 559-66, 2004.
Asadullah, K. et al., Arch. Dermatol 138(9):1189-96, 2002.
Askenase, P.W., Chem. Immunol. 78:112-23, 2000.
Barnes, K.C., et al., Genomics 37(1):41-50, 1996.
Berger, C.L., et al., Blood 105(4):1640-7, 2005.
Bonecchi, R., et al., J. Exp. Med. 187(1):129-34, 1998.
Dillon, S.R., et al., Nat. Immunol. 6(1):114, 2005.
Diveu, C., et al., Eur. Cytokine Netw. 15(4):291-302, 2004.
Diveu, C., et al., J. Biol. Chem. 278(50):49850-49859, 2003.
Dreuw, A., et al., Immunobiology 210(6-8), 454, 2005.
Dreuw, A., et al., Keystone Symposia "Cytokines, Disease and Therapeutic Intervention," Feb. 12-17, 2005.
Dreuw, A., et al., J. Biol. Chem. 279(34):36112-20, 2004.
Fang, D., et al., Nat. Immunol. 3(3):281-7, 2002.
Ghilardi, N. et al., J. Biol. Chem. 277(19):16831-16836, 2002.
Gutermuth, J. et al., Int. Arch. Allergy Immunol. 135(3):262-76, 2004.
Hammond, A., et al., Orphan class I cytokine receptor Zcytor17 is upregulated in activated monocytes and T cells. (W-2-4) S48.
Hashimoto, Y., et al., Life Sci. 76(7):783-94, 2004.
Hashimoto, Y., et al., J. Dermatol. Sci. 35(2):143-50, 2004.
Hermanns, H.M., et al., Experimental Dermatology 15(N3):219-20, 2006.
Hijnen, D., et al., J. Allergy Clin. Immunol. 113(2):334-40, 2004.
Hwang, S.T., Adv. Dermatol. 17:211-41, 2001.
Leung, D.Y., et al., Lancet 361(9352): 151-60, 2003.
Lin, L., et al., J. Med. Dent. Sci. 50(1):27-33, 2003.
Nagao, M., et al., J. Allergy Clin. Immunol. 15(2):s272, 2005.
Matsuda, H., et al., Int. Immunol. 9(3):461-6, 1997.
Matsushima, H., et al., J. Dermatol. Sci. 32(3):223-30, 2003.
Parrish-Novak, J.E., et al., Interleukin 31 is a novel four-helical-bundle cytokine that signals through a heterodimeric receptor complex expressed in epithelial cells of lung and skin, (1023) Annual Meeting of the American Society of Human Genetics, 2003.
Robert, C., et al., N. Engl. J. Med. 341(24):1817-28, 1999.
Shimada, Y., et al., J. Dermatol. Sci. 34(3):201-8, 2004.
Song, T., et al., J. Allergy Clin. Immunol. 15(2):s100, 2005.
Takano, N., et al., Eur. J. Pharmacol. 495(2-3):159-65, 2004.
Takano, N., et al., Eur. J. Pharmacol. 471(3):223-8, 2003.
Takaoka, A., Eur. J. Pharmacol. PMID:15925362, 2005.
Vestergaard, C., et al., J. Invest. Dermatol. 115(4):640-6, 2000.
GenBank Accession No. AI123586, 1997.
Gen Bank Accession No. AI799583, 1997.
CDTP64367599.
CDTP62671799.
GenBank Accession No. AI123586, Sep. 3, 1998.
GenBank Accession No. AI799583, Jul. 6, 1999.
Sprecher et al. (Notice of Allowance), U.S. Appl. No. 10/351,157, Jan. 24, 2004.
Daniel et al., "Mapping of linear antigenic sites on the S Glycoprotein of a neurotroic murine coronavirus with synthetic peptides," Virology 202: 540-549, 1994.
Lederman et al., "A single amino acid substitution in a common african allele of the CD4 molecule ablates binding of the monoclonal antibody, OKT4," Molecular Immunology 28(11): 1171-1181, 1991.
Bazan, "Structural design and molecular evolution of a cytokine receptor superfamily," Proc. Natl. Acad. Sci. USA, 87: 6934-6938 (Sep. 1990).
Singh et al., "IFN-γ-Inducible Chemokines Enhance Adaptive Immunity and Colitis," Journal of Interferon & Cytokine Research 23: 591-600, 2003.
Kaushansky and Drachman, "The molecular and cellular biology of thrombopoietin: the primary regulator of platelet production," Oncogene 21: 3359-3367, 2002.
Tamura et al., "Expression of oncostatin M receptor beta in a specific subset of nociceptive sensory neurons," European Journal of Neuroscience 14(11): 2287-2298, Jun. 2003.
Steinhoff et al., "Modern aspects of cutaneous neurogenic inflammation," Archives of Dermatology 139(11): 1479-1488, Nov. 2003.
Dillon et al., Entrez Database Accession No. AY499341, Jul. 10, 2004.
ExPASy Feature Aligner, Q8N17 (IL-31RA) human (accessed Nov. 11, 2007).
PFAM, FN3 (accessed Nov. 11, 2007).
SMART Domain Annotation—FN3 domain (accessed Nov. 11, 2007).
Harlow et al., Ed. Antibodies, A Laboratory Manual. Cold Spring Harbor Press. 1998, pp. 23-26.

Felderhoff-Muesser et al., "IL-18: a key player in neuroinflammation and neurodegeneration," TRENDS in Neurosciences 28(9): 487-493, 2005.
Miller, G., "Breaking down barriers," Science 297: 1116-1118, 2002.
Pettit et al., "The development of site-specific drug-delivery systems for protein and peptide biopharmaceuticals," Trends in Biotechnology 16: 343-349, 1998.
U.S. Appl. No. 11/430,066, Non-Final Rejection mailed May 1, 2008.
Perrigoue et al., "IL-31-IL-31R interactions negatively regulate type 2 inflammation in the lung," J. Exp. Med. 204(3): 481-7, Mar. 19, 2007. Epub Mar. 12 2007; PMID: 17353366 Publisher: J Exp Med.
Ip et al., "Interleukin-31 induces cytokine and chemokine production from human bronchial epithelial cells through activation of mitogen-activated protein kinase signalling pathways: implications for the allergic response," Immunology, Jul. 11, 2007; PMID: 17449633 Publisher: Gut.
Dambacher et al., "Orphan class I cytokine receptor Zcytor17 is upregulated in activated monocytes and T cells," (W-2-4), Gut, Apr. 20, 2007; PMID: 17449633 Publisher: Gut.
Schulz et al., "A common haplotype of the IL-31 gene influencing gene expression is associated with nonatopic eczema," Journal of Allergy and Clinical Immunology 120(5): 1097-1102, Nov. 1, 2007.
Boder et al., "Directed evolution of antibody fragments with monovalent femtomolar antigen-binding affinity," Proceedings of the National Academy of Sciences of USA 97(20): 10701-10705, Sep. 26, 2000.
Definition of "lichenification" in Stedman's Medical Dictionary, 27th Ed. (2000 Lippincott Williams & Wilkins).
Burgess et al., "Possible dissociation of the heparin-binding and mitogenic activities of heparing binding (acidic fibroblast) growth factor 1 from its receptor binding activities by site directed mutagenesis of a single lysine residue," Journal of Cell Biology 111: 2129-2138, 1990.
Lazar et al., "Transforming growth factor alpha: mutation of aspartic acid 47 and leucine 48 results in different biological activities," Molecular and Cellular Biology 8: 1247-1252, 1988.
Rudikoff et al., "Single amino acid substitution altering antigen-binding specificity," Proceedings of the National Academy of Science 79: 1979-1983, 1982.
MacCallum et al., "Antibody-antigen interactions: contact analysis and binding site topography," Journal of Molecular Biology 262: 732-745, 1996.
DePascalis et al, "Graftting of abbreviated complementarity determining regions containing specificity determining residues essential for ligand contact to engineer a less immunogenic humanized monoclonal antibody," Journal of Immunology 169: 3076-3084, 2002.
Casset et al., "A peptide mimetic of an anti-CD4 monoclonal antibody by rational design," Biochemical and Biophysical Research Communication 307: 198-205, 2003.
Vajdos et al., "Comprehensive functional maps of the antigen binding site of an anti-ErbB2 antibody obtaining by shotgun scanning mutagenesis," Journal of Molecular Biology 320: 415-428, 2002.
Holm et al., "Functional mapping and single chain construction of the anti-cytokeratin 8 monoclonal antibody TS1," Molecular Immunology 44: 1075-1084, 2007.
Chen et al., "Selection and analysis of an optimized anti-VEGF antibody: crystal structure of an affinity matured Fab in complex with antigen," Journal of Molecular Biology 293: 865-881, 1999.
Wu et al., "Humanization of a murine monoclonal antibody by simultaneous optimization of framework and CDR residues," Journal of Molecular Biology 294: 151-162: 1999.
Lewis et al., "Comparison of the ability of wild type and stabilized human IgG4 to undergo Fab arm exchange with endogenous IgG4 in vitro and in vivo," Molecular Immunology, 1-7, 2009.
Bilsborough, "IL-31 is Associated with CLA+ Skin Homing T cells in Patients with Atopic Dermatitis," Cytokine Symposium, Vienna, Austria, Aug. 2006.
Leung et al., "IL-31 in Atopic Dermatitis," Grand Rounds Lecture, National Jewish Medical Center, Denver, CO, Dec. 14, 2005.
Leung et al., "IL-31 in Atopic Dermatitis," Grand Rounds, Mt. Sinai Medical Centre, New York, Jan. 5, 2006.
Sprecher et al., U.S. Appl. No. 12/756,959, filed Apr. 8, 2010.
Riken, 1999, (GenBank Acc. No. AV040649).
Riken, 1999, (GenBank Acc. No. AV044404).
Riken, 1999, (GenBank Ace. No. AV268991).
Riken, 1999, (GenBank Acc. No. AV280874).
National Cancer Institute, 1997, (GenBank Acc. No. BF152807).
Riken, 2001, (GenBank Acc. No. BB610257).
Riken, Accession No. AK005939, 1999.
Riken, Accession No. AK005939, Jul. 5, 2001.
National Institutes of Health, 1999, (GenBank Acc. No. CA464033).
Riken, 2002, (GenBank Acc. No. BY706076).
Washington University School of Medicine, 2002, (GenBank Acc. No. CF105870).
RZPD Deutsches Ressourcenzentrum fuer Genomforschung GmbH, 2003, (GenBank Acc. No. BX639332).
Whitehead Institute for Biomedical Research, Mouse Public Genomic Sequence TDB 3482986, Jan. 11, 2001.
Washington University Genome Sequencing Center, Mouse Public Genomic Sequence TDB 16727183, Feb. 24, 2001.
Whitehead Institute for Biomedical Research, Mouse Public Genomic Sequence TDB 10456006, Mar. 14, 2001.
Washington University Genome Sequencing Center, Mouse Public Genomic Sequence TDB 8480322, Jan. 13, 2001.
Whitehead Institute for Biomedical Research, Mouse Public Genomic Sequence TDB 49775248, Oct. 5, 2001.
Whitehead Institute for Biomedical Research, Mouse Public Genomic Sequence TDB 10005090, Mar. 10, 2001.
Whitehead Institute for Biomedical Research, Mouse Public Genomic Sequence TDB 20965871, Mar. 16, 2001.
Whitehead Institute for Biomedical Research, Mouse Public Genomic Sequence TDB 44835892, Sep. 20, 2001.
Washington University Genome Sequencing Center, Mouse Public Genomic Sequence TDB 50734527, Oct. 6, 2001.
Sanger Center, Mouse Public Genomic Sequence TDB 40505897, Aug. 31, 2001.
Sanger Center, Mouse Public Genomic Sequence TDB 1021719, Jan. 4, 2001.
Washington University Genome Sequencing Center, Mouse Public Genomic Sequence TDB 22973884, Apr. 16, 2001.
Abstract from The American Society of Human Genetics Meeting, Nov. 7, 2003 on Gene Structure and Function.
EMBL Accession No. AC048338, Apr. 2000.
EMBL Accession No. AA381907, Apr. 1997.
Dillon et al., "Interleukin 31, a cytokine produced by activated T cells, induces dermatitis in mice," Nature Immunology 5(7):752-760, Jul. 2004.
Bilsborough et al., "IL-31 is associated with cutaneous lymphocyte antigen-positive skin homing T-cells in patients with atopic dermatitis", Journal of Allergy and Clinical Immunology, Mosby—Yearly Book, Inc., US 117(2): 418-425, Feb. 7, 2006.
Sonkoly et al., "IL-31: A new link between t-cells and pruritus in atopic skin inflammation", Journal of Allergy and Clinical Immunology, Mosby—Yearly Book, Inc., US 117(2): 411-417, Feb. 2006.
Takaoka et al., "Expression of IL-31 gene transcript in NC/Nga mice with atopic dermatitis", European Journal of Pharmacology, Amsterdam, NL, 516 (2): 180-181, May 31, 2005.
Goding, Journal of Immunological Methods vol. 39: 285-308, 1980.
Brune et al., Hautarzt 55: 1130-1136, 2004.
Ständer et al., Hautarzt 54: 413-417, 2003.
Claudy, Pathologie et Biologie, L'Expansion Scientifique Francaise, Paris, FR 44(10): 888-894, 1996.
Leung et al., "New insights into atopic dermititis", Journal of Clinical Investigation 113(5): 651-657, Mar. 2004.
Boguniewics et al., "Atopic dermititis", J Allergy Clin Immunol, 117(2): S475-S480, Feb. 2006.
Castellani et al., "Interleukin-31: A new cytokine involved in inflammation of the skin", International Journal of Immunopathology and Pharmacology, 19(1): 1-4, Jan. 13, 2006.
"Monoclonal Anti-human IL-31 Antibody", R&D Systems, Inc., Apr. 18, 2006.
Presta et al., "Engineering of therapeutic antibodies to minimize immunogenicity and optimize function," Advanced Drug Delivery Reviews 58(5-6): 640-656, 2006.

Conti et al., "Modulation of autoimmunity by the latest interleukins (with special emphasis on IL-32)" Autoimmunity Reviews 6(3): 131-137, 2007.

EMBL Accession No. AK005939, Feb. 8, 2001.

Neis et al., "Enhanced expression levels of IL-31 correlate with IL-4 and IL-13 in atopic and allergic contact dermatitis," Journal of Allergy and Clinical Immunology, 118(4): 930-937, Oct. 1, 2006.

Boder et al., "Directed evolution of antibody fragments with monovalent femtomolar antigen-binding affinity," Proceedings of the National Academy of Sciences of USA 97(20): 10701-10705, Sep. 26, 2000.

Takaoka et al., "Involvement of IL-31 on scratching behavior in NC/Nga mice with atopic-like dermatitis", Experimental Dermatology, 15 (3): 161-167, Mar. 2006.

SEQUENCE LISTING

<160> NUMBER OF SEQ ID NOS: 7

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)...(519)

<400> SEQUENCE: 1
ctgaagctgg ccttgctctc tctcgcc atg gcc tct cac tca ggc ccc tcg acg    54
                                Met Ala Ser His Ser Gly Pro Ser Thr
                                 1               5

-continued

```
tct gtg ctc ttt ctg ttc tgc tgc ctg gga ggc tgg ctg gcc tcc cac      102
Ser Val Leu Phe Leu Phe Cys Cys Leu Gly Gly Trp Leu Ala Ser His
    10                  15                  20                  25 acg ttg ccc gtc cgt tta cta cga cca agt gat gat gta cag aaa ata      150
Thr Leu Pro Val Arg Leu Leu Arg Pro Ser Asp Asp Val Gln Lys Ile
                30                  35                  40 gtc gag gaa tta cag tcc ctc tcg aag atg ctt ttg aaa gat gtg gag      198
Val Glu Glu Leu Gln Ser Leu Ser Lys Met Leu Leu Lys Asp Val Glu
            45                  50                  55 gaa gag aag ggc gtg ctc gtg tcc cag aat tac acg ctg ccg tgt ctc      246
Glu Glu Lys Gly Val Leu Val Ser Gln Asn Tyr Thr Leu Pro Cys Leu
        60                  65                  70 agc cct gac gcc cag ccg cca aac aac atc cac agc cca gcc atc cgg      294
Ser Pro Asp Ala Gln Pro Pro Asn Asn Ile His Ser Pro Ala Ile Arg
    75                  80                  85 gca tat ctc aag aca atc aga cag cta gac aac aaa tct gtt att gat      342
Ala Tyr Leu Lys Thr Ile Arg Gln Leu Asp Asn Lys Ser Val Ile Asp
90                  95                  100                 105 gag atc ata gag cac ctc gac aaa ctc ata ttt caa gat gca cca gaa      390
Glu Ile Ile Glu His Leu Asp Lys Leu Ile Phe Gln Asp Ala Pro Glu
                110                 115                 120 aca aac att tct gtg cca aca gac acc cat gaa tgt aaa cgc ttc atc      438
Thr Asn Ile Ser Val Pro Thr Asp Thr His Glu Cys Lys Arg Phe Ile
            125                 130                 135 ctg act att tct caa cag ttt tca gag tgc atg gac ctc gca cta aaa      486
Leu Thr Ile Ser Gln Gln Phe Ser Glu Cys Met Asp Leu Ala Leu Lys
        140                 145                 150 tca ttg acc tct gga gcc caa cag gcc acc act taaggccatc tcttcctttc    539
Ser Leu Thr Ser Gly Ala Gln Gln Ala Thr Thr
    155                 160 ggattggcag gaacttaagg agccttaaaa agatgaccga cagctaagtg tgggaactct    599
gccgtgattc cttaagtaca tttttccaat gaataatctc agggacccct catatgggct    659
agtcccggga gggctgagat gtgaatttgt gaattacctt gaaaaacatt aggttattgt    719
tattagtctt ggtatttatg gaatgctttt cttctgcagg cttaagtctt acttattata    779
ccctcgtgag ggtgggaggt ggcagctatg ttaatttatt gatatttatt gtactaagag    839
ttgtcaatgc tccctggggg agccctcgga atctatttaa taaattatat tgaattttc     899 tcata                                                                904
```

<210> SEQ ID NO 2
<211> LENGTH: 164
<212> TYPE: PRT
<213> ORGANISM: Homo sapiens

<400> SEQUENCE: 2

```
Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
                20                  25                  30

Arg Pro Ser Asp Asp Val Gln Lys Ile Val Glu Glu Leu Gln Ser Leu
            35                  40                  45

Ser Lys Met Leu Leu Lys Asp Val Glu Glu Lys Gly Val Leu Val
50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95
```

```
Gln Leu Asp Asn Lys Ser Val Ile Asp Glu Ile Ile Glu His Leu Asp
                100                 105                 110
Lys Leu Ile Phe Gln Asp Ala Pro Glu Thr Asn Ile Ser Val Pro Thr
            115                 120                 125
Asp Thr His Glu Cys Lys Arg Phe Ile Leu Thr Ile Ser Gln Gln Phe
130                 135                 140
Ser Glu Cys Met Asp Leu Ala Leu Lys Ser Leu Thr Ser Gly Ala Gln
145                 150                 155                 160
Gln Ala Thr Thr

<210> SEQ ID NO 3
<211> LENGTH: 755
<212> TYPE: DNA
<213> ORGANISM: Mus musculus
<220> FEATURE:
<221> NAME/KEY: CDS
<222> LOCATION: (1)...(489)

<400> SEQUENCE: 3
```

| | | | | | | | | | | | | | | | | |
|---|---|---|---|---|---|---|---|---|---|---|---|---|---|---|---|---|
| atg | atc | ttc | cac | aca | gga | aca | acg | aag | cct | acc | ctg | gtg | ctg | ctt | tgc | 48 |
| Met | Ile | Phe | His | Thr | Gly | Thr | Thr | Lys | Pro | Thr | Leu | Val | Leu | Leu | Cys | |
| 1 | | | | 5 | | | | | 10 | | | | | 15 | | |
| tgt | ata | gga | acc | tgg | ctg | gcc | acc | tgc | agc | ttg | tcc | ttc | ggt | gcc | cca | 96 |
| Cys | Ile | Gly | Thr | Trp | Leu | Ala | Thr | Cys | Ser | Leu | Ser | Phe | Gly | Ala | Pro | |
| | | 20 | | | | | 25 | | | | | 30 | | | | |
| ata | tcg | aag | gaa | gac | tta | aga | act | aca | att | gac | ctc | ttg | aaa | caa | gag | 144 |
| Ile | Ser | Lys | Glu | Asp | Leu | Arg | Thr | Thr | Ile | Asp | Leu | Leu | Lys | Gln | Glu | |
| | 35 | | | | | 40 | | | | | 45 | | | | | |
| tct | cag | gat | ctt | tat | aac | aac | tat | agc | ata | aag | cag | gca | tct | ggg | atg | 192 |
| Ser | Gln | Asp | Leu | Tyr | Asn | Asn | Tyr | Ser | Ile | Lys | Gln | Ala | Ser | Gly | Met | |
| 50 | | | | | 55 | | | | | 60 | | | | | | |
| tca | gca | gac | gaa | tca | ata | cag | ctg | ccg | tgt | ttc | agc | ctg | gac | cgg | gaa | 240 |
| Ser | Ala | Asp | Glu | Ser | Ile | Gln | Leu | Pro | Cys | Phe | Ser | Leu | Asp | Arg | Glu | |
| 65 | | | | 70 | | | | | 75 | | | | | 80 | | |
| gca | tta | acc | aac | atc | tcg | gtc | atc | ata | gca | cat | ctg | gag | aaa | gtc | aaa | 288 |
| Ala | Leu | Thr | Asn | Ile | Ser | Val | Ile | Ile | Ala | His | Leu | Glu | Lys | Val | Lys | |
| | | | | 85 | | | | | 90 | | | | | 95 | | |
| gtg | ttg | agc | gag | aac | aca | gta | gat | act | tct | tgg | gtg | ata | aga | tgg | cta | 336 |
| Val | Leu | Ser | Glu | Asn | Thr | Val | Asp | Thr | Ser | Trp | Val | Ile | Arg | Trp | Leu | |
| | | | 100 | | | | | 105 | | | | | 110 | | | |
| aca | aac | atc | agc | tgt | ttc | aac | cca | ctg | aat | tta | aac | att | tct | gtg | cct | 384 |
| Thr | Asn | Ile | Ser | Cys | Phe | Asn | Pro | Leu | Asn | Leu | Asn | Ile | Ser | Val | Pro | |
| | | 115 | | | | | 120 | | | | | 125 | | | | |
| gga | aat | act | gat | gaa | tcc | tat | gat | tgt | aaa | gtg | ttc | gtg | ctt | acg | gtt | 432 |
| Gly | Asn | Thr | Asp | Glu | Ser | Tyr | Asp | Cys | Lys | Val | Phe | Val | Leu | Thr | Val | |
| | 130 | | | | | 135 | | | | | 140 | | | | | |
| tta | aag | cag | ttc | tca | aac | tgc | atg | gca | gaa | ctg | cag | gct | aag | gac | aat | 480 |
| Leu | Lys | Gln | Phe | Ser | Asn | Cys | Met | Ala | Glu | Leu | Gln | Ala | Lys | Asp | Asn | |
| 145 | | | | | 150 | | | | | 155 | | | | | 160 | |

```
act aca tgc tgagtgatgg ggggggggg ggtgcagtgt cctcagcagt           529
Thr Thr Cys gcctgtcctt cgagggctga gcttgcaacc caggacttaa ctccaaaggg actgtgcggt    589
cattactagt catgttattt atgtttttat tttgtccact gaaatcttgt tctgctaccc    649
tgtagggact ggaagtggca gctatattta tttatttatg tactgagttt gttaacgctc    709
catggaggag ccttcagagt ctatttaata aattatattg acatga                   755

<210> SEQ ID NO 4
<211> LENGTH: 163
```

<212> TYPE: PRT
<213> ORGANISM: Mus musculus

<400> SEQUENCE: 4

```
Met Ile Phe His Thr Gly Thr Thr Lys Pro Thr Leu Val Leu Leu Cys
 1               5                  10                  15

Cys Ile Gly Thr Trp Leu Ala Thr Cys Ser Leu Ser Phe Gly Ala Pro
            20                  25                  30

Ile Ser Lys Glu Asp Leu Arg Thr Ile Asp Leu Leu Lys Gln Glu
        35                  40                  45

Ser Gln Asp Leu Tyr Asn Asn Tyr Ser Ile Lys Gln Ala Ser Gly Met
 50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ala His Leu Glu Lys Val Lys
            85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
            115                 120                 125

Gly Asn Thr Asp Glu Ser Tyr Asp Cys Lys Val Phe Val Leu Thr Val
 130                 135                 140

Leu Lys Gln Phe Ser Asn Cys Met Ala Glu Leu Gln Ala Lys Asp Asn
 145                 150                 155                 160

Thr Thr Cys
```

<210> SEQ ID NO 5
<211> LENGTH: 662
<212> TYPE: PRT
<213> ORGANISM: Homo sapiens

<400> SEQUENCE: 5

```
Met Lys Leu Ser Pro Gln Pro Ser Cys Val Asn Leu Gly Met Met Trp
 1               5                  10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
 50                  55                  60

Gln Tyr Thr Val Lys Arg Thr Tyr Ala Phe Gly Glu Lys His Asp Asn
 65                  70                  75                  80

Cys Thr Thr Asn Ser Ser Thr Ser Glu Asn Arg Ala Ser Cys Ser Phe
            85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
            115                 120                 125

Leu Glu Asn Ile Ala Lys Thr Glu Pro Pro Lys Ile Phe Arg Val Lys
 130                 135                 140

Pro Val Leu Gly Ile Lys Arg Met Ile Gln Ile Glu Trp Ile Lys Pro
 145                 150                 155                 160

Glu Leu Ala Pro Val Ser Ser Asp Leu Lys Tyr Thr Leu Arg Phe Arg
            165                 170                 175

Thr Val Asn Ser Thr Ser Trp Met Glu Val Asn Phe Ala Lys Asn Arg
            180                 185                 190
```

```
Lys Asp Lys Asn Gln Thr Tyr Asn Leu Thr Gly Leu Gln Pro Phe Thr
            195                 200                 205

Glu Tyr Val Ile Ala Leu Arg Cys Ala Val Lys Glu Ser Lys Phe Trp
    210                 215                 220

Ser Asp Trp Ser Gln Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
        290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
                340                 345                 350

Gln Leu Val Val Lys Trp Gln Ser Ser Ala Leu Asp Val Asn Thr Trp
            355                 360                 365

Met Ile Glu Trp Phe Pro Asp Val Asp Ser Glu Pro Thr Thr Leu Ser
        370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
```

```
                        610                 615                 620
Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660

<210> SEQ ID NO 6
<211> LENGTH: 979
<212> TYPE: PRT
<213> ORGANISM: Homo sapiens

<400> SEQUENCE: 6

Met Ala Leu Phe Ala Val Phe Gln Thr Thr Phe Phe Leu Thr Leu Leu
1               5                  10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
```

```
                        325                 330                 335
Phe Ser Val Asn Phe Glu Asn Val Asn Ala Thr Asn Ala Ile Met Thr
                340                 345                 350
Trp Lys Val His Ser Ile Arg Asn Asn Phe Thr Tyr Leu Cys Gln Ile
            355                 360                 365
Glu Leu His Gly Glu Gly Lys Met Met Gln Tyr Asn Val Ser Ile Lys
        370                 375                 380
Val Asn Gly Glu Tyr Phe Leu Ser Glu Leu Pro Ala Thr Glu Tyr
385                 390                 395                 400
Met Ala Arg Val Arg Cys Ala Asp Ala Ser His Phe Trp Lys Trp Ser
                405                 410                 415
Glu Trp Ser Gly Gln Asn Phe Thr Thr Leu Glu Ala Ala Pro Ser Glu
                420                 425                 430
Ala Pro Asp Val Trp Arg Ile Val Ser Leu Glu Pro Gly Asn His Thr
                435                 440                 445
Val Thr Leu Phe Trp Lys Pro Leu Ser Lys Leu His Ala Asn Gly Lys
            450                 455                 460
Ile Leu Phe Tyr Asn Val Val Glu Asn Leu Asp Lys Pro Ser Ser
465                 470                 475                 480
Ser Glu Leu His Ser Ile Pro Ala Pro Ala Asn Ser Thr Lys Leu Ile
                485                 490                 495
Leu Asp Arg Cys Ser Tyr Gln Ile Cys Val Ile Ala Asn Asn Ser Val
                500                 505                 510
Gly Ala Ser Pro Ala Ser Val Ile Val Ile Ser Ala Asp Pro Glu Asn
            515                 520                 525
Lys Glu Val Glu Glu Glu Arg Ile Ala Gly Thr Glu Gly Gly Phe Ser
        530                 535                 540
Leu Ser Trp Lys Pro Gln Pro Gly Asp Val Ile Gly Tyr Val Val Asp
545                 550                 555                 560
Trp Cys Asp His Thr Gln Asp Val Leu Gly Asp Phe Gln Trp Lys Asn
                565                 570                 575
Val Gly Pro Asn Thr Thr Ser Thr Val Ile Ser Thr Asp Ala Phe Arg
            580                 585                 590
Pro Gly Val Arg Tyr Asp Phe Arg Ile Tyr Gly Leu Ser Thr Lys Arg
            595                 600                 605
Ile Ala Cys Leu Leu Glu Lys Lys Thr Gly Tyr Ser Gln Glu Leu Ala
        610                 615                 620
Pro Ser Asp Asn Pro His Val Leu Val Asp Thr Leu Thr Ser His Ser
625                 630                 635                 640
Phe Thr Leu Ser Trp Lys Asp Tyr Ser Thr Glu Ser Gln Pro Gly Phe
                645                 650                 655
Ile Gln Gly Tyr His Val Tyr Leu Lys Ser Lys Ala Arg Gln Cys His
                660                 665                 670
Pro Arg Phe Glu Lys Ala Val Leu Ser Asp Gly Ser Glu Cys Cys Lys
            675                 680                 685
Tyr Lys Ile Asp Asn Pro Glu Glu Lys Ala Leu Ile Val Asp Asn Leu
        690                 695                 700
Lys Pro Glu Ser Phe Tyr Glu Phe Phe Ile Thr Pro Phe Thr Ser Ala
705                 710                 715                 720
Gly Glu Gly Pro Ser Ala Thr Phe Thr Lys Val Thr Thr Pro Asp Glu
                725                 730                 735
His Ser Ser Met Leu Ile His Ile Leu Leu Pro Met Val Phe Cys Val
                740                 745                 750
```

```
Leu Leu Ile Met Val Met Cys Tyr Leu Lys Ser Gln Trp Ile Lys Glu
        755                 760                 765

Thr Cys Tyr Pro Asp Ile Pro Asp Pro Tyr Lys Ser Ser Ile Leu Ser
        770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
                820                 825                 830

Thr Lys Pro Asn Tyr Leu Tyr Leu Leu Pro Thr Glu Lys Asn His Ser
                835                 840                 845

Gly Pro Gly Pro Cys Ile Cys Phe Glu Asn Leu Thr Tyr Asn Gln Ala
        850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
                900                 905                 910

Thr Ser Leu Asn Tyr Val Ser Gln Leu Ala Ser Pro Met Phe Gly Asp
                915                 920                 925

Lys Asp Ser Leu Pro Thr Asn Pro Val Glu Ala Pro His Cys Ser Glu
        930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys

<210> SEQ ID NO 7
<211> LENGTH: 6
<212> TYPE: PRT
<213> ORGANISM: Artificial Sequence
<220> FEATURE:
<223> OTHER INFORMATION: Glu-Glu tag peptide

<400> SEQUENCE: 7

Glu Tyr Met Pro Met Glu
 1               5
```

METHODS OF USING IL-31 MONOCLONAL ANTIBODIES TO REDUCE INFLAMMATION

This application is a divisional of U.S. application Ser. No. 11/430,066, filed May 8, 2006 now U.S. Pat. No. 7,531,637, which claims the benefit of U.S. Provisional Application Ser. No. 60/678,918, filed May 6, 2005, U.S. Provisional Application Ser. No. 60/696,251, filed Jul. 1, 2005, and U.S. Provisional Application Ser. No. 60/711,600, filed Aug. 26, 2005, all of which are herein incorporated by reference.

BACKGROUND OF THE INVENTION

The immune system hosts a wide range of specific cell types including lymphocytes. Lymphocytes determine the specificity of immune reaction in a host and include two classes, the B lymphocytes, which are precursors of antibody producing cells and the T lymphocytes, which are required for certain regulatory functions such as the development of specific immune responses.

Mature T cells may be activated, i.e., by an antigen or other stimulus, to produce, for example, cytokines, biochemical signaling molecules, or receptors that further influence the fate of the T cell population.

B cells can be activated via receptors on their cell surface including B cell receptor and other accessory molecules to perform accessory cell functions, such as production of cytokines.

Monocytes/macrophages and T-cells can be activated by receptors on their cell surface and play a central role in the immune response by presenting antigen to lymphocytes and also act as accessory cells to lymphocytes by secreting numerous cytokines.

Natural killer (NK) cells have a common progenitor cell with T cells and B cells, and play a role in immune surveillance. NK cells, which comprise up to 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells without activation.

The interleukins are a family of cytokines that mediate immunological responses, including inflammation. The interleukins mediate a variety of inflammatory pathologies. Central to an immune response are T cells, which produce many cytokines and adaptive immunity to antigens. Cytokines produced by T cells have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

The skin plays an important role in the immune system and consists of layers. The epidermis is a surface layer. Underneath the epidermis is the dermis, a layer of connective tissue. Underneath the dermis, is the hypodermis, a layer of large amounts of adipose tissue. Circulating T lymphocytes migrate to the skin under normal and inflammatory conditions. The cutaneous lymphocyte antigen (CLA) is considered a homing receptor for T cells with tropism for the skin. Santamaria-Babi, L., *Eur. J. Dermatol* 14:13-18, 2004.

Several diseases of the skin are known to express high levels of CLA+ T cells, including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. There is a need to treat such skin T cell mediated diseases.

The demonstrated in vivo activities of the cytokine family illustrate the enormous clinical potential of, and need for, other cytokines, cytokine agonists, and cytokine antagonists. IL-31, a newly identified cytokine. IL-31, when over-expressed in mice, results in dermatitis-like symptoms. Both skin-homing T cells and epidermal kerationcytes have been implicated in the pathology of skin diseases in humans. The present invention addresses these needs by providing antagonists to pro-inflammatory cytokine IL-31. Such antagonists of the present invention, which may block, inhibit, reduce, antagonize or neutralize the activity of IL-31, include soluble IL-31RA receptors and neutralizing anti-IL-31 antibodies. The invention further provides uses therefor in inflammatory disease, as well as related compositions and methods.

DETAILED DESCRIPTION OF THE INVENTION

Prior to setting forth the invention in detail, it may be helpful to the understanding thereof to define the following terms:

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and $(Fab')_2$, as well as diabodies, linear antibodies, multivalent or multispecific hybrid antibodies (as described above and in detail in: Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a $F(ab')_2$ molecule.

A "$F(ab')_2$ fragment" contains two light chains and two heavy chains containing a portion of the constant region between the $C_{H1}$ and $C_{H2}$ domains, such that an interchain disulfide bond is formed between two heavy chains.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to 110%.

All references cited herein are incorporated by reference in their entirety.

The present invention is based in part upon the discovery of the use of antibodies as antagonists to IL-31 thereby inhibiting inflammation in general, and the symptoms of dermatitis and pruritic diseases. The invention provides the use of monoclonal antibodies to inhibit, reduce, prevent or minimize the effects of dermatitis and pruritic diseases as further described herein. In an embodiment, the dermatitis is atopic dermatitis. In another embodiment the dermatitis is prurigo nodularis. In another embodiment, the dermatitis is eczema. IL-31 is a newly discovered T cell cytokine which, when over-expressed in mice, results in dermatitis-like symptoms. See also, Dillon, et al., Nature Immunol. 5:752-760, 2004. Both skin-homing T cells and epidermal kerationcytes have been implicated in the pathology of skin diseases in humans. IL-31 mRNA and protein expression is restricted to the skin-homing CLA+ T cell population in both atopic dermatitis (AD) patients and normal individuals, while analysis of the receptor for IL-31, IL-31RA, by immunohistochemistry (IHC) suggests slightly higher levels of IL-31RA expression on skin keratinocytes in skin biopsies from acute and chronic AD sufferers compared to normal individuals.

IL-31 is the HUGO name for a cytokine that has been previously described as Zcyto17rlig in a published U.S. patent application (See publication number 20030224487, Sprecher, Cindy et al., 2003, incorporated herein by reference). See also, Dillon, et al., Nature Immunol., supra. The heterodimeric receptor for IL-31 was also described in 20030224487 as zcytor17 (HUGO name, IL-31RA) which forms a heterodimer with OncostatinM receptor beta (OSMRbeta). IL-31 was isolated from a cDNA library generated from activated human peripheral blood cells (hPBCs), which were selected for CD3. CD3 is a cell surface marker unique to cells of lymphoid origin, particularly T cells. The polynucleotide and polypeptide sequences for human IL-31 are shown in SEQ ID NOs: 1 and 2, respectively. The polynucleotide and polypeptide sequences for murine IL-31 are shown in SEQ ID NOs: 10 and 11, respectively. As used herein the term, IL-31 means IL-31 as used in U.S. patent publication number 20030224487, as shown above. The secretory signal sequence of IL-31 is comprised of amino acid residues 1 (Met) to 23 (Ala), and the mature polypeptide is comprised of amino acid residues 24 (Ser) to 164 (Thr) (as shown in SEQ ID NO:2). Further N-terminal sequencing analysis of purified IL-31 from 293T cells showed an N-terminus at residue 27 (Leu) as shown in SEQ ID NO:2, with the mature polypeptide comprised of amino acid residues 27 (Leu) to 164 (Thr) (as shown in SEQ ID NO:2).

The polypeptide sequence for the IL-31RA (IL-31 receptor) is shown in SEQ ID NO:5, and the polypeptide sequence for OncostatinM receptor beta (OSMRbeta) is shown in SEQ ID NO:7.

The IL-31RA and OSMRbeta receptors belong to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in *Cytokine* 5(2): 95-106, 1993). The IL-31RA subunit is fully described in commonly-owned PCT Patent Application No. US01/20484 (WIPO publication No. WO 02/00721). Analysis of the tissue distribution of the mRNA of the IL-31RA subunit revealed expression in activated CD4+ and CD8+ T-cell subsets, CD14+ monocytes, and weaker expression in CD19+ B-cells. Moreover, the mRNA was present in both resting or activated monocytic cell lines THP-1 (ATCC No. TIB-202), U937 (ATCC No. CRL-1593.2) and HL60 (ATCC No. CCL-240).

Inhibition, neutralization, blocking signal transduction by the IL-31 antagonists described herein can be measured by a number of assays known to one skilled in the art. For example, assays measuring a reduction in proliferation include assays for reduction of a dye such as AlamarBlue™ (AccuMed International, Inc. Westlake, Ohio), 3-(4,5-dimethylthiazol-2-yl)-2,5-diphenyl tetrazolium bromide (Mosman, *J. Immunol. Meth.* 65: 55-63, 1983); 3,(4,5 dimethyl thiazol-2yl)-5-3-carboxymethoxyphenyl-2H-tetrazolium; 2,3-bis(2-methoxy-4-nitro-5-sulfophenyl)-5-[(phenylamino) carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, naphthalene black or trypan blue; dye uptake using diacetyl fluorescein; and chromium release. See, in general, Freshney, *Culture of Animal Cells: A Manual of Basic Technique,* 3rd ed., Wiley-Liss, 1994, which is incorporated herein by reference. In addition to the above, see published U.S. patent publication number 20030224487, (Sprecher, Cindy et al., 2003) for an example of BaF3 cells expressing IL-31RA and full-length OSMR-beta.

In general, cytokines are predicted to have a four-alpha helix structure, with helices A, C and D being most important in ligand-receptor interactions, and are more highly conserved among members of the family. Referring to the human IL-31 amino acid sequence shown in SEQ ID NO:2, alignment of human IL-31, human IL-3, and human cytokine amino acid sequences it is predicted that IL-31 helix A is defined by amino acid residues 38-52; helix B by amino acid residues 83-98; helix C by amino acid residues 104-117; and helix D by amino acid residues 137-152; as shown in SEQ ID NO:2. Structural analysis suggests that the A/B loop is long, the B/C loop is short and the C/D loop is long. This loop structure results in an up-up-down-down helical organization. Based on 4-helix bundle structure, the cysteine residues within IL-31 that are conserved correspond to amino acid residues 72, 133, and 147 of SEQ ID NO:2; and 74, 137, and 151 of SEQ ID NO:11 described herein. Consistent cysteine placement is further confirmation of the four-helical-bundle structure. Also highly conserved in the IL-31 is the Glu residue as shown in SEQ ID NO:2 at residue 43. These helices of IL-31 may be specific targets for inhibition, reduction or neutralization by the antibodies described herein for blocking the effects of IL-31 signaling through its cognate receptor.

Based on comparison between sequences of human and murine IL-31 conserved residues were found in the regions predicted to encode alpha helices C and D. The corresponding polynucleotides encoding the human IL-31 polypeptide regions, domains, motifs, residues and sequences described herein are as shown in SEQ ID NO:1. These helices of IL-31 may be specific targets for inhibition, reduction or neutralization by the antibodies described herein for blocking the effects of IL-31 signaling through its cognate receptor.

While helix D is relatively conserved between human and murine IL-31, helix C is the most conserved. While both species have predominant acidic amino acids in this region, the differences may account for species specificity in interaction between IL-31 and its receptor, IL-31RA comprising monomeric, heterodimeric or multimeric receptors. Loop A/B and helix B of IL-31 are marginally conserved, and helix C through Loop C/D into helix D is most conserved between species; conservation through this region suggests that it is functionally significant. The D helices of human and murine IL-31 are also conserved. IL-31RA receptor antagonists may be designed through mutations within IL-31 helix D. These may include truncation of the protein from residue Thr156 (SEQ ID NO:2), or conservation of residues that confer binding of the ligand to the receptor, but diminish signaling activity.

Methods for preparing the polynucleotides encoding the antibodies described herein (including DNA and RNA) are well known in the art. Total RNA can be prepared using guanidinium isothiocyanate extraction followed by isolation by centrifugation in a CsCl gradient (Chirgwin et al., *Biochemistry* 18:52-94, 1979). Poly (A)+ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding IL-31 antibodies are then identified and isolated by, for example, hybridization or PCR.

The polynucleotide sequence for the mouse ortholog of IL-31 has been identified and is shown in SEQ ID NO:3 Mature sequence for the mouse IL-31 putatively begins at Met$_1$, as shown in SEQ ID NO:4, which corresponds to Met$_1$, as shown in SEQ ID NO:2, in the human sequence. Tissue analysis revealed that expression of mouse IL-31 is found in testis, brain, CD90+ cells, prostate cells, salivary gland and skin. Further N-terminal sequencing analysis of purified IL-31 from 293T cells showed an N-terminus at residue 31 (Ala) as shown in SEQ ID NO:4, with the mature polypeptide comprised of amino acid residues 31 (Ala) to 163 (Cys) (as shown in SEQ ID NO: 4).

A Hopp/Woods hydrophilicity profile of the IL-31 protein sequence as shown in SEQ ID NO:2 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in human IL-31, hydrophilic regions include amino acid residues 54-59 of SEQ ID NO:2, amino acid residues 129-134 of SEQ ID NO:2, amino acid residues 53-58 of SEQ ID NO:2, amino acid residues 35-40 of SEQ ID NO:2, and amino acid residues 33-38 of SEQ ID NO:2. For example, in mouse IL-31, hydrophilic regions include amino acid residues 34-39 of SEQ ID NO:11, amino acid residues 46-51 of SEQ ID NO:11, amino acid residues 131-136 of SEQ ID NO:11, amino acid residues 158-163 of SEQ ID NO:11, and amino acid residues 157-162 of SEQ ID NO:11.

Those skilled in the art will recognize that hydrophilicity or hydrophobicity will be taken into account when designing modifications in the amino acid sequence of a IL-31 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include Val, Leu and Ile or the group consisting of Met, Gly, Ser, Ala, Tyr and Trp residues as shown in SEQ ID NO:2. Conserved cysteine residues at positions within SEQ ID NO:2 and SEQ ID NO:11, will be relatively intolerant of substitution.

The present invention also includes antibodies that bind functional fragments of IL-31 polypeptides and nucleic acid molecules encoding such functional fragments. A "functional" IL-31 or fragment thereof as defined herein is characterized by its proliferative or differentiating activity, by its ability to induce or inhibit specialized cell functions, or by its ability to bind specifically to an anti-IL-31 antibody or IL-31RA or antibody or IL-31RA/OSMRbeta heterodimers of these receptors (either soluble or immobilized). As previously described herein, IL-31 is characterized by a four-helical-bundle structure comprising helix A (amino acid residues 38-52), helix B (amino acid residues 83-98), helix C (amino acid residues 104-117) and helix D (amino acid residues 137-152), as shown in SEQ ID NO:2. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another four-helical-bundle cytokine, such as IL-15, IL-2, IL-4 and GM-CSF, or by a non-native and/or an unrelated secretory signal peptide that facilitates secretion of the fusion protein.

The present invention also provides antibodies that bind to polypeptide fragments or peptides comprising an epitope-bearing portion of a IL-31 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)). The binding of the antibodies to these functional fragments results in inhibition, blocking, neutralization, and/or reduction in signal transduction of IL-31 on its cognate receptor.

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies (e.g., neutralizing antibodies) that bind with the polypeptides described herein. Hopp/Woods hydrophilicity profiles can be used to determine regions that have the most antigenic potential (Hopp et al., 1981, ibid. and Hopp, 1986, ibid.). For example, in human IL-31, hydrophilic regions include amino acid residues 54-59 of SEQ ID NO:2, amino acid residues 129-134 of SEQ ID NO:2, amino acid residues 53-58 of SEQ ID NO:2, amino acid residues 35-40 of SEQ ID NO:2, and amino acid residues 33-38 of SEQ ID NO:2. For example, in mouse IL-31, hydrophilic regions include amino acid residues 34-39 of SEQ ID NO:11, amino acid residues 46-51 of SEQ ID NO:11, amino acid residues 131-136 of SEQ ID NO:11, amino acid residues 158-163 of SEQ ID NO:11, and amino acid residues 157-162 of SEQ ID NO:11.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:4. Such epitope-bearing peptides and polypeptides can be produced by fragmenting a IL-31 polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering and Clinical Application*, Ritter and Ladyman (eds.), pages 60-84 (Cambridge University Press 1995), and Coligan et al. (eds.), *Current Protocols in Immunology, pages* 9.3.1-9.3.5 and pages 9.4.1-9.4.11 (John Wiley & Sons 1997).

The activity of the antibodies as described herein can be measured by their ability to inhibit, or reduce proliferation using a variety of assays that measure proliferation of and/or binding to cells expressing the IL-31RA receptor. Of particular interest are changes in IL-31-dependent cells. Suitable cell lines to be engineered to be IL-31-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., *Blood* 64: 786-790, 1984), and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today,* 8th Ann. Mtg. Int. Soc. Exp. Hematol. 1979, 145-156, 1980).

The activity of the anti-IL-31 antibodies described herein can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. et al., *Eur. J. Pharmacol.* 346:87-95, 1998.

Antagonists are also useful as research reagents for characterizing sites of ligand-receptor interaction. Antagonists are useful to inhibit expansion, proliferation, activation, and/or differentiation of cells involved in regulating hematopoiesis. Inhibitors of IL-31 activity (IL-31 antagonists) include anti-IL-31 antibodies and soluble IL-31 receptors, as well as other peptidic and non-peptidic agents (including ribozymes).

Inhibition the activity of IL-31 can be measured by a number of assays. In addition to those assays disclosed herein, samples can be tested for inhibition of IL-31 activity within a variety of assays designed to measure receptor binding, the stimulation/inhibition of IL-31-dependent cellular responses or proliferation of IL-31RA receptor-expressing cells.

A IL-31-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

IL-31 antibodies can be used to block the biological action of pro-inflammatory IL-31 and are useful as anti-inflammatory therapeutics in a variety of diseases as described herein. One of skill in the art would recognize that antigenic, epitope-bearing polypeptides contain a sequence of at least 6, preferably at least 9, and more preferably at least 15 to about 30 contiguous amino acid residues of a IL-31 polypeptide (e.g., SEQ ID NO:2). Polypeptides comprising a larger portion of a IL-31 polypeptide, i.e., from 30 to 100 residues up to the entire length of the amino acid sequence are included. Antigens or immunogenic epitopes can also include attached tags, adjuvants, vehicles and carriers, as described herein. Suitable antigens include the IL-31 polypeptide encoded by SEQ ID NO:2 from amino acid number 24 to amino acid number 164, or a contiguous 9 to 141 amino acid fragment thereof. Other suitable antigens include, the full length and the mature IL-31, helices A-D, and individual or multiple helices A, B, C, and D, of the IL-31 four-helical-bundle structure, as described herein. Preferred peptides to use as antigens are hydrophilic peptides such as those predicted by one of skill in the art from a hydrophobicity plot, as described herein, for example, amino acid residues 114-119, 101-105, 126-131, 113-118, and 158-162 of SEQ ID NO:2; and amino acid residues 34-39, 46-51, 131-136, 158-163 and 157-162 of SEQ ID NO:11. Moreover, IL-31 antigenic epitopes as predicted by a Jameson-Wolf plot, e.g., using DNASTAR Protean program (DNASTAR, Inc., Madison, Wis.) serve as preferred antigens, and are readily determined by one of skill in the art.

Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a IL-31 polypeptide or a fragment thereof. The immunogenicity of a IL-31 polypeptide may be increased through the use of an adjuvant, such as alum (aluminum hydroxide) or Freund's complete or incomplete adjuvant. Polypeptides useful for immunization also include fusion polypeptides, such as fusions of IL-31 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Antibodies are considered to be specifically binding if: 1) they exhibit a threshold level of binding activity, and 2) they do not significantly cross-react with related polypeptide molecules. A threshold level of binding is determined if anti-IL-31 antibodies herein bind to a IL-31 polypeptide, peptide or epitope with an affinity at least 10-fold greater than the binding affinity to control (non-IL-31) polypeptide. It is preferred that the antibodies exhibit a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-IL-31 antibodies do not significantly cross-react with related polypeptide molecules is shown, for example, by the antibody detecting IL-31 polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human IL-31, and IL-31 mutant polypeptides. Moreover, antibodies can be "screened against" known related polypeptides, to isolate a population that specifically binds to the IL-31 polypeptides. For example, antibodies raised to IL-31 are adsorbed to related polypeptides adhered to insoluble matrix; antibodies specific to IL-31 will flow through the matrix under the proper buffer conditions. Screening allows isolation of polyclonal and monoclonal antibodies non-cross-reactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol* 43: 1-98, 1988; *Monoclonal Antibodies: Principles and Practice*, Goding, J. W. (eds.), Academic Press Ltd., 1996; Benjamin et al., Ann. Rev. Immunol. 2: 67-101, 1984. Specifically binding anti-IL-31 antibodies can be detected by a number of methods in the art, and disclosed below.

Monoclonal antibodies can be prepared, for example, by immunizing Sprague-Dawley Rats (Charles River Laboratories, Wilmington, Mass.), with the purified mature recombinant human IL-31 polypeptide (amino acid residues 27 (Leu) to 167 (Thr) of SEQ ID NO:2) or the mouse ortholog, produced from the expression systems listed herein. The rats are each given an initial intraperitoneal (IP) injection of 100 µg of the purified human recombinant IL-31 protein in Complete Freund's Adjuvant (Pierce, Rockford, Ill.) followed by booster IP injections of 50 µg of the purified recombinant protein in Incomplete Freund's Adjuvant every two weeks. Seven to ten days after the administration of the third booster injection, the animals are bled and the serum is collected.

The human IL-31-specific rat sera samples are characterized by ELISA for titer to the specific antibody target biotinylated human IL-31.

Splenocytes and lymphatic node cells are harvested from 2 high-titer rats and fused to SP2/0 (mouse) myeloma cells using PEG 1500 in two separate fusion procedures (4:1 fusion ratio, splenocytes to myeloma cells, "Antibodies A Laboratory Manual, E. Harlow and D. Lane, Cold Spring Harbor Press). Following 10 days growth post-fusion, specific antibody-producing hybridoma pools are identified by ELISA. Hybridoma pools positive in both ELISA protocols are analyzed further for their ability to block or reduce the receptor binding activity ("neutralization assay") of purified recombinant IL-31.

Hybridoma pools yielding positive results by ELISA only or ELISA and the "neutralization assay" are cloned at least two times by limiting dilution.

Monoclonal antibodies purified from tissue culture media are characterized for their utility in an ELISA for the quantitative determination of recombinant and native human IL-31. The antibodies are selected and a quantitative assay is developed.

Monoclonal antibodies purified from tissue culture media are characterized for their ability to block or reduce the receptor binding activity ("neutralization assay") of purified recombinant huIL-31 on BaF3/MPL-IL-31 cells. A number of "neutralizing" monoclonal antibodies are identified in this manner. Hybridomas expressing the neutralizing monoclonal antibodies to human IL-31 described can then be deposited with the American Type Tissue Culture Collection (ATCC; Manassas Va.) patent depository as original deposits under the Budapest Treaty.

Monoclonal antibodies can be prepared by immunizing Lewis Rats (Rockland Immunochemicals, Gilbertsville, Pa.), with the cleaved and purified IL-31 recombinant fusion protein. The rats are each given an initial intraperitoneal (IP) injection of 100 µg of the purified recombinant fusion protein in Complete Freund's Adjuvant (Pierce, Rockford, Ill.) followed by booster IP injections of 50 µg of the purified recombinant protein in Incomplete Freund's Adjuvant every two weeks for four weeks. Following the first four weeks of immunizations, booster IP injections of 50 µg of the cleaved purified recombinant protein coupled to the carrier protein keyhole limpet hemocyanin (KLH, Pierce, Rockford, Ill.) in Incomplete Freund's are administered every two weeks for four weeks. Seven to ten days after the administration of the fourth booster injection, the animals are bled and the serum was collected. The IL-31-specific rat serum samples are characterized by ELISA using 500 ng/ml of the purified recombinant fusion protein IL-31-Fc as the specific antibody target and an unrelated fusion protein as a non-specific antibody target. Splenocytes are harvested from one or more high-titer rats and fused to SP2/0 (mouse) myeloma cells in an optimized PEG-mediated fusion protocol (Rockland Immunochemicals). Following 12 days growth post-fusion, specific antibody-producing hybridoma pools are identified by ELISA using 500 ng/ml each of the purified IL-31 recombinant fusion protein as the specific antibody target and an unrelated fusion protein as a non-specific antibody target. Hybridoma pools positive to the specific antibody target only are analyzed further for their ability to block or reduce the receptor binding activity ("neutralization assay") of recombinant huIL-31 on BaF3/MPL-IL-31 cells and an ability to bind via FACS analysis as antibody target. Hybridoma pools yielding a specific positive result in the ELISA assay and positive results in either the FACS or "neutralization assay" are cloned at least two times by limiting dilution.

Five rat anti-mouse hybridomas were generated in a similar fashion and were given the following clone designations: clone 271.9.4.2.6, clone 271.26.6.6.1, clone 271.33.1.2.2, clone 271.33.3.2.1, and clone 271.39.4.6.5. See Example 1. The monoclonal antibodies produced by these clones were characterized in a number of ways including binning (i.e., determining if each antibody could inhibit the binding of any other binding), relative affinity, and neutralization. The monoclonal antibodies appear to fall into two separate bins with clone 271.33.3.2.1 binding to a separate epitope than the other four. Relative binding affinity for four of these monoclonal antibodies is described in Example 14.

Binding affinity of the monoclonal antibodies can be generated. Goat-anti-Rat IgG-Fc gamma specific Antibody (Jackson) is immobilized onto a CM5 Biacore chip. The assay is optimized to bind each mAb onto the anti-Rat capture surface and then a concentration series of IL-31 is injected across the mAb to see association (Ka) and dissociation (Kd). After each run, the surface is regenerated back to the anti-Rat Antibody with 2 injections of 20 mM HCl. Data is generated for each and evaluation software (BIAevaluation software version 3.2, Pharmacia BIAcore, Uppsala, Sweden) is used to assess the kinetics of the anti-IL-31 antibody binding to the IL-31 protein Murine anti-human Il-31 mAbs can be generated as follows. Six to twelve week old IL-31 knockout mice are immunized by intraperitoneal injection with 25-50 ug of soluble human IL-31-muFc protein) mixed 1:1 (v:v) with Ribi adjuvant (Sigma) on a biweekly schedule. Seven to ten days following the third immunization, blood samples are taken via retroorbital bleed, the serum harvested and evaluated for its ability to inhibit the binding of IL-31 in neutralization assays (e.g., described herein) and to stain IL-31 transfected versus untransfected 293 cells in a FACS staining assay. Mice continued to be immunized and blood samples taken and evaluated as described above until neutralization titers reaches a plateau. At that time, mice with the highest neutralization titers are injected intravascularly with 25-50 ug of soluble IL-31-Fc protein in PBS. Three days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., J. Immunol. 123:1548-50, 1979; and Lane, R. D. J Immunol Methods 81:223-8, 1985).

Primary screening can be performed on the hybridoma supernatants at 8-10 days post-fusion for their ability to bind IL-31-muFc protein by ELISA using HRP-conjugated goat anti-mouse kappa and anti-lambda light chain second step reagents to identify bound mouse antibodies.

Biochemical confirmation that the target molecule, IL-31, recognized by the putative anti-IL-31 mAbs is indeed IL-31 are performed by standard immunoprecipitation followed by SDS-PAGE analysis or western blotting procedures, both employing soluble membrane preparations from IL-31 transfected versus untransfected Baf3 cells. The mAbs are tested for their ability to specifically immunoprecipitate or western blot the soluble IL-31-muFc protein.

Monoclonal antibodies purified from tissue culture media were characterized for their ability to block or inhibit the ability of IL-31 to bind to its receptor in a neutralization assay. Twenty "neutralizing" monoclonal antibodies were identified in this manner. Ten of these have been identified as "good neutralizers" after the first round cloning: clone 292.72.3, clone 292.118.6, clone 292.63.5, clone 292.64.6, clone 292.84.1, clone 292.109.4, clone 292.12.3, clone 292.51.5, clone 292.39.5, and clone 292.105.4. The other ten have the following clone designations after the first round of cloning: clone 294.35.2, clone 294.146.5, clone 292.152.4, clone 292.154.4, clone 294.154.5, clone 294.35.3, clone 291.78.4, clone 294.155.6, clone 294.158.5, clone 294.163.2, and clone 294.144.3.

The specified monoclonal antibodies were taken through a second round of cloning and, again, characterized for their ability to block or inhibit the ability of IL-31 to bind to its receptor in a neutralization assay. The clone designations after the second round of cloning for the "good neutralizers" are: clone 292.12.3.1, clone 292.63.5.3, clone 292.72.3.1, clone 292.84.1.6, clone 292.118.6.4, clone 292.64.6.5.5, clone 292.39.5.3, clone 292.51.5.2, clone 292.109.4.4, and clone 292.105.4.1. Six of the other ten have the following clone designations: clone 292.152.4.1, clone 294.158.5.2, clone 294.32.2.6.3, clone 294.144.3.5, clone 294.154.5.3, and clone 294.163.2.1.

Hybridomas expressing the neutralizing monoclonal antibodies to human IL-31 described above were deposited with the American Type Tissue Culture Collection (ATCC; Manassas Va.) patent depository as original deposits under the Budapest Treaty and were given the following ATCC Accession Nos.: clone 292.12.3.1 (ATCC Patent Deposit Designation PTA-6815); clone 292.72.3.1 (ATCC Patent Deposit Designation PTA-6816); clone 292.63.5.3 (ATCC Patent Deposit Designation PTA-6829); clone 292.118.6.4 (ATCC Patent Deposit Designation PTA-6830); clone 294.163.2.1 (ATCC Patent Deposit Designation PTA-6831); clone 292.84.1.6 (ATCC Patent Deposit Designation PTA-6871); clone 294.35.2.6.3 (ATCC Patent Deposit Designation PTA-6872); clone 294.154.5.6 ATCC Patent Deposit Designation PTA-6875); and clone 294.144.3.5 (ATCC Patent Deposit Designation PTA-6873).

A hybridoma expressing the neutralizing monoclonal antibodies to mouse IL-31 described herein was deposited with the American Type Tissue Culture Collection (ATCC; Manassas Va.) patent depository as an original deposit under the Budapest Treaty and was given the following ATCC Accession Nos.: clone 271.26.6.6.1 (ATCC Patent Deposit Designation PTA-6874)

The monoclonal antibodies produced by these hybridoma clones can be cultured in a growth medium of 90% Iscove's Modified Dulbecco's medium with 2 mM L-glutamine, 100 μg/mL penicillin, and 100 μg/mL streptomycin sulfate, and 10% Fetal Clone I Serum (Hyclone Laboratories). The clones can be propagated by starting cultures at $2 \times 10^5$ cells/ml and maintaining between $1 \times 10^5$ and $5 \times 10^5$ cell ml at 37° C. and 5-6% CO. Cells can be adapted to serum free conditions upon subsequent transfers. Cells that are frozen are stored in 90% serum, 10% DMSO and stored in vapor phase of liquid nitrogen freezer.

Monoclonal antibodies in tissue culture media are characterized for their ability to block, inhibit, prevent, or reduce receptor binding when grown in the presence of the purified recombinant proteins human IL-31. For example, the monoclonal antibodies produced by these clones were characterized in a number of ways including binning (i.e., determining if each antibody could inhibit the binding of any other binding), relative affinity, and neutralization. The ten good neutralizing antibodies appear to be in the same bin, with the other monoclonal antibodies grouping into three separate bins. In addition, eight of the good neutralizing antibodies are IgG1 isotype and the other two are IgG2a isotype Monoclonal antibodies from hybridoma supernatants were captured using goat anti murine Fc pAb and the apparent binding affinity (EC50) of biotinylated IL31 was measured. Under these assay conditions, the good neutralizers have the lowest and comparable EC50 values ~4 ng/mL Bt-IL31. The apparent affinity of the weak neutralizers spans a range from ~10 ng/mL to 236 ng/mL Bt-IL31.

Monoclonal antibodies generated by the methods described herein can be tested for neutralization by a variety of methods. For example the luciferase assay as described in published U.S. patent application (See publication number 20030224487, Sprecher, Cindy et al., 2003) can be used. In addition neutralization can be tested by measuring a decrease in the production of pro-inflammatory chemokines such as TARC and MDC from keratinocyte cultures in the presence of ligand and the monoclonal antibody. Neutralization can also be measured by the in vivo models described herein.

In one embodiment, the antibodies of the present invention are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, $C_{H1}$, $C_{H2}$, and $C_{H3}$ domains. Also included in the invention are antigen-binding fragments also comprising any combination of variable region(s) with a hinge region, $C_{H1}$, $C_{H2}$, and $C_{H3}$ domains.

In another embodiment, the antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

The present invention also includes genetically altered antibodies that are functionally equivalent to the above-described antibodies. Modified antibodies providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Antibodies of the present invention can be can be modified post-translationally (e.g., acetylation, and phosphorylation) or can be modified synthetically (e.g., the attachment of a labeling group).

The genetically altered antibodies also include chimeric antibodies that derived from the anti-IL-31 antibodies. The chimeric antibodies comprise a variable region derived from a mouse or rat and a constant region derived from a human so that the chimeric antibody has a longer half-life and is less immunogenic when administered to a human subject. The method of making chimeric antibodies is known in the art. The variable regions of these antibodies can be connected with a constant region of a human IgG to form the desired chimeric antibody.

The genetically altered anti-IL-31 antibodies used in the present invention include humanized version of the antibodies described herein. Humanized antibodies comprise CDRs of a mouse donor immunoglobulin and heavy chain and light chain frameworks of a human acceptor immunoglobulin. The method of making humanized antibody is disclosed in U.S. Pat. Nos. 5,301,101; 5,585,089; 5,693,762; and 6,180,370 (each of which is incorporated by reference in its entirety). The CDRs of these antibodies can then be grafted to any selected human frameworks, which are known in the art, to generate the desired humanized antibody.

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and FIGS. Antibodies that specifically bind any epitope or polypeptide of the present invention may also be excluded. Therefore, the present invention includes antibodies that specifically bind polypeptides of the present invention, and allows for the exclusion of the same.

The invention also provides antibodies that competitively inhibit the binding of a monoclonal antibody to a polypeptide of the invention, preferably the polypeptide of SEQ ID NO:2 or SEQ ID NO: 4. Competitive inhibition can be determined by any method known in the art, for example, using the competitive binding assays described herein. In preferred embodiments, the antibody competitively inhibits the binding of a monoclonal antibody of the invention by at least 90%, at least 80%, at least 70%, at least 60%, or at least 50% to the polypeptide of SEQ ID NO:2 or SEQ ID NO: 4.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

The antibodies of the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention also encompass antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered.

Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

It is understood that the humanized antibodies designed by the present method may have additional conservative amino acid substitutions which have substantially no effect on antigen binding or other immunoglobulin functions. By conservative substitutions is intended combinations such as gly, ala; val, ile, leu; asp, glu; asn, gln; ser, thr; lys, arg; and phe, tyr.

Methods for humanizing non-human antibodies are well known in the art. Generally, humanized immunoglobulins, including humanized antibodies, have been constructed by means of genetic engineering. Most humanized immunoglobulins that have been previously described (Jones et al., op. cit.; Verhoeyen et al., op. cit.; Riechmann et al., op. cit.) have comprised a framework that is identical to the framework of a particular human immunoglobulin chain, the acceptor, and three CDR's from a non-human donor immunoglobulin chain. Specifically, humanized antibodies are antibody molecules from non-human species antibody that binds the desired antigen having one or more complementarity determining regions (CDRs) from the non-human species and framework regions from a human immunoglobulin molecule.

The present invention includes criteria by which a limited number of amino acids in the framework of a humanized immunoglobulin chain are chosen to be the same as the amino acids at those positions in the donor rather than in the acceptor, in order to increase the affinity of an antibody comprising the humanized immunoglobulin chain.

The antibodies of the present invention are generated based in part on the model that two contributing causes of the loss of affinity in prior means of producing humanized antibodies (using as examples mouse antibodies as the source of CDR's) are:

(1) When the mouse CDR's are combined with the human framework, the amino acids in the framework close to the CDR's become human instead of mouse. Without intending to be bound by theory, these changed amino acids may slightly distort the CDR's, because they create different electrostatic or hydrophobic forces than in the donor mouse antibody, and the distorted CDR's may not make as effective contacts with the antigen as the CDR's did in the donor antibody; and (2) Amino acids in the original mouse antibody that are close to, but not part of, the CDR's (i.e., still part of the framework), may make contacts with the antigen that contribute to affinity. These amino acids are lost when the antibody is humanized, because all framework amino acids are made human.

To avoid these problems, and to produce humanized antibodies that have a very strong affinity for a desired antigen, the present invention uses one or more of the following principles for designing humanized immunoglobulins. Also, the criteria may be used singly, or when necessary in combination, to achieve the desired affinity or other characteristics.

A principle is that as acceptor, a framework is used from a particular human immunoglobulin that is unusually homologous to the donor immunoglobulin to be humanized, or use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing as the acceptor immunoglobulin one of the human heavy (respectively light) chain variable regions that is most homologous to the heavy (respectively light) chain variable region of the donor immunoglobulin, fewer amino acids will be changed in going from the donor immunoglobulin to the humanized immunoglobulin. Hence, and again without intending to be bound by theory, it is believed that there is a smaller chance of changing an amino acid near the CDR's that distorts their conformation. Moreover, the precise overall shape of a humanized antibody comprising the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains will be chosen as acceptor to provide the heavy chain framework, and similarly for the light chain. Preferably, one of the 1-3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. In this case, the donor light and heavy chains will be compared only against chains from human antibodies whose complete sequence is known, e.g., the Eu, Lay, Pom, Wol, Sie, Gal, Ou and WEA antibodies (Kabat et al., op. cit.; occasionally, the last few amino acids of a human chain are not known and must be deduced by homology to other human antibodies). The human antibody will be chosen in which the light and heavy chain variable regions sequences, taken together, are overall most homologous to the donor light and heavy chain variable region sequences. Sometimes greater weight will be given to the heavy chain sequence. The chosen human antibody will then provide both light and heavy chain acceptor sequences. In practice, it is often found that the human Eu antibody will serve this role.

According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 (1993); Chothia et al., J. Mol. Biol., 196: 901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 151: 2623 (1993)).

Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor. Often, framework residues in the human framework regions will be substituted with the corresponding residue from the CDR donor antibody to alter, preferably improve, antigen binding.

These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Accordingly, such "humanized" antibodies are chimeric antibodies (U.S. Pat. No. 4,816,567) wherein substantially less than an intact human variable domain has been substituted by the corresponding sequence from a non-human species.

A second principle is that the following categories define what amino acids may be selected from the donor. Preferably, at many or all amino acid positions in one of these categories, the donor amino acid will in fact be selected.

Category 1: The amino acid position is in a CDR is defined by Kabat et al., op. cit.

Category 2: If an amino acid in the framework of the human acceptor immunoglobulin is unusual (i.e., "rare", which as used herein indicates an amino acid occurring at that position in less than about 20% but usually less than about 10% of human heavy (respectively light) chain V region sequences in a representative data bank), and if the donor amino acid at that position is typical for human sequences (i.e., "common", which as used herein indicates an amino acid occurring in more than about 25% but usually more than about 50% of sequences in a representative data bank), then the donor amino acid rather than the acceptor may be selected. This criterion helps ensure that an atypical amino acid in the human framework does not disrupt the antibody structure. Moreover, by replacing an unusual amino acid with an amino acid from the donor antibody that happens to be typical for human antibodies, the humanized antibody may be made less immunogenic. All human light and heavy chain variable region sequences are respectively grouped into "subgroups" of sequences that are especially homologous to each other and have the same amino acids at certain critical positions (Kabat et al., op. cit.). When deciding whether an amino acid in a human acceptor sequence is "rare" or "common" among human sequences, it will often be preferable to consider only those human sequences in the same subgroup as the acceptor sequence.

Category 3: In the positions immediately adjacent to one or more of the 3 CDR's in the primary sequence of the humanized immunoglobulin chain, the donor amino acid(s) rather than acceptor amino acid may be selected. These amino acids are particularly likely to interact with the amino acids in the CDR's and, if chosen from the acceptor, to distort the donor CDR's and reduce affinity. Moreover, the adjacent amino acids may interact directly with the antigen (Amit et al., Science, 233, 747-753 (1986), which is incorporated herein by reference) and selecting these amino acids from the donor may be desirable to keep all the antigen contacts that provide affinity in the original antibody.

Category 4: A 3-dimensional model, typically of the original donor antibody, shows that certain amino acids outside of the CDR's are close to the CDR's and have a good probability of interacting with amino acids in the CDR's by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units of some atom in the CDR's and must contain an atom that could interact with the CDR atoms according to established chemical forces, such as those listed above.

In the case of atoms that may form a hydrogen bond, the 3 angstroms is measured between their nuclei, but for atoms that do not form a bond, the 3 angstroms is measured between their Van der Waals surfaces. Hence, in the latter case, the nuclei must be within about 6 angstroms (3+sum of the Van der Waals radii) for the atoms to be considered capable of interacting. In many cases the nuclei will be from 4 or 5 to 6 .ANG. apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids in the framework that are capable of interacting with amino acids in the CDR's, and which therefore belong to Category 4, may be distinguished in another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a 3-dimensional model of an antibody, using algorithms known in the art (e.g., Connolly, J. Appl. Cryst. 16, 548 (1983) and Lee and Richards, J. Mol. Biol. 55, 379 (1971), both of which are incorporated herein by reference). Framework amino acids may also occasionally interact with the CDR's indirectly, by affecting the conformation of another framework amino acid that in turn contacts the CDR's.

The amino acids at several positions in the framework are known to be capable of interacting with the CDRs in many antibodies (Chothia and Lesk, J. Mol. Biol. 196, 901 (1987), Chothia et al., Nature 342, 877 (1989), and Tramontano et al., J. Mol. Biol. 215, 175 (1990), all of which are incorporated herein by reference), notably at positions 2, 48, 64 and 71 of the light chain and 26-30, 71 and 94 of the heavy chain (numbering according to Kabat, op. cit.), and therefore these amino acids will generally be in Category 4. Typically, humanized immunoglobulins, of the present invention will include donor amino acids (where different) in category 4 in addition to these. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain positions that may be in Category 4 such as the first 5 amino acids of the light chain may sometimes be chosen from the acceptor immunoglobulin without loss of affinity in the humanized immunoglobulin. Chothia and Lesk (op. cit.) define the CDRs differently from Kabat et al. (op. cit.). Notably, CDR1 is defined as including residues 26-32. Accordingly, Riechmann et al., (op. cit.) chose these amino acids from the donor immunoglobulins.

It is also important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding. Computer programs to create models of proteins such as antibodies are generally available and well known to those skilled in the art (see, Levy et al., Biochemistry, 28, 7168-7175 (1989); Bruccoleri et al., Nature, 335, 564-568 (1988); Chothia et al., Science, 233, 755-758 (1986), all of which are incorporated herein by reference). These do not form part of the invention. Indeed, because all antibodies have similar structures, the known antibody structures, which are available from the Brookhaven Protein Data Bank, can be used if necessary as rough models of other antibodies. Commercially available computer programs can be used to display these models on a computer monitor, to calculate the distance between atoms, and to estimate the likelihood of different amino acids interacting (see, Ferrin et al., J. Mol. Graphics, 6, 13-27 (1988)).

In addition to the above categories, which describe when an amino acid in the humanized immunoglobulin may be taken from the donor, certain amino acids in the humanized immunoglobulin may be taken from neither the donor nor acceptor, if then fall in:

Category 5: If the amino acid at a given position in the donor immunoglobulin is "rare" for human sequences, and the amino acid at that position in the acceptor immunoglobulin is also "rare" for human sequences, as defined above, then the amino acid at that position in the humanized immunoglobulin may be chosen to be some amino acid "typical" of human sequences. A preferred choice is the amino acid that occurs most often at that position in the known human sequences belonging to the same subgroup as the acceptor sequence.

Humanized antibodies generally have at least three potential advantages over mouse or in some cases chimeric antibodies for use in human therapy:

(1) Because the effector portion is human, it may interact better with the other parts of the human immune system (e.g., destroy the target cells more efficiently by complement-dependent cytotoxicity (CDC) or antibody-dependent cellular cytotoxicity (ADCC)).

(2) The human immune system should not recognize the framework or constant region of the humanized antibody as foreign, and therefore the antibody response against such an injected antibody should be less than against a totally foreign mouse antibody or a partially foreign chimeric antibody.

(3) Injected mouse antibodies have been reported to have a half-life in the human circulation much shorter than the half-life of normal antibodies (D. Shaw et al., J. Immunol., 138, 4534-4538 (1987)). Injected humanized antibodies will presumably have a half-life more similar to naturally occurring human antibodies, allowing smaller and less frequent doses to be given.

In one aspect, the present invention is directed to designing humanized antibodies that are produced by expressing recombinant DNA segments encoding the heavy and light chain CDR's from a donor immunoglobulin capable of binding to a desired antigen, such as IL-31. attached to DNA segments encoding acceptor human framework regions.

The DNA segments will typically further include an expression control DNA sequence operably linked to the humanized immunoglobulin coding sequences, including naturally-associated or heterologous promoter regions. The expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, N.Y., (1979), which is incorporated herein by reference).

Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to the predetermined antigen, such as IL-31, and produced by well known methods in any convenient mammalian source including, mice, rats, rabbits, or other vertebrates, capable of producing antibodies. Suitable source cells for the constant region and framework DNA sequences, and host cells for immunoglobulin expression and secretion, can be obtained from a number of sources, such as the American Type Culture Collection ("Catalogue of Cell Lines and Hybridomas," sixth edition (1988) Rockville, Md. U.S.A., which is incorporated herein by reference).

In addition to the humanized immunoglobulins specifically described herein, other "substantially homologous" modified immunoglobulins to the native sequences can be readily designed and manufactured utilizing various recombinant DNA techniques well known to those skilled in the art. A variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene, 8, 81-97 (1979) and S. Roberts et al., Nature, 328, 731-734 (1987), both of which are incorporated herein by reference).

The humanized antibodies of the invention include fragments as well as intact antibodies. Typically, these fragments compete with the intact antibody from which they were derived for antigen binding. The fragments typically bind with an affinity of at least $10^7$ M.$^{-1}$, and more typically $10^8$ or $10^9$ M.$^{-1}$ (i.e., within the same ranges as the intact antibody). Humanized antibody fragments include separate heavy chains, light chains Fab, Fab' F(ab')$_2$, and Fv. Fragments are produced by recombinant DNA techniques, or by enzymic or chemical separation of intact immunoglobulins.

For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5): 489 498; Studnicka et al., 1994, Protein Engineering 7(6): 805 814; Roguska et al., 1994, PNAS 91: 969 973; Tan et al., 2002, J. Immunol. 169: 1119 25; Caldas et al., 2000, Protein Eng. 13: 353 60; Morea et al., 2000, Methods 20: 267 79; Baca et al., 1997, J. Biol. Chem. 272: 10678 84; Roguska et al., 1996, Protein Eng. 9: 895 904; Couto et al., 1995, Cancer Res. 55 (23 Supp): 5973s 5977s; Couto et al., 1995, Cancer Res. 55: 1717 22; Sandhu, 1994, Gene 150: 409 10; Pedersen et al., 1994, J. Mol. Biol. 235: 959 73; Jones et al., 1986, Nature 321: 522-525; Reichmann et al., 1988, Nature 332: 323-329; and Presta, 1992, Curr. Op. Struct. Biol. 2: 593-596.

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab').sub.2 fragments (Carter et al., Bio/Technology 10: 163-167 (1992)). According to another approach, F(ab').sub.2 fragments can be isolated directly from recombinant host cell culture. Other techniques for the production of antibody fragments will be apparent to the skilled practitioner. Further, examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. Thus, the invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention (e.g., those comprising an immunogenic or antigenic epitope) fused or conjugated to heterologous polypeptide sequences (e.g., antibody domains other than the variable regions). For example, the polypeptides of the present invention may be fused or conjugated to an antibody Fc region, or portion thereof. For example, polypeptides of the present invention (including fragments or variants thereof), may be fused with the constant domain of immunoglobulins (IgA, IgE, IgG, IgM), or portions thereof ($C_H1$, $C_{H2}$, $C_{H3}$, or any combination thereof and portions thereof, resulting in chimeric polypeptides. The antibody portion fused to a polypeptide of the present invention may comprise the constant region, hinge region, $C_{H1}$ domain, $C_{H2}$ domain, and $C_{H3}$ domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties). By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

As discussed above, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (See, e.g., EP 394,827; Traunecker et al., Nature 331:84-86 (1988)). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995)0. Such techniques also include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Moreover, the polypeptides of the invention (e.g., antibodies or fragments thereof) can be fused to marker sequences, such as a peptide to facilitates their purification. In a further embodiment, nucleic acids encoding the polypeptides of the invention (including, but not limited to nucleic acids encoding immunogenic and/or antigenic epitopes) can also be recombined with a gene of interest as an epitope tag (e.g., the hemagglutinin tag ("HA") or flag tag) to aid in detection and purification of the expressed polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment, diagnosis, detection, and/or prevention regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, .beta.-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionuclide).

A variety of assays known to those skilled in the art can be utilized to detect antibodies which bind to IL-31 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant IL-31 protein or polypeptide.

Antibodies to IL-31 may be used for tagging cells that express IL-31; for isolating IL-31 by affinity purification; for diagnostic assays for determining circulating levels of IL-31 polypeptides; for detecting or quantitating soluble IL-31 as a marker of underlying pathology or disease; in analytical methods employing FACS; for screening expression libraries; for generating anti-idiotypic antibodies; and as neutralizing antibodies or as antagonists to block IL-31 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-31 or fragments thereof may be used in vitro to detect denatured IL-31 or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Binding polypeptides can also act as IL-31 "antagonists" to block IL-31 binding and signal transduction in vitro and in vivo. These anti-IL-31 binding polypeptides would be useful for inhibiting IL-31 activity or protein-binding.

Polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting carrier or vehicle for cell/tissue-specific delivery of generic anti-complementary-detectable/cytotoxic molecule conjugates.

In another embodiment, IL-31 antibody-cytokine fusion proteins can be used for in vivo killing of target tissues (for example, leukemia, lymphoma, lung cancer, colon cancer, melanoma, pancreatic cancer, ovarian cancer, skin, blood and bone marrow cancers, or other cancers wherein IL-31 receptors are expressed) (See, generally, Hornick et al., *Blood* 89:4437-47, 1997). The described fusion proteins enable targeting of the antibody to a desired site of action, thereby providing an elevated local concentration of antibody. Suitable IL-31 polypeptides or anti-IL-31 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the IL-31 polypeptide or anti-IL-31 antibody targets vascular cells or tissues, such polypeptide or antibody may be conjugated with a radionuclide, and particularly with a beta-emitting radionuclide, to reduce restenosis.

The monoclonal antibodies of the present invention can be measured for their ability to inhibit, block, or neutralize the IL-31 ligand as determined by various in vivo models known in the art and described herein, including but not limited to the NC/Nga model, the Ova epicutaneous model, the chronic hypersensitivity model, and the chronic hapten model.

Both skin-homing T cells and epidermal keratinocytes have been implicated in the pathology of skin diseases in humans. IL-31 mRNA and protein expression is restricted to the skin-homing CLA+ T cell population in humans. As such, an antagonist to IL-31, including an antibody or receptor antagonist will be useful in treating skin and epidermal diseases which have expression of CLA+ T cells. Such diseases include, for example, atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. Chemokine markers such as TARC and MDC are useful to measure the effect of a neutralizing monoclonal antibody to IL-31. As shown in Example 15, the inhibitory effects of treatment with anti-1131 antibodies described herein can be measured by monitoring the levels of TARC and MDC.

Contact Dermatitis

Allergic contact dermatitis is defined as a T cell mediated immune reaction to an antigen that comes into contact with the skin. The CLA+ T cell population is considered to be involved in the initiation of dermatitis since allergen dependent T cell responses are largely confined to the CLA+ population of cells (See Santamaria-Babi, L. F., et al., *J Exp Med:* 181, 1935, (1995)). Recent data has found that only memory (CD45RO+) CD4+ CLA+ and not CD8+ T cells proliferate and produce both type-1 (IFN-) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol:* 51, 32, (2004).

In animal models, it has been demonstrated that allergic contact dermatitis is T-cell dependent and that the allergic-responsive T cells migrate to the site of allergen application.

See generally: Engeman T. M., et al., *J Immunol:* 164, 5207, (2000); Ferguson T. A. & Kupper T. S. *J Immunol.* 150, 1172, (1993); and Gorbachev A. V. & Fairchild R. L. *Crit. Rev Immunol.* 21, 451 (2001). Since CLA+ T cells produce IL-31 and IL-31 stimulation of skin keratinocytes can induce pro-inflammatory chemokines, such as TARC and MDC, IL-31 may be involved in the pathophysiology of contact dermatitis. By using a neutralizing IL-31 antibody in a mouse model of contact hypersensitivity. See Example 8.

Thus, neutralization of IL-31 by the antibodies described herein may be used to improve clinical outcome of Contat Hypersenstivity by inhibition, reduction, neutralization, prevention or blocking the inflammation and/or scratching associated with disease.

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J. M., *Arch Dermatol:* 135, 1551 (1999). Histopathology reveals spongiosis, hyper and focal parakeratosis in acute lesions, whereas marked epidermal hyperplasia with hyper and parakeratosis, acanthosis/hypergranulosis and perivascular infiltration of the dermis with lymphocytes and abundant mast cells are the hallmarks of chromic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol:* 14, 13, (2004)). A significant increase in circulating CLA+ T cells among AD patients compared with control individuals has been documented (See Teraki Y., et al., Br *J Dermatol:* 143, 373 (2000), while others have demonstrated that memory CLA+ T cells from AD patients preferentially respond to allergen extract compared to the CLA– population (See Santamaria-Babi, L. F., et al., *J Exp Med:* 181, 1935, (1995)). In humans, the pathogenesis of atopic disorders of the skin have been associated with increases in CLA+ T cells that express increased levels of Th-2-type cytokines like IL-5 and IL-13 9, 10. See Akdis M., et al., *Eur J Immunol:* 30, 3533 (2000); and Hamid Q., et al., *J Allergy Clin Immunol:* 98, 225 (1996).

NC/Nga Mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy:* 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101: 1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model are used to investigate expression of IL-31 and IL-31RA in AD, as well as the ability of the antibodies described herein to inhibit, reduce, or neutralize the effects of IL-31. See Examples 9 and 10 herein. In one study using the NC/Nga in vivo model (Example 10), administration of rat anti-mouse IL-31 antibodies showed reduction in scratching, but not a reduction in dermatitis. The antibodies described herein are useful to inhibit scratching associated with dermatitis and pruritic diseases including atopic dermatitis, prurigo nodularis, and eczema. An inhibition, reduction, or prevention of scratching, alone, can be effective in treating pruritic diseases including, but not limited to, atopic dermatitis, prurigo nodularis, and eczema, since cessation of scratching will stop progression of dermatitis, the development of which is dependent on scratching.

Additional models to measure the inhibitory effects of the anti-IL-31 antibodies described herein are described by Umeuchi, H. et al., European Journal of Pharmacology, 518: 133-139, 2005; and by Yoo, J. et al., J. Experimental Medicine, 202:541-549, 2005.

Thus, neutralization of IL-31 by the antibodies described herein may be used to improve clinical outcome of dermatitis and pruritic diseases including atopic dermatitis, prurigo nodularis, and eczema by inhibition, reduction, prevention or blocking the inflammation and/or scratching associated with disease.

Drug-Induced Delayed Type Cutaneous Allergic Reactions

Drug-induced delayed type cutaneous allergic reactions are very heterogeneous and may mirror many distinct pathophysiological events. See Brockow K., et al., *Allergy:* 57, 45 (2002). Immunological mechanisms involved in these reactions have been shown as either antibody or cell mediated. In immediate drug allergy an IgE-mediated antibody reaction can be demonstrated by a positive skin prick and/or intradermal test after 20 min, whereas non-immediate reactions to drugs can occur more than one hour after last drug intake and are often T-cell mediated. Non-immediate T-cell mediated delayed type reactions can occur in patients with adverse drug reactions to penicillins for example. Proliferative T cell responses to penicillins have been shown to be restricted to the memory (CD45RO+) CLA+ subpopulation of T cells from penicillin allergic patients whereas the CD45RO+ CLA– subset shows no proliferative response. See Blanca M., Leyva L., et al., *Blood Cells Mol Dis:* 31, 75 (2003). Delayed-type hypersensitivity (DTH) reactions can be artificially reproduced in mice, allowing assessment of factors that may be involved in the initiation and perpetuation of the DTH response. Il-31 neutralizing antibody could be effective in delayed type hypersensitivity reactions. See Example 51.

Toxic epidermal necrolysis (TEN) is a very rare but extremely severe drug reaction characterized by widespread apoptosis of epidermis with extensive blisters. Studies have shown that lymphocytes infiltrating the blister are CLA+ T cells and can exhibit cytotoxicity towards epidermal keratinocytes. See Leyva L., et al., *J Allergy Clin Immunol:* 105, 157 (2000); and Nassif A., Bensussan A., et al., *J Allergy Clin Immunol:* 114, 1209 2004). A transgenic mouse system, whereby OVA is expressed under the control of the keratin-5 (K5) promoter in the epidermal and hair follicular keratinocytes of mice, has been generated to establish an animal model for TEN. OVA specific CD8+ T cells, when adoptively transferred into K5-OVA mice, undergo activation and proliferation in the skin-draining lymph nodes and target the skin of K5-OVA mice, resulting in development of skin lesions that are reminiscent of TEN. See Azukizawa H., et al., *Eur J Immunol:* 33, 1879 (2003).

Thus, neutralization of IL-31 by the antibodies described herein may be used to improve clinical outcome of TEN by inhibition, reduction, prevention or blocking the inflammation and/or scratching associated with disease.

Bullous Pemphigoid

Bullous pemphigoid is a subepidermal disorder which manifests as subepidermal blisters with a dermal infiltrate of neutrophils and eosinophils. Diagnosis is characterized by the presence of antigen-specific antibodies against specific adhesion proteins of the epidermis and dermal-epidermal junction. See Jordon R. E., et al., *JAMA:* 200, 751 (1967). Studies analyzing the role of T cells in the pathogenesis of bullous pemphigoid by analysis of PBL and skin blister T cells have found a predominance of CLA+ T cells expressing increased levels of Th2-cytokines like IL-4 and IL-13. See Teraki Y., et al., *J Invest Dermatol:* 117, 1097 (2001). In bullous pemphigoid patients following therapy with systemic corticosteroids, the frequency of CLA+, but not CLA−, interleukin-13-producing cells is significantly decreased. Decreases in CLA+ cells following corticosteroid treatment is associated with clinical improvement. See Teraki, ibid.

Thus, neutralization of IL-31 by the antibodies described herein may be used to improve clinical outcome of bullous pemphigoid by inhibition, reduction, prevention or blocking the inflammation and/or scratching associated with disease.

Alopecia Greata

Alopecia greata (AA) is regarded as a tissue-restricted autoimmune disease of hair follicles in which follicular activity is arrested because of the continued activity of lymphocytic infiltrates. AA results in patches of complete hair loss anywhere on the body, though actual loss of hair follicles does not occur, even in hairless lesions. Although clinical signs of inflammation are absent, skin biopsies from sites of active disease show perifollicular lymphocytic inflammation of primarily CD4+ cells, along with a CD8+ intrafollicular infiltrate. See Kalish R. S. & Gilhar A. *J Investig Dermatol Symp Proc:* 8, 164 (2003).

Studies have shown that scalp skin infiltrating CD4+ or CD8+ lymphocytes express CLA and, in peripheral blood of individuals with AA, the percent of CLA+CD4+ or CD8+ lymphocytes is significantly higher than that of normal controls. Furthermore, patients with severe or progressive AA show a much higher CLA-positivity compared to patients recovering from the disease and a decrease in percent CLA+ cells parallels a good clinical course. See Yano S., et al., *Acta Derm Venereol:* 82, 82 (2002). These studies therefore suggest that CLA+ lymphocytes may play an important role in AA. Xenograft models have demonstrated that activated T cells are likely to play a role in the pathogenesis of AA. Lesional scalp from AA patients grafted onto nude mice regrows hair coincident with a loss of infiltrating lymphocytes from the graft and, transfer of activated lesional T cells to SCID mice can transfer hair loss to human scalp explants on SCID mice. See Kalish R. S. & Gilhar A. *J Investig Dermatol Symp Proc:* 8, 164 (2003).

A variety of immunomodulating therapies are part of the usual treatment for this disorder however none of these treatments have been consistent in their efficacy. See Tang L., et al., *J Invest Dermatol:* 120, 400 (2003); Tang L., et al., (2004); and Tang L., et al., *J Am Acad Dermatol:* 49, 1013 (2003). Nevertheless, their uses in valid animal models provide a tool to dissect out molecular mechanisms of therapeutic effects. See Shapiro J., et al., *J Investig Dermatol Symp Proc:* 4, 239 (1999); Tang L., et al., Old wine in new bottles: reviving old therapies for alopecia greata using rodent models (2003); and Verma D. D., et al., *Eur J Dermatol:* 14, 332 (2004).

Thus, neutralization of IL-31 by the antibodies described herein may be used to improve clinical outcome of alopecia greata by inhibition, reduction, prevention or blocking the inflammation and/or scratching associated with disease.

Acne Rosacea/Acne Vulgaris

Acne vulgaris, a disorder of the pilosebaceous apparatus, is the most common skin problem of adolescence. Abnormalities in follicular keratinization are thought to produce the acne lesion. Acne rosacea is differentiated from acne vulagaris by the presence of red papules, pustules, cysts and extensive telangiectasias, but the absence of comedones (white heads). Increased sebum excretion from sebaceous glands is a major factor in the pathophysiology of acne vulgarism. Other sebaceous gland functions are also associated with the development of acne, including sebaceous proinflammatory lipids; different cytokines produced locally; periglandular peptides and neuropeptides, such as corticotrophin-releasing hormone, which is produced by sebocytes; and substance P, which is expressed in the nerve endings at the vicinity of healthy-looking glands of acne patients. See Zouboulis C. C. *Clin Dermatol:* 22, 360 (2004).

Although the pathophysiology of acne vulgaris and acne rosacea remains unknown, clinical observations and histopathologic studies suggest that inflammation of the pilosebaceous follicle may be central to the pathogenesis of rosacea and acne vulgarism Early studies on analysis of T cell subsets infiltrating rosacea legions indicated that the majority of T cells expressed CD4. See Rufli T. & Buchner S. A. *Dermatologica:* 169, 1 (1984).

CD4+ T cells produce IL-31 and IHC analysis of skin for IL-31 expression suggests that IL-31 is expressed in sebaceous and sweat glands. IL-31 stimulation of epidermal keratinocytes induces expression of chemokines which likely results in cellular infiltration suggesting that IL-31 may contribute to the pro-inflammatory response in skin. See Dillon S. R., et al., *Nat Immunol:* 5, 752 (2004). IL-31 may therefore contribute to the pathophysiology of acne rosacea and acne vulgarism Thus, neutralization of IL-31 by the antibodies described herein may be used to improve clinical outcome of acne vulgaris by inhibition, reduction, prevention or blocking the inflammation and/or scratching associated with disease.

Prurigo Nodularis

Prurigo nodularis is an eruption of lichenified or excoriated nodules caused by intractable pruritus that is difficult to treat. While chronic rubbing results in lichenification, and scratching in linear excoriations, individuals who pick and gouge at their itchy, irritated skin tend to produce markedly thickened papules known as prurigo nodules. Although prurigo nodularis is not specific to atopic dermatitis, many patients with these nodules also have an atopic reaction, which manifests as allergic rhinitis, asthma, or food allergy. T cells represent the majority of infiltrating cells in prurigo lesions and these lesions often represents the most pruritic skin lesion in atopy patients.

Topical treatment of prurigo nodularis with capsaicin, an anti-pruritic alkaloid that interferes with the perception of purities and pain by depletion of neuropeptides like substance P in small sensory cutaneous nerves, has proven to be an effective and safe regimen resulting in clearing of the skin lesions. See Stander S., et al., *J Am Acad Dermatol:* 44, 471 (2001). Studies of the itch response in NC/Nga mice using capsaicin treatment showed that the spontaneous development of dermatitis lesions was almost completely prevented. Furthermore, the elevation of serum IgE levels was significantly suppressed and infiltrating eosinophils and mast cell numbers in lesional skin of capsaicin treated mice were reduced. See Mihara K., et al., *Br J Dermatol:* 151, 335 (2004). The observations from this group suggest that scratching behaviour might contribute to the development of dermatitis by enhancing various immunological responses, therefore implying that prevention of the itch sensation and/or itch-associated scratching behaviour might be an effective treatment for AD. See Mihara K., et al., *Br J Dermatol:* 151, 335 (2004). Thus, the anti-Il-31 antibodies described herein will be useful in minimizing the effects of AD, prurigo nodularis, and other pruritic diseases as they are shown herein to reduce the amount of scratching in NC/Nga mice.

Chronic delivery of IL-31 induces pruritis and alopecia in mice followed by the development of skin lesions resembling dermatitis suggesting that IL-31 may induce itching. See Dillon S. R., et al., *Nat Immunol:* 5, 752 (2004). The involvement of IL-31 was tested in induction of the itch response by two methods (i) capsaicin treatment of IL-31-treated mice and (ii) IL-31 treatment of Tac1 knockout mice, which have significantly reduced nociceptive pain responses because of lack of expression of neuropeptides in Example 52. In addition, whether neutralization of IL-31 in IL-31 treated mice could prevent pruritis and alopecia was tested in Example 12.

Thus, neutralization of IL-31 by the antibodies described herein may be used to improve clinical outcome of prurigo nodularis by inhibition, reduction, prevention or blocking the inflammation and/or scratching associated with disease.

Skin-Tropic Viruses and Viral Associated Pruritis

Herpes Simplex Virus (HSV)-specific CD8+ T cells in the peripheral blood and HSV-specific CD8+ T cells recovered from herpes lesions express high levels of CLA where as non-skin-tropic herpes virus-specific CD8+ T cells lack CLA expression. See Koelle D. M., et al., *J Clin Invest:* 110, 537 (2002). HSV-2 reactive CD4+ T lymphocytes also express CLA, but at levels lower than those previously observed for CD8+ T lymphocytes. See Gonzalez J. C., et al., *J Infect Dis:* 191, 243 (2005). Pruritis has also been associated with herpes viral infections (See Hung K. Y., et al., *Blood Purif.* 16, 147 (1998). though other viral diseases, like HIV, have also been associated with pruritic skin lesions. Severe, intractable pruritus, often associated with erythematopapular skin lesions and hypereosinophilia, is a condition observed in some non-atopic, HIV-infected patients 36. See Singh F. & Rudikoff D, *Am J Clin Dermatol;* 4, 177 (2003); and Milazzo F., Piconi S., et al., *Allergy:* 54, 266 (1999).

The association of skin-tropic viruses with pruritis and CLA+ T cells suggests that IL-31 producing T cells may be involved in the pathophysiology of viral infections.

Thus, neutralization of IL-31 by the antibodies described herein may be used to improve clinical outcome of pruritis associated with skin-tropic viruses by inhibition, reduction, prevention or blocking the inflammation and/or scratching associated with disease.

Moreover, inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory antibodies and binding polypeptides, such as anti-IL-31 antibodies and binding polypeptides described herein, could have crucial therapeutic potential for a vast number of human and animal diseases, from asthma and allergy to autoimmunity and septic shock. As such, use of anti-inflammatory anti IL-31 antibodies and binding polypeptides described herein can be used therapeutically as IL-31 antagonists described herein, particularly in diseases such as arthritis, endotoxemia, inflammatory bowel disease, psoriasis, related disease and the like.

1. Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides, such as anti-IL-31 antibodies and binding polypeptides of the present invention. For Example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-31, and as such a molecule that binds or inhibits IL-31, such as anti IL-31 antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of soluble IL-31RA comprising polypeptides (including heterodimeric and multimeric receptors described herein), such as IL-31RA-Fc4 or other IL-31RA soluble and fusion proteins to these CIA model mice was used to evaluate the use of IL-31RA to ameliorate symptoms and alter the course of disease. As a molecule that modulates immune and inflammatory response, IL-31, may induce production of SAA, which is implicated in the pathogenesis of rheumatoid arthritis, IL-31 antagonists may reduce SAA activity in vitro and in vivo, the systemic or local administration of IL-31 antagonists such as anti-IL-31 antibodies or binding partners, IL-31 RA comprising polypeptides (including heterodimeric and multimeric receptors described herein), such as IL-3 IRA-Fc4 or other IL-31RA soluble and fusion proteins can potentially suppress the inflammatory response in RA. Other potential therapeutics include IL-31 RA polypeptides, soluble heterodimeric and multimeric receptor polypeptides, or anti IL-31 antibodies or binding partners of the present invention, and the like.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory antibodies and binding polypeptides, such as anti-IL-31 antibodies and binding polypeptides of the present invention, could aid in preventing and treating endotoxemia in humans and animals. Other potential therapeutics include IL-31RA polypeptides, soluble heterodimeric and multimeric receptor polypeptides, or anti IL-31 antibodies or binding partners of the present invention, and the like, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1 ug injection of *E. coli* LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF. Since LPS induces the production of pro-inflammatory factors possibly contributing to the pathology of endotoxemia, the neutralization of IL-31 activity, SAA or other pro-inflammatory factors by antagonizing IL-31 polypeptide can be used to reduce the symptoms of endotoxemia, such as seen in endotoxic shock. Other potential therapeutics include IL-31RA polypeptides, soluble heterodimeric and multimeric receptor polypeptides, or anti-IL-31 antibodies or binding partners of the present invention, and the like.

3 Inflammatory Bowel Disease. IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. Potential therapeutics include IL-31RA polypeptides, soluble heterodimeric and multimeric receptor polypeptides, or anti-IL-31 antibodies or binding partners of the present invention, and the like., could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (e.g. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-IL-31 antibodies or binding partners, soluble IL-31RA comprising polypeptides (including heterodimeric and multimeric receptors), such as IL-31RA-Fc4 or other IL-31RA soluble and fusion proteins to these TNBS or DSS models can be used to evaluate the use of IL-31 antagonists to ameliorate symptoms and alter the course of gastrointestinal disease. IL-31 may play a role in the inflammatory response in colitis, and the neutralization of IL-31 activity by administrating IL-31 antagonists is a potential therapeutic approach for IBD. Other potential therapeutics include IL-31RA polypeptides, soluble heterodimeric and multimeric receptor polypeptides, or anti-IL-31 antibodies or binding partners of the present invention, and the like.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-31RA polypeptides, soluble heterodimeric and multimeric receptor polypeptides, or anti-IL-31 antibodies or binding partners of the present invention, and the like, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases r IL-31 was isolated from tissue known to have important immunological function and which contain cells that play a role in the immune system. IL-31 is expressed in CD3+ selected, activated peripheral blood cells, and it has been shown that IL-31 expression increases after T cell activation. Moreover, results of experiments described in the Examples section herein suggest that polypeptides of the present invention can have an effect on the growth/expansion of monocytes/macrophages, T-cells, B-cells, NK cells and/or differentiated state of monocytes/macrophages, T-cells, B-cells, NK cells or these cells' progenitors. Factors that both stimulate proliferation of hematopoietic progenitors and activate mature cells are generally known, however, proliferation and activation can also require additional growth factors. For example, it has been shown that IL-7 and Steel Factor (c-kit ligand) were required for colony formation of NK progenitors. IL-15+IL-2 in combination with IL-7 and Steel Factor was more effective (Mrózek et al., *Blood* 87:2632-2640, 1996). However, unidentified cytokines may be necessary for proliferation of specific subsets of NK cells and/or NK progenitors (Robertson et. al., *Blood* 76:2451-2438, 1990). Similarly, IL-31 may act alone or in concert or synergy with other cytokines to enhance growth, proliferation expansion and modification of differentiation of monocytes/macrophages, T-cells, B-cells or NK cells.

The present invention provides a method for inhibiting activation or differentiation of monocytes/macrophages. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation.

The tissue distribution of receptors for a given cytokine offers a strong indication of the potential sites of action of that cytokine. Expression of IL-31RA was seen in monocytes and B-cells, with a dramatic increase of expression upon activation for CD3+, CD4+, and CD8+ T-cells. In addition, two monocytic cell lines, THP-1 (Tsuchiya et al., *Int. J. Cancer* 26:171-176, 1980) and U937 (Sundstrom et al., *Int. J. Cancer* 17:565-577, 1976), were also positive for IL-31RA expression.

Expression of OSMR is reported to be very broad (Mosley et al., *JBC* 271:32635-32643, 1996). This distribution of IL-31RA and OSM receptors supports a role for IL-31 in immune responses, especially expansion of T-cells upon activation or a role in the monocyte/macrophage arm of the immune system.

Thus, particular embodiments of the present invention are directed toward use of soluble IL-31RA/OSMR heterodimers as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA expression in activated immune cells such as activated CD4+ and CD19+ cells showed that IL-31RA receptor may be involved in the body's immune defensive reactions against foreign invaders: such as microorganisms and cell debris, and could play a role in immune responses during inflammation and cancer formation. As such, antibodies and binding partners of the present invention that are agonistic or antagonistic to IL-31RA receptor function, such as IL-31, can be used to modify immune response and inflammation.

IL-31 may find utility in the suppression of the immune system, such as in the treatment of autoimmune diseases, including rheumatoid arthritis, multiple sclerosis, diabetes mellitus, inflammatory bowel disease, Crohn's disease, etc. Immune suppression can also be used to reduce rejection of tissue or organ transplants and grafts and to treat T-cell, B-cell or monocyte-specific leukemias or lymphomas, and other cancers, by inhibiting proliferation of the affected cell type. Moreover IL-31 can be used to detect monocytes, macrophages, and activated T-cells and aid in the diagnosis of such autoimmune disease, particularly in disease states where monocytes are elevated or activated.

IL-31 polypeptides, peptides, antibodies, and the like may also be used within diagnostic systems for the detection of circulating levels of IL-31. Within a related embodiment, antibodies or other agents that specifically bind to IL-31 polypeptides can be used to detect circulating IL-31 polypeptides. Elevated or depressed levels of ligand polypeptides may be indicative of pathological conditions, including cancer. IL-31 polypeptides may contribute to pathologic processes and can be an indirect marker of an underlying disease.

Moreover, one of skill in the art would recognize that antagonists of IL-31 are useful. For example, in atherosclerotic lesions, one of the first abnormalities is localization of monocyte/macrophages to endothelial cells. These lesions could be prevented by use of antagonists to IL-31. Anti-IL-31 antibodies (e.g., IL-31 neutralizing antibody), IL-31RA soluble receptors, heterodimers and multimers, and IL-31 binding partners can also be used as antagonists to the IL-31. Moreover, monoblastic leukemia is associated with a variety of clinical abnormalities that reflect the release of the biologic products of the macrophage, examples include high levels of lysozyme in the serum and urine and high fevers. Moreover, such leukemias exhibit an abnormal increase of monocytic cells. These effects could possibly be prevented by antagonists to IL-31, such as described herein. Moreover, anti-IL-31 can be conjugated to molecules such as toxic moieties and cytokines, as described herein to direct the killing of leukemia monocytic cells.

As IL-31 is expressed in a T-cell, macrophage and monocyte-specific manner, and these diseases involve abnormalities in monocytic cells, such as cell proliferation, function, localization, and activation, the polynucleotides, polypeptides, and antibodies of the present invention can be used to as diagnostics to detect such monocytic cell abnormalities, and indicate the presence of disease. Such methods involve taking a biological sample from a patient, such as blood, saliva, or biopsy, and comparing it to a normal control sample. Histological, cytological, flow cytometric, biochemical and other methods can be used to determine the relative levels or localization of IL-31, or cells expressing IL-31, i.e., monocytes, in the patient sample compared to the normal control. A change in the level (increase or decrease) of IL-31 expression, or a change in number or localization of monocytes (e.g., increase or infiltration of monocytic cells in tissues where they are not normally present) compared to a control would be indicative of disease. Such diagnostic methods can also include using radiometric, fluorescent, and colorimetric tags attached to polynucleotides, polypeptides or antibodies of the present invention. Such methods are well known in the art and disclosed herein.

IL-31 has been shown to be expressed in activated mononuclear cells, and may be involved in regulating inflammation. As such, polypeptides of the present invention can be assayed and used for their ability to modify inflammation, or can be used as a marker for inflammation. Methods to determine proinflammatory and antiinflammatory qualities of IL-31 are known in the art and discussed herein. Moreover, it may be involved in up-regulating the production of acute phase reactants, such as serum amyloid A (SAA), α1-antichymotrypsin, and haptoglobin, and that expression of IL-31RA receptor ligand may be increased upon injection of lipopolysaccharide (LPS) in vivo that are involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, J. *Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand such as IL-31 that acts as a pro-inflammatory molecule and induces production of SAA, antagonists would be useful in treating inflammatory disease and other diseases associated with acute phase response proteins induced by the ligand. Such antagonists are provided by the present invention. For example, a method of reducing inflammation comprises administering to a mammal with inflammation an amount of a composition of IL-31, or anti-IL-31 antibody (e.g., neutralizing antibody) that is sufficient to reduce inflammation. Moreover, a method of suppressing an inflammatory response in a mammal with inflammation can comprise: (1) determining a level of serum amyloid A protein; (2) administering a composition comprising a IL-31 polypeptide or anti-IL-31 antibody as described herein in an acceptable pharmaceutical carrier; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Like IL-31, analysis of the tissue distribution of the mRNA corresponding it's IL-31RA receptor cDNA showed that mRNA level was highest in monocytes and prostate cells, and is elevated in activated monocytes, and activated CD4+, activated CD8+, and activated CD3+ cells. Hence, IL-31RA receptor is also implicated in inducing inflammatory and immune response. Thus, particular embodiments of the present invention are directed toward use of IL-31-antibodies, and IL-31, as well as soluble IL-31RA receptor heterodimers as antagonists in inflammatory and immune diseases or conditions such as, pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA receptor and IL-31 expression in activated immune cells such as activated CD3+, monocytes, CD4+ and CD19+ cells showed that IL-31RA receptor may be involved in the body's immune defensive reactions against foreign invaders: such as microorganisms and cell debris, and could play a role in immune responses during inflammation and cancer formation. As such, IL-31 and IL-31-antibodies of the present invention that are agonistic or antagonistic to IL-31RA receptor function, can be used to modify immune response and inflammation.

IL-31 polypeptides that bind IL-31RA receptor polypeptides, and antibodies thereto are useful to:

1) Antagonize or block signaling via IL-31RA-comprising receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Antagonize or block signaling via the IL-31RA receptor receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via IL-31RA receptor (Hughes C et al., *J. Immunol.* 153: 3319-3325, 1994). Alternatively antibodies, such as monoclonal antibodies (MAb) to IL-31, can also be used as an antagonist to deplete unwanted immune cells to treat autoimmune disease. Asthma, allergy and other atopic disease may be treated with an MAb against, for example, anti-IL-31 antibodies, soluble IL-31RA receptor soluble receptors or IL-31RA/CRF2-4 heterodimers, to inhibit the immune response or to deplete offending cells. Blocking or inhibiting signaling via IL-31RA, using the polypeptides and antibodies of the present invention, may also benefit diseases of the pancreas, kidney, pituitary and neuronal cells. IDDM, NIDDM, pancreatitis, and pancreatic carcinoma may benefit. IL-31RA may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs to soluble IL-31RA receptor monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (IDDM), renal tumors and other diseases.

3) Agonize or initiate signaling via the IL-31RA receptors in the treatment of autoimmune diseases such as IDDM, MS, SLE, myasthenia gravis, rheumatoid arthritis, and IBD. IL-31 may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998). Similarly, IL-31 may be used to signal, deplete and deviate immune cells involved in asthma, allergy and atopoic disease. Signaling via IL-31RA receptor may also benefit diseases of the pancreas, kidney, pituitary and neuronal cells. IDDM, NIDDM, pancreatitis, and pancreatic carcinoma may benefit. IL-31 RA may serve as a target for MAb therapy of pancreatic cancer where a signaling MAb inhibits cancer growth and targets immune-mediated killing (Tutt, A L et al., *J. Immunol.* 161: 3175-3185, 1998). Similarly T-cell specific leukemias, lymphomas, plasma cell dyscrasia (e.g., multiple myeloma), and carcinoma may be treated with monoclonal antibodies (e.g., neutralizing antibody) to IL-31RA-comprising soluble receptors of the present invention.

Anti-IL-31 antibodies, soluble IL-31RA receptor monomeric, homodimeric, heterodimeric and multimeric polypeptides described herein can be used to neutralize/block IL-31RA receptor ligand activity in the treatment of autoimmune disease, atopic disease, NIDDM, pancreatitis and kidney dysfunction as described above.

Anti-IL-31 antibodies, and soluble IL-31RA-comprising receptors are useful as antagonists of IL-31. Such antagonistic effects can be achieved by direct neutralization or binding of its natural ligand. In addition to antagonistic uses, the soluble receptors can bind IL-31 and act as carrier or carrier proteins, in order to transport IL-31 to different tissues, organs, and cells within the body. As such, the soluble receptors can be fused or coupled to molecules, polypeptides or chemical moieties that direct the soluble-receptor-Ligand complex to a specific site, such as a tissue, specific immune cell, monocytes, or tumor. For example, in acute infection or some cancers, benefit may result from induction of inflammation and local acute phase response proteins. Thus, the soluble receptors described herein or antibodies of the present invention can be used to specifically direct the action of a pro-inflammatory IL-31 ligand. See, Cosman, D. Cytokine 5: 95-106, 1993; and Femandez-Botran, R. *Exp. Opin. Invest. Drugs* 9:497-513, 2000.

Generally, the dosage of administered IL-31 polypeptide (or IL-31RA analog or fusion protein) will vary depending upon such factors as the patient's age, weight, height, sex, general medical condition and previous medical history. Typically, it is desirable to provide the recipient with a dosage of IL-31 polypeptide which is in the range of from about 1 pg/kg to 10 mg/kg (amount of agent/body weight of patient), although a lower or higher dosage also may be administered as circumstances dictate. One skilled in the art can readily determine such dosages, and adjustments thereto, using methods known in the art.

Administration of a IL-31 polypeptide to a subject can be topical, inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-31 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having IL-31 binding activity (Potts et al., *Pharm. Biotechnol.* 10:213 (1997)).

A pharmaceutical composition comprising a protein, polypeptide, or peptide having IL-31 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having IL-31 binding activity and a pharmaceutically acceptable carrier are administered to a patient in a therapeutically effective amount. A combination of a protein, polypeptide, or peptide having IL-31 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response.

A pharmaceutical composition comprising IL-31 (or IL-31 analog or fusion protein) can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

The anti-IL-31 antibodies disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded-through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent (such as Doxorubicin) is optionally contained within the liposome. See Gabizon et al. J. National Cancer Inst. 81(19) 1484 (1989).

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Tween™, Pluronics™ or polyethylene glycol (PEG).

The formulation herein may also contain more than one active compound as necessary for the particular indication being treated, preferably those with complementary activities that do not adversely affect each other. For example, it may be desirable to further provide antibodies which bind to IL-31 in the one formulation. Alternatively, or in addition, the composition may comprise a chemotherapeutic agent or a cytokine. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in Drug Delivery Systems, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al U.S. Pat. No. 4,603,044, describe a hepatocyte-directed liposome vesicle delivery system, which has specificity for hepatobiliary receptors associated with the specialized metabolic cells of the liver.

Polypeptides having IL-31 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology,* 2nd Edition, Vol. III, Gregoriadis (ed.), page 317 (CRC Press 1993), Wassef et al., *Meth. Enzymol* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a IL-31 polypeptide or a IL-31 antagonist (e.g., an antibody or antibody fragment that binds a IL-31 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide.

Within one aspect the invention provides a monoclonal antibody comprising an monoclonal antibody that specifically binds a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6815; b) ATCC Patent Deposit Designation PTA-6816; c) ATCC Patent Deposit Designation PTA-6829; d) ATCC Patent Deposit Designation PTA-6830; e) ATCC Patent Deposit Designation PTA-6831; f) ATCC Patent Deposit Designation PTA-6871; g) ATCC Patent Deposit Designation PTA-6872; h) ATCC Patent Deposit Designation PTA-6875; and i) ATCC Patent Deposit Designation PTA-6873. Within an embodiment, the antibody neutralizes the interaction of IL-31 (SEQ ID NO:2) with IL-31RA (SEQ ID NO:5). Within another embodiment, the antibody is (a) a murine monoclonal antibody, (b) a humanized antibody derived from (a), or (c) an antibody fragment, or (d) a human monoclonal antibody. Within another embodiment the antibody further comprises a radionuclide, enzyme, substrate, cofactor, fluorescent marker, chemiluminescent marker, peptide tag, magnetic particle, or toxin. Within another embodiment the antibody further comprises PEGylation. Within another embodiment the antibody is a neutralizing antibody. Within another embodiment administration of the antibody to a mammal inhibits, prevents, reduces or blocks the pro-inflammatory activity of the polypeptide. Within another embodiment administration of the antibody to a mammal inhibits, prevents, reduces or blocks the scratching and dermatitis associated with the proinflammatory activity of the polypeptide.

Within another aspect the invention provides a monoclonal antibody that specifically binds a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6815; b) ATCC Patent Deposit Designation PTA-6816; c) ATCC Patent Deposit Designation PTA-6871; d) ATCC Patent Deposit Designation PTA-6829; and e) ATCC Patent Deposit Designation PTA-6830.

Within another aspect the invention provides a monoclonal antibody that specifically binds a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6815; b) ATCC Patent Deposit Designation PTA-6816; and c) ATCC Patent Deposit Designation PTA-6871.

Within another aspect the invention provides a monoclonal antibody that specifically binds a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6829; and b) ATCC Patent Deposit Designation PTA-6830.

Within another aspect is provided a monoclonal antibody that specifically binds a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6872; and b) ATCC Patent Deposit Designation PTA-6875.

Within another aspect is provided a monoclonal antibody that specifically binds a polypeptide comprising the amino acid sequence of SEQ ID NO: 11 wherein the polypeptide is capable of binding the monoclonal antibody produced by the hybridoma deposited with the American Type Culture Collection having the ATCC Patent Deposit Designation PTA-6874. Within an embodiment the antibody is a neutralizing antibody. Within an embodiment administration of the antibody to a mammal inhibits, prevents, reduces or blocks the pro-inflammatory activity of the polypeptide. Within an embodiment administration of the antibody to a mammal inhibits, prevents, reduces or blocks the scratching and dermatitis associated with the proinflammatory activity of the polypeptide.

Within another aspect the invention provides a method of reducing inflammation in a mammal comprising administering to the mammal an amount of the IL-31 antibodies described herein, whereby the inflammation is reduced.

Within another aspect the invention provides a method of treating a mammal afflicted with an inflammatory disease in which IL-31 plays a role, comprising: administering an antagonist of IL-31 to the mammal such that the inflammation is reduced, wherein the antagonist comprises (i) an antibody, antibody fragment, or binding polypeptide that specifically binds a polypeptide or polypeptide fragment of IL-31RA or (ii) a polypeptide or polypeptide fragment of IL-31RA; and wherein the inflammatory activity of IL-31 is reduced. Within an embodiment the disease is a inflammatory disease comprises pruritic diseases. Within an embodiment the disease is atopic dermatitis. Within an embodiment the disease is prurigo nodularis.

Within another aspect the invention provides a method of reducing, inhibiting, or preventing the effect of pruritis in a mammal in which IL-31 plays a role, comprising: administering an antagonist of IL-31 to the mammal such that the pruritis is reduced, wherein the antagonist comprises (i) an antibody, antibody fragment, or binding polypeptide that specifically binds a polypeptide or polypeptide fragment of the polypeptide comprising the amino acid sequence of SEQ ID NO:2, or a fragment thereof; and wherein the pruritic activity of IL-31 is reduced. Within an embodiment the disease of the mammal is atopic dermatitis. Within an embodiment the disease of the mammal is dermatitis. Within an embodiment the antibody is an antibody as described herein.

Within another aspect the invention provides a method of reducing, inhibiting, or preventing the effect of pruritis in a mammal in which IL-31 plays a role, comprising: administering an antagonist of IL-31 to the mammal such that the there is a reduction in itch in the mammal wherein the antagonist comprises (i) an antibody, antibody fragment, or binding polypeptide that specifically binds a polypeptide or polypeptide fragment of the polypeptide comprising the amino acid sequence of SEQ ID NO:2, or a fragment thereof; and whereby the scratching activity of IL-31 is reduced. Within an embodiment the disease of the mammal is atopic dermatitis. Within an embodiment the disease of the mammal is dermatitis. Within an embodiment the antibody is an antibody as described herein.

Within another aspect the invention provides a monoclonal antibody that specifically binds a polypeptide comprising the amino acid sequence of SEQ ID NO: 2, wherein the polypeptide is capable of binding the monoclonal antibody produced by the hybridoma clone designation number selected from: a) clone 292.12.3.1 (ATCC Patent Deposit Designation PTA-6815); b) clone 292.63.5.3 (ATCC Patent Deposit Designation PTA-6829); c) clone 292.72.3.1 (ATCC Patent Deposit Designation PTA-6816); d) clone 292.84.1.6 (ATCC Patent Deposit Designation PTA-6871); and e) clone 292.118.6.4 (ATCC Patent Deposit Designation PTA-6830).

Within another aspect the invention provides a monoclonal antibody that specifically binds a polypeptide comprising the amino acid sequence of SEQ ID NO: 2, wherein the polypeptide is capable of binding the monoclonal antibody produced by the hybridoma clone designation number selected from: a) clone 294.35.2.6.3 (ATCC Patent Deposit Designation PTA-6872); b) clone 294.144.3.5 (ATCC Patent Deposit Designation PTA-6873); c) clone 294.154.5.6 ATCC Patent Deposit Designation PTA-6875); and d) clone 294.163.2.1 (ATCC Patent Deposit Designation PTA-6831).

Within another aspect the invention provides a monoclonal antibody comprising an monoclonal antibody that is capable of competing for binding a polypeptide comprising the amino acid sequence of SEQ ID NO: 2 wherein the polypeptide is capable of binding the monoclonal antibody produced by the hybridoma deposited with the American Type Culture Collection having the ATCC Patent Deposit Designation selected from: a) ATCC Patent Deposit Designation PTA-6815; b) ATCC Patent Deposit Designation PTA-6816; c) ATCC Patent Deposit Designation PTA-6829; d) ATCC Patent Deposit Designation PTA-6830; e) ATCC Patent Deposit Designation PTA-6831; f) ATCC Patent Deposit Designation PTA-6871; g) ATCC Patent Deposit Designation PTA-6872; h) ATCC Patent Deposit Designation PTA-6875; and i) ATCC Patent Deposit Designation PTA-6873.

Within another aspect is provided a hybridoma, wherein the hybridoma is deposited with the American Type Culture Collection having the ATCC Patent Deposit Designation selected from: a) ATCC Patent Deposit Designation PTA-6815; b) ATCC Patent Deposit Designation PTA-6816; c) ATCC Patent Deposit Designation PTA-6829; d) ATCC Patent Deposit Designation PTA-6830; e) ATCC Patent Deposit Designation PTA-6831; f) ATCC Patent Deposit Designation PTA-6871; g) ATCC Patent Deposit Designation PTA-6872; h) ATCC Patent Deposit Designation PTA-6875; and i) ATCC Patent Deposit Designation PTA-6873.

Within another aspect the present invention provides a method of producing an antibody to a IL-31 polypeptide comprising: inoculating an animal with a polypeptide selected from the group consisting of: (a) a polypeptide consisting of 9 to 141 amino acids, wherein the polypeptide is identical to a contiguous sequence of amino acid residues in SEQ ID NO:2 from amino acid number 24 (Ser) to amino acid number 164 (Thr); a polypeptide as disclosed above; (c) a polypeptide comprising the amino acid sequence of SEQ ID NO:2 from amino acid number 38-52; (d) a polypeptide comprising the amino acid sequence of SEQ ID NO:2 from amino acid number 83-98; (e) a polypeptide comprising the amino acid sequence of SEQ ID NO:2 from amino acid number 104-117; (f) a polypeptide comprising the amino acid sequence of SEQ ID NO:2 from amino acid number 137-152; (g) a polypeptide comprising the amino acid sequence of SEQ ID NO:2 from amino acid number 38-152; (h) a polypeptide comprising the amino acid sequence of SEQ ID NO:2 from amino acid number 24-164; (c) a polypeptide comprising the amino acid sequence of SEQ ID NO:11 from amino acid number 38-52; (d) a polypeptide comprising the amino acid sequence of SEQ ID NO:11 from amino acid number 85-98; (e) a polypeptide comprising the amino acid sequence of SEQ ID NO:11 from amino acid number 104-118; (f) a polypeptide comprising the amino acid sequence of SEQ ID NO:11 from amino acid number 141-157; (g) a polypeptide comprising the amino acid sequence of SEQ ID NO:11 from amino acid number 38-157; (h) a polypeptide comprising the amino acid sequence of SEQ ID NO:11 from amino acid number 24-163; (i) a polypeptide comprising an antigenic epitope according to a Hopp/Woods hydrophilicity profile of SEQ ID NO:2 or SEQ ID NO 11, wherein the profile is based on a sliding six-residue window. Buried G, S, and T residues and exposed H, Y, and W residues ignored; and wherein the polypeptide elicits an immune response in the animal to produce the antibody; and isolating the antibody from the animal.

Within another aspect the present invention provides an antibody (e.g., neutralizing antibody) produced by the method as disclosed above, wherein the antibody binds to a polypeptide of SEQ ID NO:2 or SEQ ID NO:1. In one embodiment, the antibody disclosed above specifically binds to a polypeptide shown in SEQ ID NO:2 or SEQ ID NO:11.

Within another aspect the present invention provides a method of detecting the presence of IL-31 in a biological sample, comprising the steps of: (a) contacting the biological sample with an antibody, or an antibody fragment as disclosed above, wherein the contacting is performed under conditions that allow the binding of the antibody or antibody fragment to the biological sample, and (b) detecting any of the bound antibody or bound antibody fragment.

Within another aspect, the present invention provides a method of killing cancer cells comprising, obtaining ex vivo a tissue or biological sample containing cancer cells from a patient, or identifying cancer cells in vivo; producing a polypeptide by the method as disclosed herein; formulating the polypeptide in a pharmaceutically acceptable vehicle; and administering to the patient or exposing the cancer cells to the polypeptide; wherein the polypeptide kills the cells. In one embodiment the method of killing cancer cells is as disclosed above, wherein the polypeptide is further conjugated to a toxin. In one embodiment the antibody is as disclosed above, wherein the antibody is selected from the group consisting of: (a) polyclonal antibody, (b) murine monoclonal antibody, (c) humanized antibody derived from (b), (d) an antibody fragment, and (e) human monoclonal antibody.

Within another aspect, the present invention provides an antibody or antibody fragment that specifically binds to a polypeptide of comprising a sequence of amino acid residues selected from the group consisting of: (a) the polypeptide shown from residues 38 (Val) to 152 (Leu) as shown in SEQ ID NO:2; (b) the polypeptide shown from residues 27 (Leu) to 164 (Thr) as shown in SEQ ID NO:2; (c) the polypeptide shown from residues 24 (Thr) to 164 (Thr) as shown in SEQ ID NO:2; and (d) the polypeptide shown from residues 1 (Met) to 164 (Thr) as shown in SEQ ID NO:2. In another embodiment the antibody is as disclosed above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for inhibiting IL-31-induced proliferation or differentiation of hematopoietic cells and hematopoietic cell progenitors comprising culturing bone marrow or peripheral blood cells with a composition comprising an amount of an antibody as disclosed herein sufficient to reduce proliferation or differentiation of the hematopoietic cells in the bone marrow or peripheral blood cells as compared to bone marrow or peripheral blood cells cultured in the absence of soluble cytokine receptor. In one embodiment the method for inhibiting IL-31-induced proliferation or differentiation of hematopoietic cells and hematopoietic cell progenitors is as disclosed above, wherein the hematopoietic cells and hematopoietic progenitor cells are lymphoid cells. In another embodiment the method for inhibiting IL-31-induced proliferation or differentiation of hematopoietic cells and hematopoietic cell progenitors is as disclosed above, wherein the lymphoid cells are macrophages or T cells.

Within another aspect, the present invention provides a method of reducing IL-31-induced induced inflammation comprising administering to a mammal with inflammation an amount of a composition of a an antibody as disclosed herein sufficient to reduce inflammation.

Within another aspect, the present invention provides a method of suppressing an inflammatory response in a mammal with inflammation comprising: (1) determining a level of an inflammatory molecule; (2) administering a composition comprising an antibody as disclosed herein in an acceptable pharmaceutical vehicle; (3) determining a post administration level of the inflammatory molecule; (4) comparing the level of the inflammatory molecule in step (1) to the level of the inflammatory molecule in step (3), wherein a lack of increase or a decrease the inflammatory molecule level is indicative of suppressing an inflammatory response. In one embodiment, the antibody is as disclosed above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for inhibiting IL-31-induced proliferation or differentiation of hematopoietic cells and hematopoietic cell progenitors comprising culturing bone marrow or peripheral blood cells with a composition comprising an amount of an antibody as disclosed herein sufficient to reduce proliferation or differentiation of the hematopoietic cells in the bone marrow or peripheral blood cells as compared to bone marrow or peripheral blood cells cultured in the absence of soluble cytokine receptor. In one embodiment the method for inhibiting IL-31-induced proliferation or differentiation of hematopoietic cells and hematopoietic cell progenitors is as disclosed above, wherein the hematopoietic cells and hematopoietic progenitor cells are lymphoid cells. In another embodiment the method for inhibiting IL-31-induced proliferation or differentiation of hematopoietic cells and hematopoietic cell progenitors is as disclosed above, wherein the lymphoid cells are macrophages or T cells.

Within another aspect, the present invention provides a method of reducing IL-31-induced induced inflammation comprising administering to a mammal with inflammation an amount of a composition of a an antibody as disclosed herein sufficient to reduce inflammation.

Within another aspect, the present invention provides a method of suppressing an inflammatory response in a mammal with inflammation comprising: (1) determining a level of an inflammatory molecule; (2) administering a composition comprising an antibody as disclosed herein in an acceptable pharmaceutical vehicle; (3) determining a post administration level of the inflammatory molecule; (4) comparing the level of the inflammatory molecule in step (1) to the level of the inflammatory molecule in step (3), wherein a lack of increase or a decrease in the inflammatory molecule level is indicative of suppressing an inflammatory response.

Within another aspect, the present invention provides a method of treating a mammal afflicted with an inflammatory disease in which IL-31 plays a role, comprising: administering an antagonist of IL-31 to the mammal such that the inflammation is reduced, wherein the antagonist is selected from the group consisting of an antibody or binding polypeptide that specifically binds a polypeptide or polypeptide fragment of IL-31 (SEQ ID NO:2). In one embodiment, the method of treating a mammal afflicted with an inflammatory disease is as disclosed above, wherein the disease is a chronic inflammatory disease. In another embodiment, the method of treating a mammal afflicted with an inflammatory disease is as disclosed above, wherein the disease is a chronic inflammatory disease selected from the group consisting of: inflammatory bowel disease; ulcerative colitis; Crohn's disease; atopic dermatitis; eczema; and psoriasis. In anther embodiment, the method of treating a mammal afflicted with an inflammatory disease is as disclosed above, wherein the disease is an acute inflammatory disease. In another embodiment, the method of treating a mammal afflicted with an inflammatory disease is as disclosed above, wherein the disease is an acute inflammatory disease selected from the group consisting of: endotoxemia; septicemia; toxic shock syndrome; and infectious disease. In another embodiment, the method of treating a mammal afflicted with an inflammatory disease is as disclosed above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for detecting inflammation in a patient, comprising: obtaining a tissue or biological sample from a patient; incubating the tissue or biological sample with an antibody as disclosed herein under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of inflammation in the patient.

Within another aspect, the present invention provides a method for detecting inflammation in a patient, comprising: obtaining a tissue or biological sample from a patient; labeling a polynucleotide comprising at least 14 contiguous nucleotides of SEQ ID NO:1 or the complement of SEQ ID NO:1; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase in labeled polynucleotide hybridization to the patient tissue or biological sample relative to the normal control tissue or biological sample is indicative of inflammation in the patient.

The invention is further illustrated by the following non-limiting examples.

EXAMPLES

Example 1

Generation of Rat Anti-Mouse IL-31 MAbs

A. Immunization and Serum Screening of Rats

Four 3 month old female Sprague-Dawley rats (Charles River Laboratories, Wilmington, Mass.) were immunized with mouse IL-31. The rats were initially immunized by intraperitoneal injection with ~290 ug of purified, recombinant mouse IL-31 (produced in BHK cells) fused at the C-terminus with a peptide consisting of the sequence EYMPME (SEQ ID NO: 7) (hereafter referred to as mIL31-CEE) in combination with Complete Freund's Adjuvant (Pierce, Rockford, Ill.) as per manufacturer's instructions. Following the initial immunization each of the rats received an additional 150 ug of mIL-31-CEE in Incomplete Freund's Adjuvant via the intraperitoneal route every two weeks over a six week period. Seven days after the third and fourth immunizations the rats were bled via the retroorbital plexus and the serum separated from the blood for analysis of its ability to bind to mIL-31-CEE in solution and to inhibit (as measured by neutralization) the stimulatory activity of mIL-31-CEE on a cell line transfected with the mouse IL-31RA.

The ability of the rat anti-mouse IL-31 antibodies in the antisera to bind to mIL-31-CEE was assessed using a "capture" style ELISA assay. In this assay, wells of 96 well polystyrene ELISA plates were first coated with 100 uL/well of goat anti-rat IgG, Fc specific antibody (Jackson Immunoresearch) at a concentration of 500 ng/mL in 0.1M $Na_2CO_3$, pH 9.6. Plates were incubated overnight at 4° C. after which unbound antibody was aspirated and the plates washed twice with 300 uL/well of PBS-Tween (0.137M NaCl, 0.0027M KCl, 0.0072M $Na_2HPO_4$, 0.0015M $KH_2PO_4$, 0.05% v/v polysorbate 20, pH 7.2). Wells were blocked with 200 uL/well of SuperBlock (Pierce, Rockford, Ill.) for 5 minutes at room temperature (RT), the SuperBlock flicked off the plate and the block repeated once more after which the plates were washed twice with PBS-Tween. Serial 10-fold dilutions (in PBS-Tween plus 1% w/v bovine serum albumin (BSA) and 0.05% v/v Proclin 300, pH 7.2=dilution buffer) of the sera were prepared beginning with an initial dilution of 1:1000 and ranged to 1:1,000,000. Triplicate samples of each dilution were then transferred to the assay plate, 100 uL/well, in order to bind rat IgG in the sera to the assay plate through the Fc portion of the molecule. Normal rat sera served as a negative control. Following a 1 hour incubation at RT, the wells were aspirated and the plates washed twice as described above. Biotinylated mIL-31-CEE (12:1 molar ratio of biotin:protein) at a concentration of 500 ng/mL was then added to the wells, 100 uL/well. Following a 1 hour incubation at RT, unbound biotinylated mIL-31-CEE was aspirated from the wells and the plates washed twice. Horseradish peroxidase labeled streptavidin (Pierce, Rockford, Ill.) at a concentration of 500 ng/mL was then added to each well, 100 uL/well, and the plates incubated at RT for 1 hour. After removal of unbound HRP-SA, the plates were washed 5 times, 100 uL/well of tetramethyl benzidine (TMB) (BioFX Laboratories, Owings Mills, Md.) added to each well and the plates incubated for 5 minutes at RT. Color development was stopped by the addition of 100 uL/well of 450 nm TMB Stop Reagent (BioFX Laboratories, Owings Mills, Md.) and the absorbance values of the wells read on a Molecular Devices Spectra MAX 340 instrument at 450 nm.

The ability of the rat anti-mouse IL-31 antibodies in the antisera to inhibit (as measured by neutralization) the stimulatory activity of mouse IL-31 through its cognate receptor was assessed using a cell based neutralization assay that employed a mIL-31RA/OSMRbeta transfected Baf3 cell line with a luciferase reporter system (Baf3/KZ134/mcytor17/mOSMRbeta) and could be activated via stimulation of the cells by mouse IL-31. For this assay, an initial 1:250 dilution in assay media (RPMI 1640, 10% FBS, 2 mM L-glutamine, 1 mM sodium pyruvate, 1× penicillin-streptomycin-neomycin (Invitrogen, Carlsbad, Calif.)) of each antiserum was prepared and then each of these was serial 2-fold diluted to a final dilution of 1:32000. To each dilution of antisera was added an equal volume of mIL-31-CEE diluted to 4 ng/mL in assay buffer for a total of volume of 100 uL in the wells. The antibody/cytokine mixtures were incubated at RT for 0.5 hour after which the target cells were washed from their growth media, adjusted to a density of 300,000 cells/mL and added to the antibody/cytokine mixtures, 100 uL/well. Assay media containing 2 ng/mL of mIL-31 and no antisera served as a negative control and indicated the maximal stimulation that could be achieved in the assay. Following incubation at 37° C., 5% $CO_2$ for 16-24 hours the plates were centrifuged at 1500 RPM for 5 minutes, the media carefully flicked off and 25 uL of 1× cell lysis buffer (Promega, Madison, Wis.) added to each well. The plates were gently shaken for 10 minutes at RT to allow for complete cell lysis and then cell lysates were transferred to solid white 96-well plates (Corning/Costar 3917, Acton, Mass.). 40 uL of luciferase assay substrate (Promega) was added to each well. Wells were then assessed for luciferase activity (representing IL-31 activation of the STAT reporter construct) on a luminometer using a 5 second integration interval.

Both the "capture" ELISA assay as well as the cell based neutralization assay indicated that all four rats developed a significant antibody response to mIL-31 although one rat clearly generated a stronger response than the others. In general, the response as measured by the "capture" ELISA closely paralleled that seen with the cell based neutralization assay suggesting that IgG class antibody was primarily responsible for the inhibition of mIL-31.

B. Fusion

Four weeks after the last intraperitoneal immunization, the rat with the most significant mIL-31 neutralization titer was immunized a final time with approximately 150 ug of mIL-31-CEE in PBS via intravascular injection. Five days later, the spleen and lymph nodes of this rat were harvested, prepared into a single cell suspension and fused to the Sp2/0 mouse myeloma cell line (Shulman, M. et al., Nature 276:269-270, 1976) at a 4:1 lymphoid cell:myeloma cell ratio with PEG 1500 using standard methods known in the art (Harlow, E. and Lane, D. 1988. "Antibodies A Laboratory Manual", Cold Spring Harbor Laboratory, Cold Spring Harbor, N.Y.). The fusion mixture was distributed into a series of 96 well flat-bottomed plates in combination with BALB/c thymocytes as a feeder layer (Oi, V. T. and Herzenberg, L. A. 1980. "Selected Methods in Cellular Immunology", B. B. Mishell and S. M. Shiigi, eds., pp. 351-372, Freeman, San Francisco). Wells of the fusion plates were fed once with a 70% replacement of media and thymocytes after 4 days and again two days later with just media. Wells were assayed eight days after plating of the fusion.

C. Screening of the Fusion

The "capture" ELISA for mIL-31 as described above was used as the primary screen except that hybridoma supernatants were tested undiluted and were replica plated onto the assay plates from the culture plates. Approximately 170 positive wells were identified. Supernatants from each of these wells as well as a few negative wells were then assessed for their ability to inhibit mIL-31 in the cell based neutralization assay described earlier. Each was tested at a 1:8 final dilution in assay media. At the latter dilution, non-specific stimulatory components in the hybridoma supernatants were sufficiently reduced such that they were of minimal contribution to the stimulation index observed. A majority of the supernatants appeared to neutralize mIL-31 to some degree with approximately ten of them demonstrating essentially complete neutralization and the remainder showing a continuum of inhibition up to a point where approximately another ten appeared to possess very little if any neutralization potential. Hybridoma cells in approximately 150 of the "capture" ELISA positive wells were successfully expanded into culture in 24 well plates. When the density of the 24 well cultures was approximately $4-6 \times 10^5$ cells/mL, the supernatant (approximately 1.5 mL) was individually collected and stored for each well and the cells from each well cryopreserved.

Each of the 24 well supernatants was reanalyzed in both the "capture" ELISA and cell-based IL-31 neutralization assays employed in the fusion screen. In addition, these supernatants were also tested in a "capture" ELISA employing the human homolog of IL-31 also constructed with the EYMPME (SEQ ID NO: 7) tag fused to the C-terminal of the IL-31 molecule and produced in BHK cells. Results indicated that following expansion, a majority of the master well supernatants had retained their ability to recognize mouse IL-31 in solution. Among these "capture" assay positive wells, the mIL-31 inhibitory activity ranged from complete to nearly complete for about 20 supernatants to essentially no inhibition for 10-15 supernatants. No crossreactivity to human IL-31-CEE was observed in the capture assay indicating that none of the rat anti-mIL-31 antibodies crossreacted with the human IL31 homolog or recognized the CEE tag fused to the C-terminal of the mIL-31-CEE molecule.

D. Selection and Cloning of Hybridomas Producing Neutralizing Anti-mIL31 MAbs

Cells in seven of the top ten IL-31 neutralizing master wells (271.5.7, 271.9.4, 271.26.6, 271.27.4, 271.33.1, 271.33.3 and 271.39.4) were cloned in order to isolate a cloned hybridoma producing the neutralizing mAb of interest. Cells were cloned in the presence of thymocytes in 96 well microtiter cell culture plates using a standard low-density dilution (less than 1 cell per well) approach and monoclonality was assessed by microscopic examination of wells for a single foci of growth prior to assay. Six days post-plating, all wells on the plates were screened by the "capture" ELISA for mIL-31 specific IgG. Supernatant from 6-10 wells that was both positive for specific mAb and originated from wells with only a single colony of hybridoma growth was collected from each cloning set and rescreened at various dilutions in the "capture" ELISA as well as the cell-based neutralization assay to identify a "best" neutralizing mAb producing clone. Results of these tests indicated that the appropriate neutralizing mAb producing hybridoma clones were obtained only in sets 271.9.4, 271.26.6, 271.33.1, 271.33.3 and 271.39.4. A "best" clone in each of these sets was recloned and the subclones screened as described to yield the final hybridoma lines 271.9.4.2.6, 271.26.6.6.1, 271.33.1.2.2, 271.33.3.2.1 and 271.39.4.6.5. The rat IgG isotype of the mAb produced by each of these hybridomas was determined using an ELISA that employed biotinylated mouse anti-rat IgG isotype specific mAbs. All five mAbs were found to belong to the IgG1 subclass. Hybridoma 271.26.6.6.1 was deposited with the American Type Tissue Collection (ATCC, Manassas, Va.) patent depository as an original deposit under the Budapest Treaty and given ATCC Accession No. PTA-6874.

Each of the fully cloned anti-mouse IL-31 mAb producing hybridomas was adapted to growth in hybridoma serum free medium (Hybridoma-SFM, Invitrogen). Supernatant from high cell density cultures grown in Hybridoma-SFM was centrifuged to remove cells and cell debris, filtered through a 0.2 µm filter and the mAb purified by protein G chromatography using standard methods known in the art.

E. Ranking In Vitro Specific Neutralizing Activity of MAbs

To rank the in vitro specific neutralizing activity of each of the five rat anti-mouse IL-31 mAbs, each of the purified mAbs was retested in the cell-based neutralization assay described earlier with the exception that mIL-31 was first added to cells and this mixture then added to the antibodies. In addition to neutralizing activity against mIL-31-CEE, the mAbs were also evaluated against another form of mouse IL-31, termed c108smIL-31, in which the cysteine residue at position 108 had been converted to a serine residue. The latter material was produced in $E.\ coli$ without the C-EE peptide. Both forms of mIL-31 were employed at a final concentration of 1 and 5 ng/mL. The mAbs were adjusted to a concentration of 20 ug/mL in assay media and tested in duplicate as serial 10-fold dilutions ranging from 10 ug/mL to 0.00001 ug/mL final concentration in the assay mixture. IC50 values were determined using Softmax software (Molecular Devices). Results are shown in Table 1 and show that mAbs 271.26.6.6.1, 271.33.1.2.2 and 271.39.4.6.5 were the most potent neutralizing mAbs and were of similar potency in this in vitro test. Interestingly, mAb 271.33.3.2.1 was much less effective than the other mAbs against the c108smIL-31 version of mIL-31 supporting the conclusion from the epitope binning studies that this antibody in all likelihood has a different epitope specificity than the other four mAbs. The fact that this mAb was also much less effective against the c108smIL-31 version of mIL-31 as compared to the mIL-31-CEE version suggests that the epitope recognized by 271.33.3.2.1 might partially involve a glycosylation site on the IL-31 molecule.

TABLE 1

| In Vitro Cell-Based Neutralization Activity of Rat Anti-Mouse IL-31 MAbs | | | | | | |
|---|---|---|---|---|---|---|
| mIL-31 | Conc. | IC50 (ng/mL) for mAbs | | | | |
| version | (ng/mL) | 271.9.4.2.6 | 271.26.6.6.1 | 271.33.1.2.2 | 271.33.3.2.1 | 271.39.4.6.5 |
| mIL31-CEE | 1 | 11 | 3 | 2 | 13 | 2 |
|  | 5 | 30 | 14 | 13 | 36 | 12 |
| c108smIL31 | 1 | 96 | 11 | 7 | 1248 | 9 |
|  | 5 | 190 | 43 | 33 | 2551 | 40 |

Example 2

Generation of Mouse Anti-Human IL-31 mAbs

A. Immunization and Serum Screening of Mice

Two groups of six to eight week old female BALB/c mice, five animals each, were immunized with human IL-31. Mice in Group 1 were immunized by intraperitoneal injection of purified, recombinant human IL-31 fused at the C-terminal with a peptide consisting of the sequence EYMPME (SEQ ID NO: 7) (hereafter referred to as IL-31-CEE) in combination with Ribi adjuvant as per manufacturer's instructions. This protein was produced in BHK cells. Mice in Group 2 were similarly immunized with a purified, recombinant, mutated form of human IL-31 in which the cysteine residue at position 108 had been converted to a serine residue (hereafter referred to as c108sIL-31). This material was produced in *E. coli* without the C-EE peptide. All mice received 50 ug of protein every two weeks for a 10 week period. Seven to ten days after the third and fourth immunizations the mice were bled via the retroorbital plexus and the serum separated from the blood for analysis of its ability to inhibit the binding and subsequent stimulatory activity of human IL-31 to a cell line transfected with the human IL-RA.

The ability of the individual antisera to inhibit human IL-31 was assessed using a luciferase based neutralization assay employing IL-31-CEE or c108sIL-31 and BaF3/KZ134/IL-31RA/OSMRbeta cells (see Examples 3 and 4) with the following modifications. Individual antisera were titrated in duplicate, via serial 4-fold dilutions down a 96 well, flat bottomed, white polystyrene plate (Corning/Costar 3917) starting with an initial 1:250 dilution of the antisera in assay buffer (RPMI 1640, 10% FBS, 1 mM sodium pyruvate, 2 mM L-glutamine, 100 U/mL penicillin G sodium, 100 ug/mL streptomycin sulfate). In an attempt to normalize the somewhat stimulatory effect of mouse serum in this assay, all dilutions except the initial 1:250 dilution were carried out in assay buffer plus 0.2% normal BALB/c mouse serum. The volume of diluted antisera in each well was 100 uL. Cells were washed 1.5 times in assay buffer, adjusted to a concentration of 3×106/mL, combined with either IL-31-CEE (100 pg/mL) or c108 μL-31 (30 pg/mL) and the mixture then added to the plates, 100 uL/well. Total assay volume was 200 uL/well consisting of 30,000 cells, IL-31 at a final concentration of 50 pg/mL (IL-31-CEE) or 15 pg/mL (c108sIL-31) and antisera at a final dilution of 1:500, 1:2000, 1:8000, 1:32000, 1:128000, 1:512000, 1:2048000 and 1:8192000. Plates were incubated at 37° C., 5% $CO_2$ for 16-24 hours after which they were centrifuged at 1250 RPM for 5 minutes, the media carefully flicked off and 25 uL of 1× cell lysis buffer added to each well. The plates were gently shaken for 10 minutes to allow for cell lysis after which 40 uL of luciferase assay substrate was added to each well. Wells were then assessed for luciferase activity (representing IL-31 activation of the STAT reporter construct) on a luminometer using a 4 second integration interval.

In general the antisera from mice immunized with IL-31-CEE was found to effectively inhibit the stimulatory activity of both IL-31-CEE and c108sIL-31 and vice versa, in this assay. For this reason, further neutralization assays were usually carried out with only IL-31-CEE.

Those mice with the strongest neutralizing titers were used for a series of three fusions aimed at generating hybridomas producing monoclonal antibodies that could very effectively neutralize the interaction of IL-31 with its cognate receptor.

B. Fusions

Fusion 291

The first fusion employed lymphoid node cells from one mouse immunized with IL-31-CEE and one mouse immunized with c108sIL-31. Each of these animals was immunized for a sixth time with 15 ug of the respective immunogen diluted in PBS and administered via intravascular injection three weeks after their last immunization. Three days later, the spleen and lymph nodes from these mice were harvested, combined, processed into a single cell suspension (total of 4.69×10$^8$ cells) and then fused to a clone of the mouse myeloma cell line P3-X63-Ag8.653 (Kearney, J. F. et al., J. Immunol. 123:1548-50, 1979) (designated P3-X63-Ag8.653.3.12.11) at a 2.3:1 lymphoid cell:myeloma cell ratio with 3 mL PEG 1500 for 2 minutes 55 seconds using standard methods known in the art (Lane, R. D. J Immunol Methods 81:223-8, 1985). The fusion mixture was distributed into a series of 96 well flat-bottomed plates, fed once with a 70% media replacement after 4 days and assayed 6 days later.

Fusion 292

The second fusion employed lymphoid cells from one mouse immunized with IL-31-CEE. In addition to the five intraperitoneal immunizations mentioned above, this mouse received an intravascular injection of 15 ug of IL-31-CEE in PBS three weeks after the last intraperitoneal injection and a similar injection three weeks after the first intravascular immunization. Three days later, the spleen and lymph nodes were processed (total of 2.27×10$^8$ cells) and fused to P3-X63-Ag8.653.3.12.11 at a 2:1 lymphoid cell:myeloma cell ratio with 1.8 mL PEG 1500 for 2 minutes 55 seconds as described above. The fusion mixture was distributed into a series of 96 well flat-bottomed plates, fed once with a 70% media replacement after 4 days and assayed 5 days later.

Fusion 294

The last fusion employed lymphoid cells from one mouse immunized with c108sIL-31 only. In addition to the five intraperitoneal immunizations with this antigen described earlier, this mouse received an intravascular injection of 15 ug of c108sIL-31 in PBS six weeks after the last intraperitoneal injection and then again two weeks after the first intravascular injection. Three days later, the spleen and lymph nodes were processed (total of 1.586×10$^8$ cells) and fused to P3-X63-Ag8.653.3.12.11 at a 2:1 lymphoid cell:myeloma cell ratio with 1.5 mL PEG 1500 for 2 minutes 55 seconds as described above. The fusion mixture was distributed into a series of 96 well flat-bottomed plates, fed twice with a 70% media replacement after 4 and 6 days and assayed 3 days after the last feed.

C. Screening of Fusions

All three fusions were screened using the cell-based IL-31 neutralization assay described above with two modifications. First, instead of diluted antisera in the assay plates, 100 uL of supernatant from each of the wells on the fusion plates was replica plated onto the assay plates. Second, the final concentration of IL-31-CEE in the assay mixture was 150 pg/mL.

In addition to the neutralization assay, several plates from each fusion, chosen at random, were screened for IgG antibodies that could bind to IL-31-CEE that had previously been adsorbed onto polystyrene ELISA plates. The purpose of this assay was to identify master wells containing a hybridoma producing an anti-IL31 antibody that either poorly neutralized IL-31 or completely failed to neutralize this cytokine. In this assay, wells of 96 well polystyrene ELISA plates were initially coated with 50 uL/well of IL31-CEE at a concentration of 200 ng/mL in 0.1M Na2CO3, pH 9.6. Plates were incubated overnight at 4° C. after which unbound antigen was aspirated and the plates washed twice with 300 uL/well of PBS-Tween (0.137M NaCl, 0.0027M KCl, 0.0072M Na2HPO4, 0.0015M KH2PO4, 0.05% v/v polysorbate 20, pH 7.2). Wells were blocked with 200 uL/well of PBS-Tween+1% BSA for 1 hour at room temperature (RT). Blocking solution was then flicked off the plates and 50 uL of conditioned media from each well of the fusion plates replica plated into the wells of the assay plate. Plates were incubated for 1 hour at RT after which unbound antibody was aspirated and the plates washed twice with 300 uL/well of PBS-Tween. HRP conjugated goat anti-mouse IgG, Fc specific antisera (Jackson Immunoresearch) was diluted 1:5000 in PBS-Tween+1% BSA and added to wells of the assay plates, 100 uL/well. Following a 1 hour incubation at RT, unbound second step antibody was aspirated from the wells and the plates washed 5 times. 100 uL/well of tetramethyl benzidine (TMB) (BioFX Laboratories, Owings Mills, Md.) was then added to each well and the plates incubated for 5 minutes at RT. Color development was stopped by the addition of 100 uL/well of 450 nm TMB Stop Reagent (BioFX Laboratories, Owings Mills, Md.) and the absorbance values of the wells read on a Molecular Devices Spectra MAX 340 instrument at 450 nm.

Results of the neutralization assays showed that 52 and 139 wells in Fusion 291 and 292, respectively, contained an antibody that inhibited at least 40% of the IL-31 stimulatory activity. A more stringent definition of positivity was applied to fusion 294 where it was observed that 131 wells contained an antibody that inhibited at least 70% of the IL-31 activity. Results of ELISA assays to detect mAbs that bound to IL-31-CEE indicated that in a majority of cases, if a master well was found to contain an IgG antibody that bound to IL-31-CEE, it also contained an antibody that inhibited IL-31-CEE in the cell-based neutralization assay. There were some wells, however, that were positive in the ELISA assay but which showed relatively weak inhibitory capacity in the cell-based neutralization assay and they were saved for later analysis as described below.

Hybridoma cells growing in the positive master wells were expanded into culture in 24 well plates. When the density of the 24 well cultures was approximately $4-6 \times 10^5$ cells/mL, the supernatant (approximately 1.5 mL) was individually collected and stored for each well and the cells from each well cryopreserved.

D. Selection and Cloning of Master Wells to Isolate Hybridomas Producing Potent IL-31 Neutralizing MAbs Each of the new 24 well supernatants was reanalyzed for IL-31 neutralization capacity using the cell-based IL-31 neutralization assay employed in the fusion screen. Each supernatant was run undiluted and in duplicate. Results indicated that following expansion, a majority of the master well supernatants had retained inhibitory activity equal to or better than that observed in the original master screen. To better determine which of the new master well supernatants possessed the strongest inhibitory capacity, those supernatants that demonstrated approximately 90% or better inhibition of IL-31-CEE in this assay were reanalyzed by testing dilutions of the supernatant in the cell-based neutralization assay. Supernatants were titrated via serial 3-fold dilutions into fusion media on the assay plates to yield 100 uL in each well of the following dilutions: neat, 1:3, 1:9, 1:27, 1:81 and 1:243 and the assay carried out as described above for the fusion screen. While this assay clearly identified the most inhibitory supernatants, it was unable to determine which ones had the highest specific activity because concentration of anti-IL31 antibody in the supernatants was unknown.

To address the specific antibody concentration issue, each of the supernatants was tested in titration format, using either serial 2-fold or 4-fold dilutions, on IL-31-CEE in the direct ELISA assay described above. After plotting the data in Microsoft EXCEL, the dilution of supernatant yielding half the maximal optical density (OD) observed in the assay was determined which in turn provided some indication of the relative concentration of anti-IL-31 antibody in the supernatant.

By combining the data from the neutralization assay with that of the ELISA assay, a relative specific activity was established for each supernatant and the twenty master wells containing the highest anti-IL-31 neutralization specific activity identified. Interestingly, all the most potent anti-IL-31 neutralizing master wells were derived from fusion 292. It was noted in the neutralization data for these master wells that while maximal IL-31 inhibition was achieved for each supernatant at the neat and 1:3 dilution, the absolute degree of neutralization was slightly greater for some supernatants than others as reflected in slightly lower relative luciferase unit counts. This was interpreted as slightly different degrees of "complete" IL-31 neutralization. By coupling this observation with the relative neutralization specific activity for each master well, the list of the twenty most potent neutralizing master wells was reduced to the apparent best ten. These included 292.12, 292.39, 292.51, 292.63, 292.64, 292.72, 292.84, 292.105, 292.109 and 292.118.

Cells in each of these top ten IL-31 neutralizing master wells were cloned in order to isolate a cloned hybridoma producing the neutralizing mAb of interest. Cells were cloned in 96 well microtiter cell culture plates using a standard low-density dilution (less than 1 cell per well) approach and monoclonality was assessed by microscopic examination of wells for a single foci of growth prior to assay. Cloning media consisted of fusion media lacking the HAT component (IMDM, 10% FC1 serum, 2 mM L-glutamine, 1× penicillin/streptomycin, 10% hybridoma cloning factor (Roche Applied Science). Six to eight days post-plating, supernatants in all wells were screened by ELISA on plate bound IL-31-CEE. Cells from 4-6 wells in each set in which the supernatant was strongly positive for specific mAb and there appeared to be only a single colony of hybridoma growth were expanded into 24 well cultures and resulting supernatants retested by ELISA on plate bound IL-31-CEE and by the cell-based IL-31 neutralization assay. Based on these results the apparent most potent neutralizing clone in each set was recloned and screened by ELISA as described above. If 95% or more of the growth positive wells were also positive for specific mAb, further subcloning efforts were deemed unnecessary and the hybridomas declared clonal. For only one master well, 292.64, was a second round of subcloning necessary to achieve the desired percentage of specific mAb positivity among the resulting clones. Cells from 5-6 wells in each final subclone set in which the supernatant was strongly positive for specific mAb and there appeared to be only a single colony of hybridoma growth were expanded into 24 well cultures. Each of the hybridoma clones was then adapted to growth in media lacking hybridoma cloning factor (IMDM, 10% FC1 serum, 2 mM L-glutamine, 1× penicillin/streptomycin) by splitting cells into the latter media when cell density was appropriate. Following adaptation, supernatant was collected from the subclones in each set and screened by ELISA on plate bound IL-31-CEE. Based on titer with respect to cell density at the time of supernatant collection, a "best" final clone was chosen leading to the selection of the following group of final clones: 292.12.3.1; 292.39.5.3; 292.51.5.2; 292.63.5.3; 292.64.6.5.5; 292.72.3.1; 292.84.1.6; 292.105.4.1; 292.109.4.4; and 292.118.6.4.

The mouse IgG isotype of the mAb produced by each of these hybridomas was determined using the Mouse Monoclonal Antibody IsoStrip test (Roche Applied Science). All of the mAbs were found to belong to the IgG1 subclass except for 292.72.3.1 and 292.84.1.6 which were shown to belong to the IgG2a subclass.

E. Ranking In Vitro Specific Neutralizing Activity of Potent IL-31 Neutralizing MAbs To rank the in vitro specific neutralizing activity of the ten potent mouse anti-human IL-31 mAbs, exhausted supernatant from each of the first round clones was retested in the cell-based neutralization assay described earlier. First, the amount of IgG in each supernatant was determined by HPLC analysis on a protein G column using a mAb of known concentration as a standard. Each supernatant was then diluted to an IgG concentration of 1 ug/mL in the same media used to generate the exhausted supernatant. The diluted supernatants were then titrated via 10-fold serial dilution in media to yield a concentration range of 1 ug/mL to 0.0001 ug/mL and tested in triplicate in the previously described cell-based neutralization assay with the final concentration of IL-31-CEE set at 300 pg/mL (18.27 µM). Results of the assay are shown in Table 2 with the mAbs listed in order from most potent to least potent. MAbs 292.84.1 and 292.12.3 were the most potent neutralizers followed in turn by mAbs 292.72.3 and 292.63.5 which appeared to be approximately half as potent as the former two. The remainder of the mAbs were shown to be approximately 6-9 times less potent than the two best mAbs.

TABLE 2

Ranking of the Potent Anti-IL31 Neutralizing MAbs by in vitro Specific Neutralization Activity

| MAb | $IC_{50}$ (ng/mL) | $IC_{50}$ (pM)* |
|---|---|---|
| 292.84.1 | 1.077 ± 0.021 | 7.18 ± 0.14 |
| 292.12.3 | 1.197 ± 0.044 | 7.98 ± 0.29 |
| 292.72.3 | 1.997 ± 0.027 | 13.31 ± 0.18 |
| 292.63.5 | 2.819 ± 0.034 | 18.79 ± 0.23 |
| 292.51.5 | 6.478 ± 0.130 | 43.19 ± 0.87 |
| 292.118.6 | 6.550 ± 0.154 | 43.67 ± 1.03 |
| 292.109.4 | 8.286 ± 0.151 | 55.24 ± 1.01 |
| 292.39.5 | 8.633 ± 0.481 | 57.55 ± 3.20 |
| 292.105.4 | 9.144 ± 0.281 | 60.96 ± 1.87 |
| 292.64.6 | 10.05 ± 0.295 | 67.00 ± 1.97 |

*using a molecular weight of antibody = 150,000 daltons

Based on the above results, hybridomas 292.84.1.6, 292.12.3.1, 292.72.3.1, 292.63.5.3 and 292.118.6.4 were chosen as representative of the different levels of specific neutralization capacity to be deposited with the American Type Tissue Collection (ATCC, Manassas, Va.) patent depository as an original deposit under the Budapest Treaty and were given the following ATCC Accession Nos.: clone 292.12.3.1 (ATCC Patent Deposit Designation PTA-6815); clone 292.72.3.1 (ATCC Patent Deposit Designation PTA-6816); clone 292.63.5.3 (ATCC Patent Deposit Designation PTA-6829); clone 292.118.6.4 (ATCC Patent Deposit Designation PTA-6830); and clone 292.84.1.6 (ATCC Patent Deposit Designation PTA-6871).

F. Selection and Cloning of Master Wells to Isolate Hybridomas Producing Poor IL-31 Neutralizing MAbs Of interest in the generation of anti-human IL-31 mAbs was the isolation of pairs of mAbs that could be used in a sandwich assay format to quantify the amount of IL-31 in different fluids. Such pairs of mAbs typically have specificity for different epitopes on the target molecule and preferably do not cross compete for binding to that molecule. To isolate candidate pairs of such mAbs, a strategy was chosen to pair an excellent IL-31 neutralizing mAb with one possessing little if any neutralization potential, assuming that two such different functional antibodies in all likelihood bound to non-overlapping (spatially separated) epitopes.

As noted earlier for the fusion screens, several plates from each fusion were screened by ELISA on plate bound IL-31-CEE to identify anti-IL-31 antibody positive master well supernatants. Comparison of the ELISA results to those of the cell-based neutralization assay indicated the presence of master wells that contained antibody that bound well to IL-31-CEE but did not neutralize this molecule very well in the cell-based neutralization assay. As was done with the more potent neutralizing master wells, hybridoma cells growing in these master wells were expanded into culture in 24 well plates. When the density of the 24 well cultures was approximately $4-6\times10^5$ cells/mL, the supernatant (approximately 1.5 mL) was individually collected and stored for each well and the cells from each well cryopreserved.

These new supernatants were tested using the cell-based neutralization assay (serial 3-fold dilutions starting with neat supernatant and proceeding to a final 1:243 dilution) as well as a "capture" style ELISA assay similar to that used in the development of the rat anti-murine IL-31 mAbs with the following differences; 1) sheep anti-mouse IgG, Fc specific antibody (Jackson Immunoresearch) (1 ug/mL) as plate coating antibody, 2) plates blocked once with PBS-Tween+1% BSA for 1 hr, 3) a single titration of each supernatant added to wells (serial 3-fold dilutions starting with neat supernatant and proceeding to a final 1:2187 dilution), and 4) addition of biotinylated IL-31-CEE (3:1 molar ratio of biotin:protein), 200 ng/mL. This assay was felt to be more pertinent than the binding of antibody to plate bound IL-31-CEE as it assessed the ability of antibody to bind to IL-31-CEE in solution, a property essential to a good antibody for sandwich style ELISAs. It was in fact observed that a number of the master wells supernatants containing antibody that bound well to plate bound IL-31-CEE poorly recognized this molecule in solution.

To chose which wells to clone appropriate antibody secreting hybridomas from, 10 wells were identified (291.78, 292.152, 292.154, 294.35, 294.144, 294.146, 294.154, 294.155, 294.158 and 294.163) whose supernatant poorly neutralized IL-31-CEE in the neutralization assay (less than 50% but preferably only 1-20%) and also bound relatively well to IL-31-CEE in solution (as noted by an OD of greater than 2.0 at neat concentration of supernatant). Cloning, screening of clones, and selection of a best first round clone was performed as described above for the potent neutralizing wells.

To reduce the number of hybridomas going into further subcloning, two new assays were performed with exhausted supernatant from each of the selected first round clones. The first assessment was an attempt to group the mAbs on the basis of epitope specificity ("binning") using the Biacore 3000 surface plasmon resonance instrument. One of the good neutralizing mAb supernatants (292.64.6) and the 10 poorer neutralizing first round clone supernatants were run against each other and resulted in the identification of four apparent "bins". Bin 1 consisted of the good neutralizing antibody only. Bin 2 was comprised of 292.152.4, 292.154.4, 294 35.2, 294.146.5 and 294.154.5. Bin 3 included 291.78.4, 294.155.6, 294.158.5 and 294.163.2. Bin 4 contained only 294.144.3. The second assay involved a repeat of the "capture" style ELISA only this time, because of higher specific antibody concentration in the supernatants as compared to the original master 24 well culture supernatants, a more complete titration curve was obtained and allowed for the determination of an EC50 for antibody binding to IL-31-CEE. Results are shown in Table 3 (along with the binning results and the % inhibition of IL-31-CEE activity in the cell-based neutralization assay) and indicated that there was a wide range in EC50 values (and by inference, affinity of the mAbs for IL-31-CEE) for the various mAbs.

TABLE 3

Summary Data for First Round Clone Culture Supernatant from Less Potent IL-31 Neutralizing Hybridomas

| MAb | Epitope Bin (Biacore) | $EC_{50}$ (ng/mL) for capture of IL31-CEE | % Neutralization of IL31 activity in cell-based assay (undiluted supernate) |
| --- | --- | --- | --- |
| 291.78.4 | 3 | 10 | 94 |
| 292.152.4 | 2 | 182 | 25 |
| 292.154.4 | 2 | 57.7 | 76 |
| 294.35.2 | 2 | 22.2 | 82 |
| 294.144.3 | 4 | 13.4 | 75 |
| 294.146.5 | 2 | 10.2 | 94 |
| 294.154.5 | 2 | 15.8 | 88 |
| 294.155.6 | 3 | 172 | 53 |
| 294.158.5 | 3 | 119 | 31 |
| 294.163.2 | 3 | 24.2 | 47 |
| 292.64.6 | 1 | 3.4 | 100 |

With emphasis on selection of hybridomas producing mAbs that were 1) in epitope bins different from that of a good neutralizing mAb (292.64.6) and 2) of highest affinity as indicated by a low EC50 in the capture style assay, only first round clones 294.35.2, 294.144.3, 294.154.5 and 294.163.2 were brought to final clone status as described above for the more potent neutralizing mAbs. This further subcloning effort yielded selection of the following group of final clones: 294.35.2.6.3; 294.144.3.5; 294.154.5.6; and 294.163.2.1.

The mouse IgG isotype of the mAb produced by each of these hybridomas was determined using the Mouse Monoclonal Antibody IsoStrip test (Roche Applied Science). All four mAbs were found to belong to the IgG1 subclass. Samples of each of the four hybridomas were deposited with the American Type Tissue Collection (ATCC, Manassas, Va.) patent depository as an original deposit under the Budapest Treaty and were given the following ATCC Accession Nos.: clone 294.163.2.1 (ATCC Patent Deposit Designation PTA-6831); clone 294.35.2.6.3 (ATCC Patent Deposit Designation PTA-6872); clone 294.154.5.6 ATCC Patent Deposit Designation PTA-6875); and clone 294.144.3.5 (ATCC Patent Deposit Designation PTA-6873).

G. Cross-Reaction of Mouse Anti-Human IL-31 mAbs with Mouse IL-31

All first round clone supernatants from the ten potent neutralizing mAbs as well as the ten less potent neutralizing mAbs were tested for their ability to recognize mouse IL-31 by ELISA on plate bound mIL-31-CEE. No cross-reactivity was seen with any of the mAbs indicating that the mAbs appeared to have specificity for human IL-31. Furthermore these results showed that none of the antibodies recognized the CEE peptide tag common to the C-terminal end of both the human and mouse IL-31 recombinant molecules used in these studies, a determination that was not made on the original master well supernatants.

Example 3

IL-31RA/OSMRbeta Receptor Luciferase Assay

The KZ134 plasmid was constructed with complementary oligonucleotides that contain STAT transcription factor binding elements from 4 genes, which includes a modified c-fos Sis inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and were ligated, using standard methods, into a recipient firefly luciferase reporter vector with a c-fos promoter (Poulsen, L. K. et al., *J. Biol. Chem.* 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

A stable BaF3/KZ134 indicator cell line, expressing the full-length IL-31RA or IL-31RA/OSMRbeta receptor was constructed. Clones were diluted, plated and selected using standard techniques. Clones were screened by luciferase assay (see B, below) using the human IL-31 conditioned media or purified IL-31 protein as an inducer. Clones with the highest luciferase response (via STAT luciferase) and the lowest background were selected. Stable transfectant cell lines were selected. The cell lines were called BaF3/KZ134/IL-31RA or BaF3/KZ134/IL-31RA/OSMRbeta depending on the receptors transfected into the cell line.

Similarly, BHK cell lines were also constructed using the method described herein, and were used in luciferase assays described herein. The cell lines were called BHK/KZ134/IL-31RA or BHK/KZ134/IL-31RA/OSMRbeta depending on the receptors transfected into the cell line.

BaF3/KZ134/IL-31RA and BaF3/KZ134/IL-31RA/OSMRbeta cells were spun down and washed in mIL-3 free media. The cells were spun and washed 3 times to ensure removal of mIL-3. Cells were then counted in a hemacytometer. Cells were plated in a 96-well format at about 30,000 cells per well in a volume of 100 μl per well using the mIL-3 free media. The same procedure was used for untransfected BaF3/KZ134 cells for use as a control in the subsequent assay. BHK/KZ134/IL-31RA or BHK/KZ134/IL-31RA/OSMRbeta cells were plated in a 96-well format at 15,000 cells per well in 100 μl media. Parental BHK/KZ134 cells were used as a control.

STAT activation of the BaF3/KZ134/IL-31RA, BaF3/KZ134/IL-31RA/OSMRbeta, BHK/KZ134/IL-31RA, or BHK/KZ134/IL-31RA/OSMRbeta cells is assessed using conditioned media or purified protein. One hundred microliters of the diluted conditioned media or protein is added to the BaF3/KZ134/IL-31RA, BaF3/KZ134/IL-31RA/OSMRbeta, BHK/KZ134/IL-31RA, or BHK/KZ134/IL-31RA/OSMRbeta cells. The assay using the conditioned media is done in parallel on untransfected BaF3/KZ134 or BHK/KZ134 cells as a control. The total assay volume is 200. The assay plates are incubated at 37° C., 5% $CO_2$ for 24 hours at which time the BaF3 cells are pelleted by centrifugation at 2000 rpm for 10 min., and the media is aspirated and 25 μl of lysis buffer (Promega) is added. For the BHK cell lines, the centrifugation step is not necessary as the cells are adherant. After 10 minutes at room temperature, the plates are measured for activation of the STAT reporter construct by reading them on a luminometer (Labsystems Luminoskan, model RS) which added 40 μl of luciferase assay substrate (Promega) at a five second integration.

Example 4

Luciferase Assay on Human Transformed Epithelial Cell Lines via Transient Infection with an Adenoviral STAT/SRE Reporter Gene Inhibition, reduction, and/or neutralization of IL-31 activity can be measured by the luciferase assay. For example, human transformed cell lines can be seeded in 96-well flat-bottom plates at 10,000 cell/well in regular growth media as specified for each cell type. The following day, the cells are infected with an adenovirus reporter construct, KZ136, at a multiplicity of infection of 5000. The KZ136 reporter contains the STAT elements in addition to a serum response element. The total volume is 100 ul/well using DMEM supplemented with 2 mM L-glutamine (GibcoBRL), 1 mM Sodium Pyruvate (GibcoBRL) and 1× Insulin-Transferrin-Selenium supplement (GibcoBRL) (hereinafter referred to as serum-free media). Cells are cultured overnight.

The following day, the media is removed and replaced with 100 µl of induction media. The induction media is human IL-31 diluted in serum-free media at 100 ng/ml, 50 ng/ml, 25 ng/ml, 12.5 ng/ml, 6.25 ng/ml, 3.125 ng/ml and 1.56 ng/ml. A positive control of 20% FBS is used to validate the assay and to ensure the infection by adenovirus is successful. The cells are induced for 5 hours at which time the media is aspirated. The cells are then washed in 50 µl/well of PBS, and subsequently lysed in 30 µl/well of 1× cell lysis buffer (Promega). After a 10-minute incubation at room temperature, 25 µl/well of lysate is transferred to opaque white 96-well plates. The plates are then read on the Luminometer using 5-second integration with 40 µl/well injection of luciferase substrate (Promega).

Example 5

Inhibition of Cytokine Production by IL-31 Antibodies

IL-31 has been shown to stimulate IL-6 production in DU145 (diseased and normal cell lines); as well as stimulate a A549 cell lines (diseased and normal) to stimulate IL-8 production, and to reduce IL-8 production in U2OS cell lines (diseased and normal). See published U.S. patent application (See publication number 20030224487, Sprecher, Cindy et al., 2003). As such the activity of the IL-31 monoclonal antibodies described herein can be measured by an inhibition, reduction, and/or neutralization of IL-31 activity in these human disease-state epithelial cell lines.

A. Inhibition of Cytokine Production by Human Disease-State Epithelial Cell Lines Cultured with Human IL-31

Cells are plated at a density of $4.5\times10^5$ cells per well in a 6 well plate (Costar) and cultured in respective growth media. The cells are cultured with test reagents; 100 ng/mL IL-31 (with and with out antibody challenge), 10 ng/mL Interferon gamma (IFN gamma) (R&D Systems, Minneapolis, Minn.), 10 ng/mL Tumor Necrosis Factor alpha (TNF alpha) (R&D Systems, Minneapolis, Minn.), 10 ng/mL IL-1beta (R&D Systems, Minneapolis, Minn.) or 100 ug/mL Lipopolysaccharide (LPS) (Sigma). Supernatants are harvested at 24 and 48 hours and assayed for cytokines; GM-CSF (Granulocyte-Macrophage Colony-Stimulating Factor), IL-1b, IL-6, IL-8, MCP-1 (Macrophage Chemoattractant Protein-1) and TNFa. Multiplex Antibody Bead kits from BioSource International (Camarillo, Calif.) were used to measure cytokines in samples. Assays are read on a Luminex-100 instrument (Luminex, Austin, Tex.) and data is analyzed using MasterPlex software (MiraiBio, Alameda, Calif.). Cytokine production (pg/mL) for each cell line in the 24-hour samples is measured.

B. Inhibition of Cytokine Production by Normal Human Epithelial Cell Lines Cultured with Human IL-31

Cells are plated at a density of $1\times10^5$ cells per well in a 24 well plate and cultured with test reagents; 1000 ng/mL, 100 ng/mL and 10 ng/mL IL-31 (with and with out antibody challenge), 10 ng/mL TNFa, 10 ng/mL OSM, 10 ng/mL IFNa, 10 ng/mL TGFb or 10 ng/mL Lymphotactin. Supernatants are harvested at 24 and 48 hours and assayed for cytokines; IL-6, IL-8, MCP-1, MIP-1a, RANTES and Eotaxin. Cytokines are assayed as previously described. Cytokine production (pg/mL) for each cell line in the 48-hour samples is measured.

C. Inhibition of Cytokine Production by Human Disease-State Epithelial Cell Lines Co-Cultured with Human IL 31 and IFN gamma Cells are plated at a density of $2\times10^5$ cells per well in 24 well plate and co-cultured with 10 ng/mL IFN gamma+/–IL-31 at 100 ng/mL, 10 ng/mL or 1 ng/mL. Supernatants were collected at 24 and 48 hours and assayed f (with and with out antibody challenge), or IL-8 and MCP-1. Cytokine production (pg/mL) for each cell line in the 24-hour samples is measured.

Example 6

Inhibition of IL-31 Effects on U937 Monocyte Adhesion to Transformed Bone Marrow Endothelial Cell (TRBMEC) Monolayer It has been shown that IL-31 can synergize can affect the basal adherence of U937 cells to the endothelial monolayers. In particular, IL-31 synergized with TNFalpha and further enhanced U937 adhesion. See published U.S. patent application (See publication number 20030224487, Sprecher, Cindy et al., 2003. Thus inhibition of IL-31 by the anti-IL-31 antibodies described herein can be measured with the following assay.

Transformed Bone Marrow Endothelial Cells (TRBMEC) are seeded in 96-well tissue clusters (Falcon) at a density of 25,000/well in medium M131 (Cascade Biologics) supplemented with Microvascular Growth Supplement (MVGS) (Cascade Biologics). At confluence (24 hours later), cells are switched to M199 (Gibco-Life Technologies) supplemented with 1% Fetal Bovine Serum (Hyclone). Human recombinant IL-31 (test reagent) is added at various concentrations (from 0.4 to 10 ng/mL) with and without antibody challenge, to test for the effect of the protein on immune cell-endothelial cell interactions resulting in adhesion. Some wells receive 0.3 ng/ml Tumor Necrosis Factor (TNFalpha R&D Systems), a known pro-inflammatory cytokine, in addition to IL-31, to test an effect of the protein on endothelial cells under inflammatory conditions. TNFalpha at 0.3 ng/ml alone is used as positive control and the concentration used represents approximately 70% of the maximal TNFalpha effect in this system, i.e., it does not induce maximal adherence of U937 cells (a human monocyte-like cell line) to the endothelium. For this reason, this setup can detect both upregulation and downregulation of the TNFalpha effects. Basal levels of adhesion both with and without TNFalpha are used as baseline to assess effect of test reagents.

After overnight incubation of the endothelial cells with the test reagents, U937 cells, stained with 5 µM Calcein-AM fluorescent marker (Molecular Probes), the cells are suspended in RPMI 1640 (no phenol-red) supplemented with 1% FBS and plated at 100,000 cells/well on the rinsed TRBMEC monolayer. Fluorescence levels at excitation/emission wavelengths of 485/538 nm (Molecular Devices micro-plate reader, CytoFluor application) are measured 30 minutes later, before and after rinsing the well three times with warm RPMI 1640 (no phenol-red), to remove non-adherent U937. Pre-rinse (total) and post-rinse (adherence-specific) fluorescence levels are used to determine percent adherence (net adherent/net total×100=% adherence).

Example 7

IL-31 Bioassay Protocol

BAF3 cells transfected with hzCYTOR17 (IL-31RA), hOSMRB, and KZ134 are grown to $5 \times 10^5$ and $1 \times 10^6$ cells/mL. Cells are washed with assay media (RPMI 1640, 10% FBS, L-Glutamine, Sodium Pyruvate, and Pen/Strep (all Gibco)) and resuspended at $3 \times 10^5$ cell/mL in assay medium. In a 96-well opaque plate, hIL-31 standards are titered in duplicate from 600 pg/mL to 9.38 pg/mL in assay medium via a 100 μL/well, 1:2 serial dilution. Quality control standards are added in duplicate to the plate at 350 pg/mL and 35 pg/mL in 100 μL. Test samples are often diluted 1:2 or 1:4 and added in duplicate to the sample wells. 100 μL of the washed BAF3 cells are added to each well for a final concentration of $3 \times 10^4$ cells/well. The plate is incubated for 16-24 hours at +37° C. in a 5% $CO_2$ incubator. The plate is centrifuged at 1200 RPM for 5 minutes, media flicked off and 25 μL/well of lysis buffer (Promega) added to each well. After 10 minutes the plate is read on a luminometer (Berthold). The luminometer adds 40 μL/well of luciferase substrate mix (Promega) and integrated the luminescence for a period of 4 seconds. Luminescence values are exported to a spreadsheet where they are analyzed and converted into picograms of IL-31 per $10^6$ cells per mL of volume.

Example 8

IL-31 Involvement in Initiation and Perpetuation of Contact Hyper-Sensitivity In Vivo Method I BALB/c mice are painted on shaved mid-back with 25 ul of 0.5% DNFB dissolved (2,4, dinitro-fluoro-benzene, Sigma, St. Louis Mo.) in acetone:olive oil (4:1) solution using a pipettor. A vehicle control group receives 25 ul of acetone:olive oil only. After 5 days, mice are anaesthetized with isofluorane in an inhalation chamber and both ear pinnae of experimental and control animals are measured with an engineer's micrometer (Mitutoyo) to obtain a baseline measurement. Mice are then challenged by applying 10 ul of 0.25% DNFB in acetone:olive oil (4:1) to both sides of each ear of all mice. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice.

Whole blood and serum for FACS and/or ELISA analysis are collected prior to sacrifice and ears are collected for histology.

Method II (Induces Th2 Responses)

BALB/c mice are painted on shaved mid-back with 100 ul of 0.5% FITC (fluorescein isothiocyanate) in a 1:1 solution of acetone/dibutyl phthalate (MSDS available using pipettor on days 1, 2 and 8. On day 13, mice are anaesthetized with isofluorane in an inhalation chamber and both ear pinnae of experimental and control animals are measured with an engineer's micrometer (Mitutoyo) to obtain a baseline measurement. Mice are challenged by applying 25 ul of 0.5% FITC (in 1:1 acetone/dibutyl phthalate) to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Method III (Induces Th1 Responses)

BALB/c mice are painted on shaved mid-back with 25 ul of 2% oxazalone (in 4:1 acetone/olive oil) using pipettor. On day 7, mice are anaesthetized with isofluorane in an inhalation chamber and both ear pinnae of experimental and control animals are measured with an engineer's micrometer (Mitutoyo) to obtain a baseline measurement. Mice are challenged by applying 8 ul of oxazalone to the dorsal surface of each ear. Contact hyper-sensitivity was measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Involvement of IL-31 in the initiation and perpetuation of contact hyper-sensitivity is tested using the antibodies described herein against IL-31 both at the sensitization and challenge phases of the experiment.

Example 9

IL-31 Involvement in Atopic Dermatitis In Vivo

Methods I (Sensitization of NC/Nga Mice)

Male NC/Nga mice were purchased from CRL Japan. The mice were 4 weeks old on arrival and housed in SPF quarantine conditions for 4 weeks to acclimate. The mice were approximately 10-11 weeks old at the start of the antigen sensitization. Mice were anaesthetized with isofluorane and backs were shaved with electric clippers. Approximately 10 ug of *Dermatophagoides pteronyssinus* (Dp) (Indoor Biotechnologies, special order) extract was injected intradermally at the nape of the neck 3 times per week for 5 to 6 weeks until mice developed skin lesions. Control animals received 10 ul PBS intradermal injections 3 times per week. The Dp extract was prepared according to method by Matsuoka and colleagues. Matsuoka H., et al., *Allergy:* 58, 139 (2003). Briefly, 595 mg Dp lyophilized spent culture extract was dissolved in 12 mL sterile PBS (Gibco). Dp was mixed in a 50 mL Falcon tube on a shaking rocker for 30 minutes. The extract was spun for 10 minutes at 2000 rpm and the supernatant was collected and aliquoted into 1 mL cryovial tubes and stored at −20° C.

Methods II (Sensitization of DO11.10 Mice)

DO11.10 transgenic mice were bred from an in-house colony and were between 9.5 and 14 weeks old at start of antigen sensitization. 24 hours prior to epicutaneous sensitization mice were anaesthetized with isofluorane and the entire trunk (back and abdomen) of mice were shaved with electric clippers. The mice were then tape stripped with Elastin surgical tape (Johnson and Johnson) on the back. 1 cm2 sterile gauze patches were wetted with either 500 ug ovalbumin (Calbiochem 32467) or sterile PBS (Gibco) and adhered to left backside of mice with DuoDerm Extra Thin Dressing (ConvaTec 187932). The patch and dressing were then covered in a body wrap of the Elastin surgical tape so mice could not remove or destroy the patches. Patches were worn for 7 days and removed. The mice were rested for two weeks before having another round of epicutaneous sensitization. Mice received a total of three one-week sensitizations.

Results

Immunohistochemical analysis of IL-31RA expression in lesional and non-lesional skin from dust mite sensitized NC/Nga and OVA sensitized DO1.10 animals showed that IL-31RA is expressed by epidermal keratinocytes in mice, however no significant difference in levels of expression can be found between antigen sensitized versus PBS sensitized animals.

Example 10

Inhibition of Itch by Administration of Rat Anti-Mouse IL-31 Antibodies

In another NC/Nga mouse study, male NC/Nga mice (SLC, Tokyo), age 4 weeks were exposed to NC/Nga mice which were already exhibiting mild to moderate dermatitis. At seven weeks the mice were divided into three groups and received the following treatments. Every fifth day for seven weeks the mice in one group were given IL-31 rat-anti-mouse injections at 10 mg/kg; one group were given injections of mouse serum albumin; and the third group did not receive any treatment. The mice were assessed clinically twice a week for severity of skin lesions. Specifically, involvement of the skin (0=no involvement; 1=back involved; 2=back and face; 3=back, face, and ears) and severity of the lesions (0=normal skin; 1=scaly and dry; 2=nodular lesions; 3=bloody lesions). In addition, scratching was assessed. Mouse scratching using their hind toes was automatically detected and objectively evaluated using MicroAct (Neuroscience, Tokyo, Japan). A small Teflon-coated magnet was implanted subcutaneously into the dorsal side of both hind paws of the mice under Ketalar/Xylazine anaesthesia. The mouse with magnets were placed in an observation chamber surrounded by a round coil. The electric current induced in the coil by the movement of the magnets was amplified and recorded. The analysis program used the following settings to register scratch events: Threshold (V) 0.1; Event Gap (sec) 0.2; Max Freg (HZ) 20.0; Min Freg (Hz) 2.0; and Min Duration (sec) 1.5. Note: in the NC/Nga mouse model, long lasting (>1.5 sec), but not short lasting scratching behavior (0.3-1.5 sec) are related to the dermatitis-specific itch sensation in mice. Overall primary endpoints measured were scratching, dermatitis, and body weight.

Results:

Taken over the entire period, treatment with the rat-antimouse IL-31 antibody did not meet the primary end points. However, additional analysis revealed a significant reduction of scratch by the anti-IL-31 antibody treatment in the time interval of days 22-43. In this time period, as for the whole period, treatment with anti-Il-31 antibodies did not affect the development of atopic dermatitis-like lesions and did not normalize the weight gain of diseased animals, perhaps due to delayed onset of clinical manifestations or by neutralizing auto-antibodies at termination of treatment. In this experiment, scratching behaviour, but not dermatitis, was already increased among most animals at the time when treatment with the antibody was initiated.

Example 11

IL-31 Involvement DTH In Vivo

Methods

To generate a DTH response, mice were sensitized to antigen on day 0 by subcutaneous immunization at the base of the tail with 100 ug ovalbumin (OVA) in complete Freund's adjuvant (CFA, 50-100 ul total volume). One week later mice were anesthetized with isofluorane in an inhalation chamber and both ear pinnae of experimental and control animals were measured with an engineer's micrometer (Mitutoyo) to obtain a baseline measurement. Mice were challenged intradermally with 10 ug OVA in PBS in a total volume of 10 ul into the left ear pinnae, just below the skin without hitting any veins. As a control, mice also received an injection of 10 ul PBS in the right ear pinnae. In some cases, a separate control group given an i.d. injection of OVA in the ear may also be treated with topical corticosteroids as a positive control to inhibit the reaction. At 24 and 48 hr after challenge, mice were anesthetized and ear thickness was measured. Results were expressed as: Specific ear swelling=(24 hr measurement–0 hr measurement) for experimental ear–(24 hr measurement–0 hr measurement) for negative control ear. Induration, the hallmark of DTH, is detectable by 18 hours after injection of sensitized antigen and is maximal by 24-48 hours. The lag in the onset of palpable induration is the reason for naming the response "delayed type."

Results

IL-31 transgenic mice were tested for DTH, however, due to an increase in ear thickness in un-challenged IL-31 transgenic animals, no statistically significant difference in DTH could be determined between IL-31 Tg animals compared to wildtype controls. IL-31 receptor knockout animals were also tested in a DTH response and no significant difference in the DTH response could be observed between receptor knockout and wildtype animals.

Example 12

IL-31 Involvement in Induction of the Itch Response

Methods I (Capsaicin Treatment of IL-31 Treated Mice)

Ten week old BALB/c animals (CRL) were anaesthetized and injected with a long-lasting analgesic agent, bupranorphine hydrochloride, subcutaneously at 0.1 mg/kg before injection of 0.25 ml of 4 mg/ml solution of capsaicin in 10% ethanol+10% Tween-80 in saline subcutaneously into scruff of neck. Animals were kept anaesthetized for at least 30 min following neurotoxin treatment. Forty-eight hours later, 14-day osmotic pumps were implanted subcutaneously for continuous delivery of 20 ug/day of IL-31 for 14 days. Mice were monitored daily for 6 days for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results demonstrated that while non-capsaicin-treated mice showed a mean scratch/hairloss score of 2.625 following three days of IL-31 delivery, capsaicin-treated mice showed a significantly lower score of 1. Thus mice treated with capsaicin prior to IL-31 delivery showed both a delay in incidence of scratching and hairloss and a lower score in the intensity of scratching and hairloss over the six days of the experiment. These data suggest that IL-31 does induce some neuronal component that contributes to the alopecia and pruritis induced by IL-31. Therefore, neutralization of IL-31 may decrease the incidence and intensity of itch, and therefore dermatitis, in patients suffering from skin disorders that involve itch.

Methods II

Mice that are homozygous null for the Tac1 gene express no detectible substance P or neurokinin A. These mice have significantly reduced nociceptive pain responses to moderate to intense stimuli and are therefore a useful tool for studying the contribution of tachykinin peptides to pain/itch processing and inflammatory disease states. Twelve week old, Tac1 knockout mice were implanted with 14-day osmotic pumps delivering 1 ug/day of IL-31 protein and observed daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results of this study show that Tac1 deficient mice were less susceptible to IL-31 induced scratching/hairloss compared to wildtype control mice. While 100% (10/10) of wildtype mice had developed evidence of scratching and hairloss by day 6 of IL-31 treatment, only 33.3% (2/6) Tac1 deficient mice were showing signs of scratching and hairloss at the same time-point. These data show that IL-31 induces a neuronal component that contributes to the scratch/hairloss phenotype in IL-31-treated mice and neutralization of IL-31 may decrease the incidence and intensity of scratching in the context of dermatitis.

Methods III (Administration of IL-31 Neutralizing Antibody)

Normal female BALB/c mice (CRL) approximately 8 to 12 weeks old were implanted subcutaneously with 14-day osmotic pumps (Alzet, #2002) delivering 1 ug/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/0.1% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-m/L-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 can delay the onset of the scratch/hairloss response induced by IL-31.

Example 13

Characterization of Mouse-Anti-Human IL-31 Monoclonal Antibodies

A panel of 21 clonal hybridomas producing monoclonal antibodies (mAbs) specific for (recombinant) human interleukin 31 (IL31) were isolated. Ten hybridomas producing strongly neutralizing mAbs were isolated. These were assigned to two sub-bins based on competitive binding studies. Eleven hybridomas producing weakly neutralizing mAbs were isolated. These were assigned to 4 additional bins based on competitive binding studies. One mAb worked well for Western Blotting, and it also worked well for immunohistochemistry. Three mAbs suitable for use as competitive antagonists were identified. Monoclonal antibodies suitable for use in sandwich immunoassays were also identified.

A. Epitope Binning by Biacore

Materials: the capture antibody was Goat-anti-mouse IgG-Fcγ specific (Jackson #115-005-071); the blocking antibody was polyclonal IgG Fc fragment (Jackson Labs.); the antigen: rIL31 Produced in BHK with a CEE affinity tag; Biacore 1000; Biacore CM5 NHS-activated chip (Biacore, PN BR-1000-14).

Method: Studies were performed on a Biacore1000™ system. BIAlogue v. 1.2 was used for programming run methods. The goat-anti-mouse Fc antibody was covalently immobilized to a Biacore CM5 chip via lysine residues to form the active binding surface for the study. Each of the 21 mouse anti-huIL31 mAb clonal conditioned media supernatants was injected first onto the goat-anti-mouse Fc surface, so that the primary mAb to be tested could bind to the anti-mouse antibody surface in a favorable orientation. Remaining binding sites were then blocked with injection of an irrelevant polyclonal IgG Fc fragment. The antigen (rIl31) was then injected and captured to the primary antibody surface. This was followed by another injection of one of the 21 mouse anti-huIL31 mAb clonal conditioned media supernatants to test binding of the secondary antibody. If the primary and secondary mAb competed for the same binding site on the antigen, the second mAb did not bind. If the two mAbs did not compete for the same binding site on the antigen, the second mAb did bind.

Each supernatant was tested as the primary mAb in combination with the entire set of mAbs. Control cycles were performed to demonstrate lack of response of the secondary mAb in the absence of primary mAb or antigen. Each mAb tested against itself was used as the negative control to established the level of background signal. Data was compiled using BioEvaluation 3.2 RCI software, then loaded into Excel™ for data processing. Between each cycle testing a monoclonal antibody pair, the goat-anti-mouse Fc surface was regenerated with 2×30 sec washes of 50 mM HCl.

The strongly neutralizing mAbs (10) and weakly neutralizing mAbs (11) were studied in two separate panels, with the exception that when the weakly neutralizing mAbs were studied, mAb from hybridoma 292.64.6 was included as a representative of the strongly neutralizing mAbs. In addition, after reviewing the relative affinity measurements and neutralization data in the context of the epitope bins for the first two binning panels, a third panel of binning was performed on 8 "selected" mAbs including both strongly and weakly neutralizing mAbs.

Results: Three panels testing monoclonal antibody pairings were completed for analysis of both strongly neutralizing and weakly neutralizing mAbs. The first panel tested all strongly neutralizing mAbs against one another and the second panel tested all of the weakly neutralizing mAbs (and a representative strongly neutralizing mAb from hybridoma 292.64.6) against each other. A third panel was completed to explicitly evaluate pairing of a subset of both strongly and weakly neutralizing mAb selected for further evaluation.

In addition to variations in the absolute response (RU) measured for different mAb pairs, several of the mAb pairs behaved differently when the orientation of the pairs changed (i.e. one mAb of the pair used as a primary vs secondary mAb). Such behavior is frequently observed and is generally attributed to the mAbs concerned having overlapping epitopes.

A total of four distinct bins were obtained from analysis of the first two completed panels. For the first panel, all of strongly neutralizing antibodies grouped to together to define a single bin (bin 1: 292.12.3, 292.39.5, 292.51.5, 292.63.5, 292.64.6, 292.72.3, 292.84.1, 292.105.4, 292.109.4, 292.118.6). In the second panel, the weakly neutralizing antibodies were grouped into 3 additional major bins (bin 2: 294.35.2, 294.146.5, 292.152.4, 292.152.4, 294.154.5; bin 3: 294.35.3, 291.78.4, 294.158.5, 294.155.6, 294.163.2; bin 4: 294.144.3) that were distinct from a single representative of bin #1 (292.64.6). Additionally, many of the mAb pairings evaluated in panel 2 demonstrated a clear asymmetry of response depending upon the orientation in which the mAbs were tested, indicating some overlap in binding sites. Two mAbs from bin 3, 294.35.3 and 291.78.4, exhibited evidence of competition with mAbs in bin 2 when tested as the secondary mAb. Also in panel 2, the strongly neutralizing antibody 292.64.6 (bin 1) exhibited competition with mAbs in bin 3 when tested as the primary antibody.

After completion of the initial two binning panels, a group of the most strongly neutralizing mAbs and the highest affinity weakly neutralizing mAbs were selected for further evaluation and were tested against each other in panel 3. Results for the third panel were entirely consistent with previous runs showing that the strongly neutralizing antibodies binned together and the weakly neutralizing antibodies separated into the established multiple bins. In addition, the third panel demonstrated a partial overlap in binding of two mAbs from bin 2 (294.35.2 and 292.154.4) with a subset of mAbs assigned to bin 1 (292.12.3, 292.72.3, 292.84). This led to the assignment of sub-bins 1A and 1B within bin 1. In panel 3, mAbs from hybridoma 292.163.2 (bin3) and 292.144.3 (bin 4) binned singly.

B. Microtiter-Plate (Label-Free Competitive ELISA) Epitope Binning

Materials: The capture antibody was goat-anti-mouse IgG (Fcγ specific) Jackson #115-005-071; the blocking antibody was mouse IgG1, (ZymoGenetics); conditioned media supernatants from the hybridomas were used for this study; the antigen was rIL31 Produced in BHK with a CEE affinity tag biotinylated using the a Sulfo-NHS-Biotin kit (Pierce, Rockford, Ill.); Nunc Maxisorp 96-well plates (Nalge Nunc, Rochester, N.Y.); ELISA B (PBS, 0.1% Tween 20, 1% BSA); streptavidin-HRP (Pierce, Rockford, Ill.); TMB substrate (BioFX Laboratories, Owings Mills, Md.)

Method: This method is similar to the label free competitive ELISA (LFC-ELISA) described by Nagata et al (2004). This method for epitope binning utilized biotinylated rIL31. Microtiter plates were coated at 100 μL/well with 1 pg/mL of a goat anti-mouse IgG Fc-γ specific antibody (Jackson ImmunoResearch #115-005-071) diluted in ELISA B (PBS, 0.1% Tween 20, 1% BSA). After binding of this coating antibody for 3 hours at ambient temperature, each mAb-containing conditioned media was diluted in ELISA B to yield an approximate mAb concentration of 0.5 pg/mL and allowed to bind to the goat anti-mouse IgG coated plates overnight at 4° C. (mAb#1). In parallel, a second set of conditioned medias (mAb#2) were diluted in polystyrene test tubes to approximately 0.5 μg/mL mAb in ELISA B, mixed with 50 ng/mL biotinylated rIL31 antigen, and incubated overnight at 4° C. After incubation of mAb#1 with the coating antibody, the plates were blocked with an unrelated antibody to saturate unoccupied binding sites on the plate. The mAb#2-biotin-rIL31 mixtures were added to the plate and allowed to bind. As a control for (non-competition) in the assay, 50 ng/mL biotinylated rIL31 was added directly (without pre-incubation with mAb#2) to wells containing immobilized mAb#1. After incubation with the biotinylated-IL31-mAb#2 complex, streptavidin-HRP (Pierce, Rockford, Ill.) was added to the plate at 0.5 μg/mL. The plates were developed with TMB substrate (BioFX Laboratories, Owings Mills, Md.), and the absorbance of the individual wells at 450 nm was measured with a plate reader (Molecular Devices SpectraMax340, Sunnyvale, Calif.). If mAb#1 recognized a different epitope from mAb#2, the biotin-rIL31-mAb#2 complex bound to the plate resulting in a high absorbance reading. If mAb#1 recognized the same epitope as mAb#2, the biotin-rIL31-MAb#2 complex did not bind to the plate resulting in a low absorbance reading.

Results: The full panel of 21 mAbs were tested against themselves simultaneously in a series of six 96-well microtiter plates. Absorbance values at 450 nm (A450 nm) were recorded for each combination and orientation and compiled. In all cases, low absorbance values were obtained for the self-self combinations. In addition to the self-self control, a positive control of 50 ng/mL rIL31-biotin (without competing mAb#2) was tested using each primary mAb on every plate. Two positive control samples were obtained for each primary mAb, and the values of the duplicate samples were similar. The absorbance values obtained from the positive control wells (without mAb#2) for 9 of the 11 weakly neutralizing mAbs (from bins 2, 3, or 4) were less that the absorbance values measured for the control samples for the remaining mAbs. Presumably this was due to the lower affinity (higher EC50) for those mAbs. To facilitate the interpretation of the results, the absorbance values were normalized so that the maximum absorbance measured for any combination of mAbs across a row (capture mAb (mAb#1) held constant) was assigned a value of 100%. The normalized values fell into two distinct groups: A large cluster of values fell below a value of 32% consistent with competition, and a second large cluster of values fell above 32% consistent with a lack of competition. The 32% threshold value was used to assign each combination and orientation of mAbs to one of two discrete categories (non-competition, and competition). Using the categorized data, binning was performed automatically based on a hierarchical clustering algorithm. As was observed during the binning experiments using the Biacore, some pairs of mAbs categorized differently depending on which mAb was used as the primary mAb. A high level of stringency, requiring competition in both orientations, was used to assign the mAbs to primary bins. Subsequently a less stringent criteria, requiring competition in one orientation only, was used to aid in the assignment of the mAbs to sub-bins based on minor differences in behavior. The normalized data was grouped according to the 5 primary bin assignments based on the high stringency criteria. Additionally, the combinations and orientations of mAbs are color coded (white for competition and dark for non-competition) to aid in visualizing the interactions that led to the assignment of mAbs to sub-bins.

The results of the binning by competitive ELISA are consistent with the bin assignments based on the results of the studies using the Biacore. Using the stringent binning criteria, the following bins were defined:

Bin #1 (containing all of the strongly neutralizing mAbs): 292.72.3, 292.64.6, 292.63.5, 292.51.5, 292.39.5, 292.12.3. 292.118.6, 292.109.4, 292.105.4, 292.84.1

Bin #2: 294.35.2, 294.154.5, 294.146.5, 292.154.4, 292.152.4

Bin #3: 294.35.3, 294.163.2, 294.158.5, 294.155.6

Bin #4: 294.144.3

Bin #5: 291.78.4

Focusing on bin #1, the mAbs from 3 of the hybridomas in bin #1 (292.72.3, 292.12.3, 292.84.1) demonstrated competition with 3 of the mAbs from bin #2 when used as the secondary mAb (mAb#2). Based on this behavior bin 1 was divided into two sub-bins; #1A and #1B, with bin #1B containing the mAbs that compete with the bin 2 mAbs for binding. Bin #1A contains 292.64.6, 292.63.5, 292.51.5, 292.39.5, 292.118.6, 292.109.4, 292.105.4. Bin #1B contains 292.72.3, 292.12.3, and 292.84.1.

Focusing on bin #2, three distinct interactions are apparent that were used to divide bin #2 into 3 sub-bins. Bin #2A contains mAb from hybridoma 294.146.5, which competes with all mAbs from both bins #1 and #2. Bin #2B contains mAbs from hybridomas 294.35.2 and 294.154.5, which compete with (secondary) mAbs from bin #1. Bin #2C contains mAbs from hybridomas 292.154.4 and 292.152.4, which compete with the mAb from bin #4 when it is used as the secondary mAb.

Focusing on bins #3, #4, and #5: The mAbs in bin #3 (from hybridomas 294.35.3, 294.163.2.1, and 294.155.6) compete with the mAbs from both bins #4 and #5 when they are used as secondary mAbs. The mAbs in bins #4 (from hybridoma 294.144.3.5) and #5 are mainly differentiated by their interaction with mAbs in sub-bin #2C (and the unique binding properties of the mAb from hybridoma 294.144.3 on Western blots).

When the full panel of 21 mAbs was tested simultaneously using the LFC-ELISA format, bin 1 and sub-bins #1A and #1B were clearly identified. Partial overlap of bins #2 and #3 was also identified when the complete panel of mAbs was tested simultaneously, and bin #2 was divided into 3 sub-bins One minor deviation from the bin assignments based on Biacore data was the assignment of the mAbs from hybridomas 291.78.4 and 294.144.3 to two distinct bins when strict criteria were used with the LFC-ELISA data. Based on the Biacore studies, mAb from hybridoma 291.78.4 had been assigned to bin #3.

C. Plate Based Affinity Measurement

Materials: The capture polyclonal antibody was goat-anti-mouse IgG (Fcγ specific) (Jackson ImmunoResearch West Grove, Pa. #115-005-071); the blocking polyclonal antibody was mouse anti-human IgG, (Jackson ImmunoResearch, #209-005-082); conditioned media supernatants from the hybridomas were used for this study; the antigen was rIL31 Produced in BHK with a CEE affinity tag biotinylated using the a Sulfo-NHS-Biotin kit (Pierce, Rockford, Ill.); Nunc Maxisorp 96-well plates (Nalge Nunc, Rochester, N.Y.); ELISA B (PBS, 0.1% Tween 20, 1% BSA); streptavidin-HRP (Pierce, Rockford, Ill.); TMB substrate (BioFX Laboratories, Owings Mills, Md.).

Method: This method is similar to that described by van Heyningen (1986). Microtiter plates were coated at 100 μL/well with 1 μg/mL of a goat anti-mouse IgG Fc-γ specific antibody (Jackson ImmunoResearch #115-005-071) diluted in ELISA B (PBS, 0.1% Tween 20, 1% BSA). After binding of this coating antibody for 3 hours at ambient temperature, each purified monoclonal antibody supernatant was diluted in ELISA B to yield and approximate mAb concentration of 1 μg/mL and allowed to bind to the plate for 1 hour at ambient temperature. A serial dilutions of biotinylated rIL31 antigen were prepared from 500 ng/mL to 0 ng/mL in ELISA B and added to the wells. After incubation with the biotinylated antigen, streptavidin-HRP (Pierce, Rockford, Ill.) at 0.5 μg/mL was added to the plate. The plates were developed with TMB substrate (BioFX Laboratories, Owings Mills, Md.), and the absorbance of the individual wells at 450 nm was measured with a plate reader (Molecular Devices SpectraMax340, Sunnyvale, Calif.). Duplicate points were averaged and the data was analyzed with a four-parameter fit. The "C" value of the 4 parameter fit is reported as the apparent EC50 (ng/mL) and is the biotin-rIL31 concentration that produces a half-maximal response in the assay.

Results: Four-parameter fits were obtained from the experimental curves for all 21 of the mAbs. The concentration of biotin-rIL31 producing half-maximal response (EC50) in the assay ranged from 3.3 to 236 ng/mL, with all 10 of the strongly neutralizing mAbs exhibiting low and comparable EC50 values (3.3-4.4 ng/mL).

D. Western Blotting

Materials: The antigen was rIL31 Produced in BHK with a CEE affinity tag; 4-12% NuPAGE Bis-Tris gels (Invitrogen, Carlsbad, Calif.); Non-Reducing sample buffer (Invitrogen, Carlsbad, Calif.); Molecular weight standards were SeeBlue (Invitrogen); 1× MES running buffer (Invitrogen); Western A buffer (50 mM Tris pH 7.4, 5 mM EDTA, 150 mM NaCl, 0.05% Igepal, 0.25% gelatin); 0.2 μm nitrocellulose membranes (Invitrogen); sheep anti-mouse IgG-HRP (Amersham, Piscataway, N.J.); Affinity purified rabbit pAb specific for rIL31 (ZymoGenetics); donkey anti-rabbit Ig-HRP (Amersham); Lumi-Light Plus chemiluminescent Reagent (Roche, Mannheim, Germany); Lumi-Imager (Mannheim-Boehringer)

Method: The ability of the mAbs to detect denatured and denatured/reduced rIL31 on a Western blot was examined in this study. The rIL31 antigen was mixed with either reducing or non-reducing sample buffer, heated at 70° C. for 10 min then loaded at 100 ng/lane on 4-12% NuPAGE Bis-Tris gels (Invitrogen, Carlsbad, Calif.). Molecular weight standards were SeeBlue (Invitrogen), and electrophoresis was performed in 1× MES running buffer (Invitrogen). Protein bands in the gels were transferred to 0.2 μm nitrocellulose membranes (Invitrogen) and blocked overnight in 2.5% non-fat dried milk in Western A buffer (50 mM Tris pH 7.4, 5 mM EDTA, 150 mM NaCl, 0.05% Igepal, 0.25% gelatin). Nitrocellulose membranes were probed with each monoclonal antibody at an approximate concentration of 0.1 μg/mL mAb. The blots were then probed with a secondary antibody conjugated to horseradish peroxidase (sheep anti-mouse IgG-HRP; Amersham, Piscataway, N.J.). As a positive control, a separate Western blot was probed with 0.1 μg/mL of a rabbit polyclonal antibody specific for IL-31 (ZymoGenetics), and a secondary antibody conjugated to horseradish peroxidase (donkey anti-rabbit Ig-HRP; Amersham). Bands on the Western blots were detected with Lumi-Light Plus Reagent (Roche, Mannheim, Germany) and chemiluminescence recorded on a Lumi-Imager (Mannheim-Boehringer).

Results: Western Blot analysis of the anti IL31 mAbs demonstrated that mAbs from only three of the 21 hybridomas detected the denatured rIL31 antigen. The strongest signal was obtained from the mAb produced by hybridoma 294.144.3. This mAb also detected reduced/denatured rIL31 more strongly that non-reduced/denatured rIL31. The intensity of signal observed with this mAb was similar to that obtained with the polyclonal antibody control. It is notable that the mAb from hybridoma 294.144.3 belongs to a bin separate from the other mAbs evaluated. Monoclonal antibodies from two other hybridomas (292.84.1 and 292.64.6) detected non-reduced/denatured rIL31 very weakly but did not detect reduced/denatured rIL31. This weak signal did not reproduce on the scanned blots. Both of these mAbs are neutralizing antibodies from bin #1.

Example 14

Relative Binding Affinity of the Rat Anti-Mouse Monoclonal Antibodies for the IL-31 Ligand The relative binding affinity of four Rat-anti-Ms-IL-31-ligand MAb's against IL-31 ligand was determined as follows. Clone 271.26.6.6.1, Clone 271.33.3.2.1, Clone 271.33.1.2.2, and Clone 271.39.4.6.5 were assayed. Goat-anti-Rat IgG-Fcγ specific Antibody (Jackson) was immobilized onto a CM5 Biacore chip. After preliminary testing, the assay was further optimized to bind each MAb onto the anti-Rat capture surface and then injected a concentration series of IL-31 ligand across the MAb to see association and dissociation. After each run, the surface was regenerated back to the immobilized anti-Rat Antibody with 2 injections of 30 mM HCl. Data was generated for each MAb and evaluation software was used to define relative kinetic values.

The relative kinetic data generated by evaluation of the MAb-antigen binding curves is shown in Table 4.

TABLE 4

| Clone | 271.26.6.6.1 | 271.33.3.2.1 | 271.33.1.2.2 | 271.39.4.6.5 |
|---|---|---|---|---|
| ka (M−1s−1) | 5.61E+05 | 1.43E+05 | 8.19E+05 | 8.94E+05 |
| kd (s−1) | 3.6E−04 | 5.46E−04 | 4.21E−04 | 6.21E−04 |
| KD (M) | 6.42E−10 | 3.81E−9 | 4.73E−10 | 6.94E−10 |
| Chi2 | 0.101 | 0.341 | 0.0917 | 1.92 |

Example 15

Reduction of TARC and MDC in Response to Anti-Il-31 Antibody in AD Mouse Models

Method I

Six-week old male NC/Nga mice (CRL Japan) were sensitized intradermally with 50 μg dust mite extract (*D. pteronyssinus*, Indoor Biotechnologies) three times a week on the back and scored for AD-like lesions. After 5 weeks of sensitization the mice were euthanized and the right ears were excised and placed into a single well of a 48-well culture dish (Corning) supplemented with RPMI+2% FBS (GIBCO Invitrogen). Plates were placed in 5% CO2 humidity controlled incubators. Supernatants were collected after 24 hours and frozen at −20° C. until further analysis.

Method II

Twelve-week old female NC/Nga mice (CRL Japan) were sensitized intradermally with 10 μg SEB (Toxin Technology) in the ear and on the back three times per week. The mice were scored for AD-like lesions. After 5 weeks of sensitization the mice were euthanized and 6 mm biopsy punches were taken from the injected ear of each mouse and placed into a single well of a 48-well culture dish supplemented with RPMI+2% FBS. Plates were placed in 5% CO2 humidity controlled incubators. Supernatants were collected after 24 hours and frozen at −20° C. until further analysis.

Groups of mice in both studies were treated with either a rat anti-mouse IL-31 monoclonal antibody at 10 mg/kg or vehicle, intraperitoneally two times each week starting after 1 to 2 weeks of sensitization.

TARC and MDC concentrations in the 24-hour supernatant samples were measured by conventional ELISA (R&D Systems).

TARC and MDC concentrations were lower in ear supernatants from anti-IL-31 treated mice compared to control mice in both studies, however, these results were not statistically significant when analyzed by ANOVA, probably due to small sample size. When the data from both experiments is combined and analyzed there is a statistically significant difference between treated groups.

Example 16

Administration of IL-31 Neutralizing Antibody

Normal female BALB/c mice (CRL) approximately 8 to 12 weeks old were implanted subcutaneously with 14-day osmotic pumps (Alzet, #2002) delivering 1 ug/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/01% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-mIL-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 can delay the onset of the scratch/hairloss response induced by IL-31.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of reducing inflammation in a mammal with a skin or epidermal condition having increased infiltration of cutaneous lymphocyte antigen (CLA+) T cells comprising administering to the mammal a monoclonal antibody or antibody fragment thereof, wherein the monoclonal antibody is produced by the hybridoma deposited with the American Type Culture Collection having the ATCC Patent Deposit Designation selected from the group consisting of:
   a) ATCC Patent Deposit Designation PTA-6815;
   b) ATCC Patent Deposit Designation PTA-6816;
   c) ATCC Patent Deposit Designation PTA-6829;
   d) ATCC Patent Deposit Designation PTA-6830;
   e) ATCC Patent Deposit Designation PTA-6831;
   f) ATCC Patent Deposit Designation PTA-6871;
   g) ATCC Patent Deposit Designation PTA-6872;
   h) ATCC Patent Deposit Designation PTA-6875; and
   i) ATCC Patent Deposit Designation PTA-6873, wherein the polypeptide consists of amino acid residues 27 to 164 of SEQ ID NO: 2, and wherein the inflammation is reduced.

2. The method according to claim 1, wherein the monoclonal antibody or antibody fragment neutralizes the interaction of the polypeptide with a receptor polypeptide comprising the amino acid sequence of SEQ ID NO:5.

3. The method of claim 1, wherein the monoclonal antibody or antibody fragment comprises a radionuclide, enzyme, substrate, cofactor, fluorescent marker, chemiluminescent marker, peptide tag, magnetic particle, or toxin.

4. The method of claim 1, wherein the monoclonal antibody or antibody fragment comprises PEG.

5. The method of claim 1, wherein the monoclonal antibody or antibody fragment is selected from the group consisting of:
   a) a chimeric antibody or antibody fragment;
   b) a humanized antibody or antibody fragment; and c) a Fab molecule; and
d) a F(ab')₂ molecule.

6. A method of reducing inflammation in a mammal with a skin or epidermal condition having increased infiltration of cutaneous lymphocyte antigen (CLA+) T cells comprising administering to the mammal a monoclonal antibody or antibody fragment thereof that is capable of inhibiting the binding of a polypeptide to a receptor, wherein the monoclonal antibody is produced by the hybridoma deposited with the American Type Culture Collection having the ATCC Patent Deposit Designation selected from the group consisting of:
   a) ATCC Patent Deposit Designation PTA-6815;
   b) ATCC Patent Deposit Designation PTA-6816;
   c) ATCC Patent Deposit Designation PTA-6829;
   d) ATCC Patent Deposit Designation PTA-6830;
   e) ATCC Patent Deposit Designation PTA-6831;
   f) ATCC Patent Deposit Designation PTA-6871;
   g) ATCC Patent Deposit Designation PTA-6872;
   h) ATCC Patent Deposit Designation PTA-6875; and
   i) ATCC Patent Deposit Designation PTA-6873,
   wherein the polypeptide consists of amino acid residues 27 to 164 of SEQ ID NO: 2, wherein the receptor is the IL-31RA receptor of SEQ ID NO: 5, and wherein the inflammation is reduced.

7. The method of claim 6, wherein the monoclonal antibody or antibody fragment comprises a radionuclide, enzyme, substrate, cofactor, fluorescent marker, chemiluminescent marker, peptide tag, magnetic particle, or toxin.

8. The method of claim 6, wherein the monoclonal antibody or antibody fragment comprises PEG.

9. The method of claim 6, wherein the monoclonal antibody or antibody fragment is selected from the group consisting of:
   a) a chimeric antibody or antibody fragment;
   b) a humanized antibody or antibody fragment; and
   c) a Fab molecule; and
   d) a F(ab')₂ molecule.

10. A method of reducing pruritis in a mammal with a skin or epidermal condition having increased infiltration of cutaneous lymphocyte antigen (CLA+) T cells comprising administering to the mammal a monoclonal antibody or antibody fragment thereof, wherein the monoclonal antibody is produced by the hybridoma deposited with the American Type Culture Collection having the ATCC Patent Deposit Designation selected from the group consisting of:
   a) ATCC Patent Deposit Designation PTA-6815;
   b) ATCC Patent Deposit Designation PTA-6816;
   c) ATCC Patent Deposit Designation PTA-6829;
   d) ATCC Patent Deposit Designation PTA-6830;
   e) ATCC Patent Deposit Designation PTA-6831;
   f) ATCC Patent Deposit Designation PTA-6871;
   g) ATCC Patent Deposit Designation PTA-6872;
   h) ATCC Patent Deposit Designation PTA-6875; and
   i) ATCC Patent Deposit Designation PTA-6873,
   wherein the polypeptide consists of amino acid residues 27 to 164 of SEQ ID NO: 2, and wherein the pruritis is reduced.

11. The method according to claim 10, wherein the monoclonal antibody or antibody fragment neutralizes the interaction of the polypeptide with a receptor polypeptide comprising the amino acid sequence of SEQ ID NO:5.

12. The method of claim 10, wherein the monoclonal antibody or antibody fragment comprises a radionuclide, enzyme, substrate, cofactor, fluorescent marker, chemiluminescent marker, peptide tag, magnetic particle, or toxin.

13. The method of claim 10, wherein the monoclonal antibody or antibody fragment comprises PEG.

14. The method of claim 10, wherein the monoclonal antibody or antibody fragment is selected from the group consisting of:
   a) a chimeric antibody or antibody fragment;
   b) a humanized antibody or antibody fragment; and
   c) a Fab molecule; and
   d) a F(ab')₂ molecule.

15. A method of reducing pruritis in a mammal with a skin or epidermal condition having increased infiltration of cutaneous lymphocyte antigen (CLA+) T cells comprising administering to the mammal a monoclonal antibody or antibody fragment thereof that is capable of inhibiting the binding of a polypeptide to a receptor, wherein the monoclonal antibody is produced by the hybridoma deposited with the American Type Culture Collection having the ATCC Patent Deposit Designation selected from the group consisting of:
   a) ATCC Patent Deposit Designation PTA-6815;
   b) ATCC Patent Deposit Designation PTA-6816;
   c) ATCC Patent Deposit Designation PTA-6829;
   d) ATCC Patent Deposit Designation PTA-6830;
   e) ATCC Patent Deposit Designation PTA-6831;
   f) ATCC Patent Deposit Designation PTA-6871;
   g) ATCC Patent Deposit Designation PTA-6872;
   h) ATCC Patent Deposit Designation PTA-6875; and
   i) ATCC Patent Deposit Designation PTA-6873,
   wherein the polypeptide consists of amino acid residues 27 to 164 of SEQ ID NO: 2, wherein the receptor is the IL-31RA receptor of SEQ ID NO: 5, and wherein the pruritis is reduced.

16. The method of claim 15, wherein the monoclonal antibody or antibody fragment comprises a radionuclide, enzyme, substrate, cofactor, fluorescent marker, chemiluminescent marker, peptide tag, magnetic particle, or toxin.

17. The method of claim 15, wherein the monoclonal antibody or antibody fragment comprises PEG.

18. The method of claim 15, wherein the monoclonal antibody or antibody fragment is selected from the group consisting of:
   a) a chimeric antibody or antibody fragment;
   b) a humanized antibody or antibody fragment; and
   c) a Fab molecule; and
   d) a F(ab')₂ molecule.

* * * * *

UNITED STATES PATENT AND TRADEMARK OFFICE
CERTIFICATE OF CORRECTION

PATENT NO.        : 8,017,122 B2
APPLICATION NO.   : 12/420747
DATED             : September 13, 2011
INVENTOR(S)       : Anthony W. Siadak et al.

It is certified that error appears in the above-identified patent and that said Letters Patent is hereby corrected as shown below:

On the Title Page:

Item (56), References Cited, under OTHER PUBLICATIONS:

Column 2, Wills-Karp, M. reference, change "inerleukin" to -- interleukin --.
The reference should read:
-- Wills-Karp, M., "The gene encoding interleukin-13: a susceptibility locus for asthma and related traits," Respiratory Research, 1(1):19-23, Jul. 17, 2000. --.

Column 2, Connors et al. reference, change "Hamatol" to -- Hematol --.
The reference should read:
-- Connors et al., "Hematology", pp. 263-268, Am Soc Hematol Educ Program, 2002. --.

In the Specification:

Column 5, line 18, change "Zcyto17rlig" to -- Zcyto17lig --.
Column 5, lines 31 and 32, change "SEQ ID NOs: 10 and 11" to -- SEQ ID NOs: 3 and 4 --.
Column 5, lines 45 and 46, change "SEQ ID NO:7" to -- SEQ ID NO:6 --.
Column 6, line 33, change "SEQ ID NO:11" to -- SEQ ID NO:4 --.
Column 7, lines 34 and 35, change "SEQ ID NO:11" to -- SEQ ID NO:4 --.
Column 7, line 35, after "46-51 of", change "SEQ ID NO:11" to -- SEQ ID NO:4 --.
Column 7, line 36, change "SEQ ID NO:11" to -- SEQ ID NO:4 --.
Column 7, line 37, change "SEQ ID NO:11" to -- SEQ ID NO:4 --.
Column 7, line 38, change "SEQ ID NO:11" to -- SEQ ID NO:4 --.

Signed and Sealed this
Fourth Day of June, 2013

Teresa Stanek Rea
*Acting Director of the United States Patent and Trademark Office*

CERTIFICATE OF CORRECTION (continued)
U.S. Pat. No. 8,017,122 B2

In the Specification:

Column 7, line 50, change "SEQ ID NO:11" to -- SEQ ID NO:4 --.

Column 8, line 40, change "SEQ ID NO:11" to -- SEQ ID NO:4 --.

Column 8, line 41, change "SEQ ID NO:11" to -- SEQ ID NO:4 --.

Column 8, line 42, change "SEQ ID NO:11" to -- SEQ ID NO:4 --.

Column 8, lines 42 and 43, after "158-163 of", change "SEQ ID NO:11" to -- SEQ ID NO:4 --.

Column 8, line 43, after "157-162 of", change "SEQ ID NO:11" to -- SEQ ID NO:4 --.

Column 10, line 38, change "SEQ ID NO:11" to -- SEQ ID NO:4 --.

Column 48, line 33, change "SEQ ID NO:11" to -- SEQ ID NO:4 --.

Column 50, line 22, change "SEQ ID NO:11" to -- SEQ ID NO:4 --.

Column 50, line 24, change "SEQ ID NO:11" to -- SEQ ID NO:4 --.

Column 50, lines 25 and 26, change "SEQ ID NO:11" to -- SEQ ID NO:4 --.

Column 50, line 27, change "SEQ ID NO:11" to -- SEQ ID NO:4 --.

Column 50, line 29, change "SEQ ID NO:11" to -- SEQ ID NO:4 --.

Column 50, line 31, change "SEQ ID NO:11" to -- SEQ ID NO:4 --.

Column 50, line 34, change "SEQ ID NO 11" to -- SEQ ID NO:4 --.

Column 50, line 42, change "SEQ ID NO:1" to -- SEQ ID NO:4 --.

Column 50, line 44, change "SEQ ID NO:11" to -- SEQ ID NO:4 --.